US008394837B2

(12) United States Patent
Nantermet et al.

(10) Patent No.: US 8,394,837 B2
(45) Date of Patent: Mar. 12, 2013

(54) 2,3,4,6-SUBSTITUTED PYRIDYL DERIVATIVE COMPOUNDS USEFUL AS BETA-SECRETASE INHIBITORS FOR THE TREATMENT OF ALZHEIMER'S DISEASE

(75) Inventors: Philippe G. Nantermet, Lansdale, PA (US); Hemaka A. Rajapakse, Wyncote, PA (US); Harold G. Selnick, Ambler, PA (US); James C. Barrow, Harleysville, PA (US); Shaun R. Stauffer, Schwenksville, PA (US); Joseph P. Vacca, Telford, PA (US); Keith P. Moore, North Wales, PA (US); Shawn J. Stachel, Perkasie, PA (US); Mattahew G. Stanton, WestPoint, PA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 1228 days.

(21) Appl. No.: 11/791,204

(22) PCT Filed: Nov. 18, 2005

(86) PCT No.: PCT/US2005/042087
§ 371 (c)(1),
(2), (4) Date: May 18, 2007

(87) PCT Pub. No.: WO2006/057945
PCT Pub. Date: Jun. 1, 2006

(65) Prior Publication Data
US 2007/0293497 A1  Dec. 20, 2007

Related U.S. Application Data

(60) Provisional application No. 60/630,539, filed on Nov. 23, 2004, provisional application No. 60/653,037, filed on Feb. 15, 2005, provisional application No. 60/693,271, filed on Jun. 23, 2005.

(51) Int. Cl.
*A61K 31/4439* (2006.01)
*C07D 413/04* (2006.01)
(52) U.S. Cl. .................... 514/340; 546/269.4
(58) Field of Classification Search ........... 546/269.4; 514/340
See application file for complete search history.

(56) References Cited

U.S. PATENT DOCUMENTS

| 4,518,601 A | 5/1985 | Kristiansen et al. |
| 7,109,217 B2 | 9/2006 | Coburn et al. |
| 7,115,652 B2 | 10/2006 | Yang |
| 2004/0132782 A1 | 7/2004 | Yang et al. |
| 2006/0058278 A1 | 3/2006 | Coburn et al. |
| 2006/0149092 A1 | 7/2006 | Nantermet et al. |
| 2006/0161020 A1 | 7/2006 | Coburn et al. |
| 2006/0293380 A1 | 12/2006 | Nantermet et al. |
| 2007/0037784 A1 | 2/2007 | Coburn et al. |
| 2008/0015233 A1* | 1/2008 | Barrow et al. ........... 514/340 |

FOREIGN PATENT DOCUMENTS

| WO | WO 2004/050619 | 6/2004 |
| WO | WO2004/089911 A | 10/2004 |
| WO | WO 2005/051914 | 6/2005 |
| WO | WO 2005/065195 | 7/2005 |
| WO | WO 2005/097767 | 10/2005 |
| WO | WO 2005/103020 | 11/2005 |
| WO | WO 2005/103043 | 11/2005 |

OTHER PUBLICATIONS

Structure-Based Design of Potent and Selective Cell-Permeable Inhibitors of Human B-Secretase (BACE-1), Stachel, et al., J. Med Chem, 2004, 47, 6447-6450.
Identification of a Small Molecule Nonpeptide Active Site B-Secretase Inhibitor that Displays a Nontraditional Binding Mode for Aspartyl Proteases, Coburn, et al., J. Med Chem, 2004, 47, 6117-6119.
Design and Synthesis of 4-Substituted Benzamides as Potent, Selective, and Orally Bioavailable Iks Blockers, Llloyd, et al., J. Med Chem, 2001, 44, 3764-3767.
Supplementary European Search Report for PCT/US2005/042087 dated Aug. 18, 2010; 5 pages.
Nantermet, P.; et. al.; "Evolution of Tertiary Carbinamine BACE-1 Inhibitors Aβ Reduction in Rhesus CSF upon Oral Dosing", ChemMedChem; 2009; 4, pp. 37-40.
Zhu, H.; et. al.; "Rapid P1 SAR of brain penetrant tertiary carbinamine derived BACE inhibitors", Biiorganic and Medicinal Chemistry Letters, 20 (2010) 1779-1782.
International Search Report for PCT/US05/013480 filed Apr. 20, 2005 mailed on Jul. 20, 2005; 3 pages.
Written Opinion for PCT/US05/013480 filed Apr. 20, 2005 mailed on Jul. 20, 2005; 4 pages.
International Search Report for PCT/US05/042087 filed Nov. 18, 2005 mailed on Jul. 14, 2006; 3 pages.
Written Opinion for PCT/US05/042087 filed Nov. 18, 2005 mailed on Jul. 14, 2006; 4 pages.
Sankaranarayanan, S.; et. al.; "First Demonstration of Cerebrospinal Fluid and Plasma Aβ Lowering with Oral Administraiton of a β-Site Amyloid Precursor Protein-Cleaving Enzyme 1 Inhibitor in Nonhuman Primates"; The Journal of Pharmacology and Experimental Therapeutics; vol. 328, No. 1; available online at http://ipet.aspetjournals.org.doi:10.1123/ipet.108.143628; Oct. 10, 2008; pp. 131-140.
Rajapakse, H.; et. al.; SAR of tertiary carbinamine derived BACE1 inhibitors: Role of aspartate ligand amine $pK_a$ in enzyme inhibition; Bioorganic & Medicinal Chemistry Letters; vol. 20; available online on Feb. 4, 2010, pp. 1885-1889.
Rajapakse, H.; et. al.; Discovery of Oxadiazoyl Tertiary Carbinamin Inhibitors of β-Secretase (BACE-1)⁺; J. Med. Chemistry, vol. 49, Published on web Nov. 10, 2006, pp. 7270-7273.

* cited by examiner

*Primary Examiner* — Patricia Morris
(74) *Attorney, Agent, or Firm* — Keith D. MacMillan; Gerard M. Devlin

(57) ABSTRACT

The present invention is directed to 2,3,4,6-substituted pyridyl derivative compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

14 Claims, No Drawings

2,3,4,6-SUBSTITUTED PYRIDYL DERIVATIVE COMPOUNDS USEFUL AS BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) from U.S. provisional applications Ser. Nos. 60/630,539, filed Nov. 23, 2004; 60/653,037, filed Feb. 15, 2005; and 60/693,271, filed Jun. 23, 2005.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to a class of novel 2,3,4,6-substituted pyridyl derivative compounds which are useful as inhibitors of the β-secretase enzyme, and to the treatment of diseases in which the β-secretase enzyme is involved, such as Alzheimer's Disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2-$ and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochein. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to 2,3,4,6-substituted pyridyl derivative compounds represented by general formula (I)

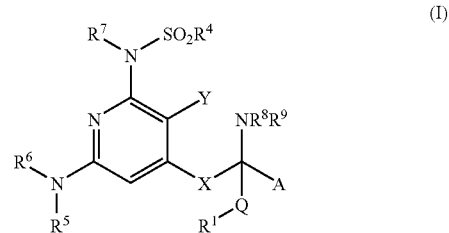

(I)

and individual enantiomers and diastereomers thereof, and pharmaceutically acceptable salts thereof, which are useful as inhibitors of the β-secretase enzyme.

The invention is also directed to pharmaceutical compositions comprising an effective amount of a compound of formula (I), or pharmaceutically acceptable salts thereof, and a pharmaceutically acceptable carrier. The invention is also directed to methods of treating mammals for diseases in which the β-secretase enzyme is involved, such as Alzheimer's Disease, and the use of the compounds and pharmaceutical compositions of the invention in the treatment of such diseases.

DETAILED DESCRIPTION OF THE INVENTION

The present invention is directed to compounds of formula (I):

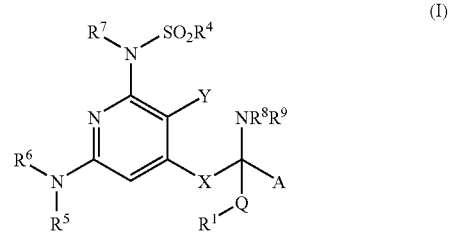

(I)

wherein:
X is selected from the group consisting of

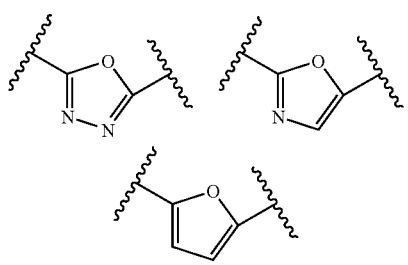

Y is selected from the group consisting of
(1) halogen,
(2) cyano,
(3) —$C_{1-6}$ alkyl, and
(4) —$C_{6-10}$ aryl;
A is selected from the group consisting of
(1) hydrogen,
(2) —$C_{1-10}$ alkyl, and
(3) —$C_{2-10}$ alkenyl,
wherein said alkyl or alkenyl is unsubstituted or substituted with one or more
(a) halo,
(b) —$C_{3-12}$ cycloalkyl,
(c) —OH,
(d) —CN,
(e) —O—$C_{1-10}$ alkyl,
(f) phenyl, or
(g) heteroaryl,
and said phenyl and heteroaryl is unsubstituted or substituted with one or more
(i) halo,
(ii) —OH,
(iii) —CN,
(iv) —O—$C_{1-10}$ alkyl,
(v) —$C_{1-10}$ alkyl, or
(vi) —$C_{3-12}$ cycloalkyl;
Q is —$C_{0-3}$ alkyl, wherein said alkyl is unsubstituted or substituted with one or more
(1) halo,
(2) —$C_{3-12}$ cycloalkyl,
(3) —OH,
(4) —CN,
(5) —O—$C_{1-10}$ alkyl, and
(6) —$C_{1-10}$ alkyl;
$R^1$ is selected from the group consisting of
(1) aryl selected from the group consisting of phenyl and napthyl,
(2) heteroaryl,
(3) —$C_{1-10}$ alkyl, and
(4) —$C_{3-8}$ cycloalkyl, said cycloalkyl optionally fused to a $C_{6-10}$ aryl group,
wherein said alkyl, cycloalkyl, aryl or heteroaryl is unsubstituted or substituted with one or more
(a) halo,
(b) —$C_{1-10}$ alkyl, wherein said alkyl is unsubstituted or substituted with halogen,
(c) —OH,
(d) —CN,
(e) —O—$C_{1-10}$ alkyl,
(f) —$C_{3-12}$ cycloalkyl, or
(g) —$NR^{10}R^{11}$, wherein $R^{10}$ and $R^{11}$ are selected from the group consisting of
(i) hydrogen,
(ii) —$C_{1-10}$ alkyl, and
(iii) —$C_{0-6}$ alkylene-$C_{6-10}$ aryl;
$R^8$ and $R^9$ are selected from the group consisting of
(1) hydrogen,
(2) $C_{1-10}$ alkyl, and
(3) $C_{0-6}$ alkylene-$C_{6-10}$ aryl;
$R^4$ is selected from the group consisting of
(1) —$C_{1-10}$ alkyl,
(2) heteroaryl, and
(3) —$NR^{12}R^{13}$, wherein $R^{12}$ and $R^{13}$ are selected from the group consisting of
(a) hydrogen,
(b) $C_{1-10}$ alkyl, and
(c) $C_{0-6}$ alkylene-$C_{6-10}$ aryl,
or $R^{12}$ and $R^{13}$ represent 4, 5 or 6 ring atoms selected from the group consisting of $CR^aR^b$, S, $NR^c$ and O, which form a non-aromatic ring with the nitrogen to which they are attached,
wherein said alkyl, alkylene and heteroaryl is unsubstituted or substituted with one or more
(a) halo,
(b) —OH,
(c) —CN,
(d) —O—$C_{1-10}$ alkyl,
(e) —$C_{1-10}$ alkyl,
(f) —$C_{3-12}$ cycloalkyl,
(g) aryl selected from the group consisting of phenyl and napthyl,
(h) heteroaryl, or
(i) —C(=O)—$C_{1-10}$ alkyl,
and said aryl and heteroaryl is unsubstituted or substituted with one or more
(i) halo,
(ii) —OH,
(iii) —CN,
(iv) —O—$C_{1-10}$ alkyl,
(v) —$C_{3-12}$ cycloalkyl, or
(vi) —$C_{1-10}$ alkyl;
$R^7$ is selected from the group consisting of
(1) hydrogen,
(2) —$C_{1-10}$ alkyl,
(3) —$C_{3-7}$ cycloalkyl,
(3) —$C_{6-10}$ aryl, and
(4) heteroaryl,
wherein said alkyl, cycloalkyl, aryl and heteroaryl is unsubstituted or substituted with one or more
(a) halo,
(b) —OH,
(c) —CN,
(d) —O—$C_{1-10}$ alkyl,
(e) —$C_{3-12}$ cycloalkyl,
(f) a non-aromatic cyclic group consisting of 4, 5 or 6 ring atoms selected from, the group consisting of $CR^aR^b$, S, $NR^c$ and O,
(g) aryl selected from the group consisting of phenyl and napthyl, or
(h) —$C_{5-12}$ heteroaryl,
wherein said cycloalkyl, aryl or heteroaryl is unsubstituted or substituted with one or more
(i) halo,
(ii) —OH,
(iii) —CN,
(iv) —O—$C_{1-10}$ alkyl,
(v) —$C_{3-12}$ cycloalkyl, or
(vi) aryl selected from the group consisting of phenyl and napthyl;
or $R^4$ and $R^7$ may be linked to form a —$CH_2CH_2CH_2$— group;
$R^5$ and $R^6$ are independently selected from the group consisting of
(1) hydrogen,
(2) —$C_{1-10}$ alkyl,
(3) —$C_{2-10}$ alkenyl,
(4) —$C_{2-10}$ alkynyl, and
(5) —$C_{1-10}$ alkylene-$C_{3-12}$ cycloalkyl;
wherein said alkyl, alkylene, cycloalkyl, alkenyl or alkynyl is unsubstituted or substituted with one or more
(a) halo,
(b) —OH,
(c) —CN,
(d) —$C_{1-10}$ alkyl, (e) —$C_{3-12}$ cycloalkyl,
(f) —O—$C_{1-10}$ alkyl, wherein said alkyl is unsubstituted or substituted with —O—$C_{1-10}$ alkyl-(—O—$C_{10}$ alkyl)$_m$,
(g) heteroaryl,
  wherein said heteroaryl may be unsubstituted or substituted with one or more
  (A) halogen, or
  (B) —$C_{1-10}$ alkyl,
(h) phenyl,
(i) —$NR^{14}R^{15}$, wherein $R^{14}$ and $R^{15}$ are selected from the group consisting of
  (A) hydrogen,
  (B) —$C_{1-10}$ alkyl, and
  (C) —$C_{0-6}$ alkyl-$C_{6-10}$ aryl,
(j) —C(=O)—$OR^{16}$, wherein $R^{16}$ is selected from the group consisting of
  (A) hydrogen,
  (B) —$C_{1-10}$ alkyl, and
  (C) —$C_{0-6}$ alkylene-$C_{6-10}$ aryl, and
(k) —C(=O)—$NR^{17}R^{18}$, wherein $R^{17}$ and $R^{18}$ are selected from the group consisting of
  (A) hydrogen,
  (B) —$C_{1-10}$ alkyl, and
  (C) —$C_{0-6}$ alkylene-$C_{6-10}$ aryl,
  or $R^{17}$ and $R^{18}$ represent 4, 5 or 6 ring atoms selected from the group consisting of $CR^aR^b$, S, $NR^c$ and O, which form a non-aromatic ring with the nitrogen to which they are attached, and
(l) —C(=O)—$R^{19}$, wherein $R^{19}$ is selected from the group consisting of
  (A) -$C_{1-10}$ alkyl,
  (B) —$C_{3-7}$ cycloalkyl, and
  (C) —$C_{0-6}$ alkylene-$C_{6-10}$ aryl,
or $R^5$ and $R^6$ are joined together with the nitrogen atom to which they are attached to form a 4-6 membered ring, which is unsubstituted or substituted with one or more
(a) —$C_{1-10}$ alkyl,
(b) —$C_{3-12}$ cycloalkyl,
(c) —$(CH_2)_n$-phenyl,
(d) —$C_{2-10}$ alkenyl, or
(e) —$C_{2-10}$ alkynyl,
  wherein said alkyl, alkenyl and alkynyl is unsubstituted or substituted with one or more
  (i) halo,
  (ii) —OH,
  (iii) —CN,
  (iv) —O—$C_{1-10}$ alkyl, or
  (v) —$C_{3-12}$ cycloalkyl,
and said cycloalkyl and phenyl is unsubstituted or substituted with one or more
  (i) halo,
  (ii) —$C_{1-10}$ alkyl,
  (iii) —OH,
  (iv) —CN,
  (v) —$C_{3-12}$ cycloalkyl, or
  (vi) —O—$C_{1-10}$ alkyl;
$R^a$, $R^b$ and $R^c$ are each independently selected from the group consisting of
(1) hydrogen,
(2) halogen,
(3) —$C_{1-6}$ alkyl, and
(4) —C(=O)—$C_{1-16}$ alkyl;
m is 0, 1 or 2;
n is 0, 1, 2, 3 or 4;
and pharmaceutically acceptable salts thereof, and individual enantiomers and diastereomers thereof.

The present invention is further directed to a method for the manufacture of a medicament or a composition for inhibiting β-secretase enzyme activity in humans and animals comprising combining a compound of the present invention with a pharmaceutical carrier or diluent. The present invention is also directed to a method for the manufacture of a medicament or a composition for treating Alzheimer's Disease in humans, comprising combining a compound of the present invention with a pharmaceutical carrier or diluent.

In one embodiment, X is the oxadiazole selected from the group consisting of

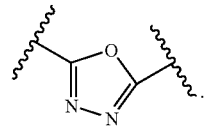 [SMILES: *c1nnc(*)o1]

In one embodiment, Y is halogen, preferably chloro.

In one embodiment, the invention is directed to compounds of formula (I) wherein $R^1$ is phenyl, unsubstituted or substituted, and Q is preferably $CH_2$. Preferably, $R^1$ is unsubstituted phenyl or 4-fluorophenyl.

In other embodiments, $R^1$ is heteroaryl. Preferred $R^1$ heteroaryl groups include pyridyl, furanyl, oxazolyl, and benzodioxolyl.

In other embodiments, $R^1$ is $C_{1-2}$ alkyl or a $C_{3-8}$ cycloalkyl group. Preferred $C_{1-12}$ alkyl $R^1$ groups include $C_{1-6}$ alkyl (preferably unsubstituted $C_{1-6}$ alkyl, including methyl and isopropyl.) Preferred $C_{3-8}$ cycloalkyl groups include cyclopropyl, cyclopentyl and cyclohexyl, preferably unsubstituted. Two of the ring carbon atoms from the cycloalkyl group may be linked to form a $C_{6-12}$ aryl. An exemplary fused group of this embodiment is:

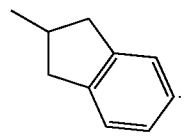

In another embodiment, the invention is directed to compounds of formula (I) wherein both $R^8$ and $R^9$ are hydrogen.

In another embodiment of the compounds of formula (I), A is $C_{1-10}$ alkyl, unsubstituted or substituted (preferably unsubstituted), preferably $C_{1-6}$ alkyl, unsubstituted or substituted (preferably unsubstituted), and even more preferably methyl.

In alternative embodiments, A may be hydrogen.

In one embodiment, $R^6$ is —$C_{1-10}$ alkylene-$C_{3-12}$ cycloalkyl, wherein the cycloalkyl is preferably substituted with $C_{1-10}$ alkyl. In preferred embodiments, $R^6$ is —$C_{1-3}$ alkylene-$C_{3-6}$ cycloalkyl, wherein the cycloalkyl is preferably substituted with $C_{1-3}$ alkyl.

In one embodiment, $R^5$ is $C_{1-10}$ alkyl, optionally substituted with one or more
(a) halo,
(b) —OH,
(c) —CN,
(d) —O—$C_{1-10}$ alkyl, or
(e) heteroaryl.

In another embodiment of the compounds of formula (I), $R^5$ and $R^6$ are joined together with the nitrogen atom to which they are both linked to form a pyrrolidine ring.

In another embodiment of the compounds of formula (I), $R^4$ and $R^7$ are $C_{1-10}$ alkyl, preferably $C_{1-6}$ alkyl. More preferably, $R^4$ is methyl or isopropyl and $R^7$ is methyl.

In another embodiment, $R^4$ is —$C_{0-3}$ alkylene-heteroaryl. Preferred $R^4$ heteroaryl groups include pyridiyl, isoxazolyl, imidazolyl and oxazolyl.

In another embodiment, $R^7$ is —$C_{0-3}$ alkylene-heteroaryl. Preferred $R^7$ heteroaryl groups include pyridiyl, isoxazolyl and tetrazolyl.

In another embodiment, the invention is directed to compounds of formula (II)

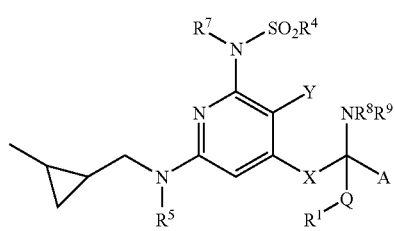

(II)

wherein Y is halogen, and A, X, Q, $R^1$, $R^4$, $R^5$, $R^7$, $R^8$ and $R^9$ are as defined above, and pharmaceutically acceptable salts thereof, and individual enantiomers and diastereomers thereof.

In one embodiment, X is the oxadiazole group

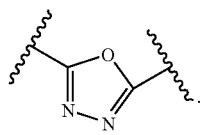 [SMILES: *c1nnc(*)o1]

In one embodiment, Y is halogen, preferably chloro.

In one embodiment of the compounds of formula (II), $R^1$ is phenyl and Q is $CH_2$. Preferably, $R^1$ is unsubstituted phenyl or 4-fluorophenyl.

In another embodiment, the invention is directed to compounds of formula (II) wherein $R^8$ and $R^9$ are hydrogen.

In another embodiment of the compounds of formula (II), A is $C_{1-10}$ alkyl, preferably $C_{1-6}$ alkyl, more preferably methyl.

In another embodiment of the compounds of formula (II), $R^4$ and $R^7$ are $C_{1-10}$ alkyl, preferably $C_{1-6}$ alkyl. More preferably, $R^4$ is methyl or isopropyl and $R^7$ is methyl.

In one embodiment, $R^5$ is $C_{1-10}$ alkyl, optionally substituted with one or more (a) —O—$C_{1-10}$ alkyl, wherein said alkyl is unsubstituted or substituted with —O—$C_{1-10}$ alkyl-(—O—$C_{1-10}$ alkyl)$_m$, (b) heteroaryl, or (c) —C(=O)—$R^{19}$, wherein $R^{19}$ is selected from the group consisting of (i) —$C_{1-10}$ alkyl, (ii) —$C_{3-7}$ cycloalkyl, or (iii) —$C_{0-6}$ alkylene-$C_{6-10}$ aryl.

In an alternative embodiment, $R^5$ is hydrogen.

In a preferred embodiment of compounds of formula (II), X is oxadiazole, as depicted in (III) below:

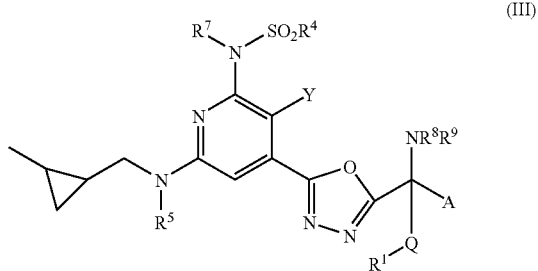

(III)

wherein Y is halogen, and A, Q, $R^1$, $R^2$, $R^4$, $R^5$, $R^7$, $R^8$ and $R^9$ are as defined above, and pharmaceutically acceptable salts thereof, and individual enantiomers and diastereomers thereof.

In one embodiment of the compounds of formula (III), Y is chloro.

In one embodiment of the compounds of formula (III), $R^1$ is phenyl and Q is $CH_2$.

In another embodiment of the compounds of formula (III), $R^8$ and $R^9$ are both hydrogen.

In another embodiment of the compounds of formula (III), A is methyl.

In another embodiment of the compounds of formula (III), $R^4$ and $R^7$ are $C_{1-10}$ alkyl, preferably $C_{1-6}$ alkyl. More preferably, $R^4$ is methyl or isopropyl and $R^7$ is methyl.

In one embodiment, $R^5$ is $C_{1-10}$ alkyl, optionally substituted with one or more (a) —O—$C_{1-10}$ alkyl, wherein said alkyl is unsubstituted or substituted with —O—$C_{1-10}$ alkyl-(—O—$C_{1-10}$ alkyl)$_m$, (b) heteroaryl, or (c) —C(=O)—$R^{19}$, wherein $R^{19}$ is selected from the group consisting of (i) —$C_{1-10}$ alkyl, (ii) —$C_{3-7}$ cycloalkyl, or (iii) —$C_{0-6}$ alkylene-$C_{6-10}$ aryl.

In an alternative embodiment, $R^5$ is hydrogen.

A preferred enantiomeric configuration of compounds of formula (II) and (III) have a trans-S,S configuration at the methyl-cyclopropyl-methyl moiety, as depicted below in formula (III') and

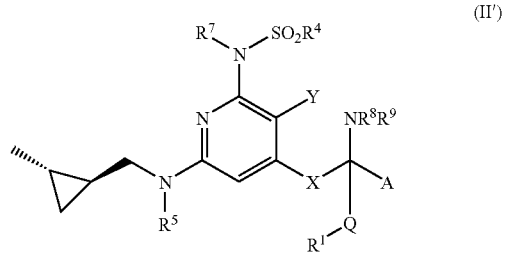

(II')

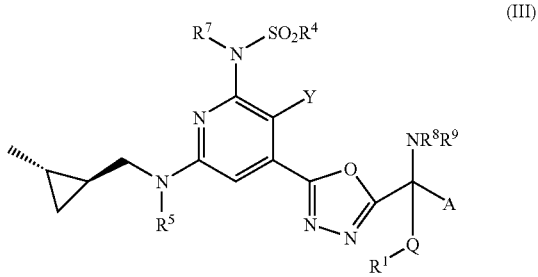

(III)

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkylene," by itself or as part of another substituent, means a saturated straight or branched chain divalent hydrocarbon radical having the number of carbon atoms designated. The term $C_0$ alkylene (for example, in the radical "—$C_0$ alkylene-$C_{6-10}$ aryl") means that the alkylene group is absent.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkenyl groups include ethynyl and propynyl.

As used herein, the term "cycloalkyl," by itself or as part of another substituent, means a saturated monocyclic, polycyclic or bridged cyclic hydrocarbon radical having the number of carbon atoms designated (e.g., $C_{3-12}$ cycloalkyl means a cycloalkyl group having from three to twelve carbon atoms). Preferred cycloalkyl groups include $C_{3-8}$ cycloalklyl groups, especially $C_{3-8}$ monocyclic cycloalkyl groups. Exemplary monocyclic cycloalkyl groups include cyclopropyl, cyclobutyl, cyclopentyl, cyclohexyl and the like. Exemplary bridged cycloalkyl groups include adamantly and norbornyl.

As used herein, the term "aryl," by itself or as part of another substituent, means an aromatic or cyclic radical having the number of carbon atoms designated (e.g., $C_{6-10}$ aryl means an aryl group having from six to ten carbons atoms). Preferred aryl groups for use in the invention include phenyl and naphthyl.

The term "halo" or "halogen" includes fluoro, chloro, bromo and iodo.

As used herein, the term "heteroaryl," by itself or as part of another substituent, means an aromatic cyclic group having ring carbon atoms and at least one ring heteroatom (O, N or S). Preferred heteroaryl groups have from 5 to 12 ring atoms. More preferred heteroaryl groups have five or six ring atoms. Exemplary heteroaryl groups for use in the invention include chromenyl, furanyl, benzofuranyl, isobenzofuranyl, imidazolyl, benzimidazolyl, indazolyl, indolyl, indynyl, oxadiazolyl, oxazolyl, benzoxazolyl, isoxazolyl, pyranyl, pyrazinyl, pyrazolyl, pyridazinyl, pyridyl, pyrimidinyl, pyrrolyl, quinolyl, isoquinolyl, tetrazolyl, thiazolyl, thienyl, thiophenyl, benzothiophenyl, triazinyl and triazolyl.

The term "heteroaryl" also includes fused aromatic cyclic groups which are partially aromatic (i.e., one of the fused rings is aromatic and the other is non-aromatic). Exemplary heteroaryl groups which are partially aromatic include tetrahydroquinolyl, dihydrobenzofuranyl and dihydroindolyl.

When a heteroaryl group as defined herein is substituted, the substituent may be bonded to a ring carbon atom of the heteroaryl group, or on a ring heteroatom (i.e., a nitrogen), which has a valence which permits substitution. Preferably, the substituent is bonded to a ring carbon atom. Similarly, when a heteroaryl group is defined as a substituent herein, the point of attachment may be at a ring carbon atom of the heteroaryl group, or at a ring heteroatom (i.e., a nitrogen, oxygen or sulfur), which has a valence which permits attachment.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

In the compounds of formulas (I) and (II), the carbon atom to which $R^2$, A and Q are bonded is typically a chiral carbon. As a result, the compounds of formulas (I) and (II) may be present as racemates, or in the stereochemically pure (R) or (S) forms. The isomeric forms for compounds of formula (I) are depicted below:

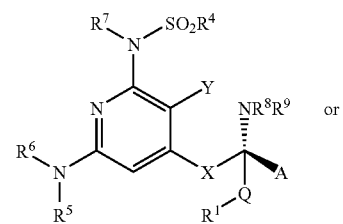

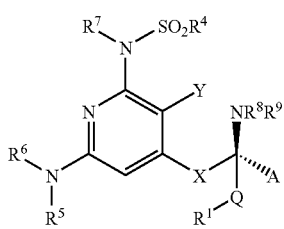

The first configuration depicted above (which is typically the (R) configuration, e.g. when A is $CH_3$, $R^2$ is $NH_2$, Q is $-CH_2-$ and $R^1$ is phenyl) is preferred.

The compounds claimed in this invention can be prepared according to the following general procedure methods, and the specific examples The compounds claimed in this invention can be prepared according to the following general procedures.

In Scheme 1, an amino acid derivative of type 1.1 is converted to the corresponding Boc-acid 1.2. To access commercially unavailable amino acid derivatives, a two step alkylation of glycine Schiff base 1.3 can be used. Schiff base deprotection, Boc protection and ester hydrolysis provides an alternate route to compound 1.2. The alkylation of 1.3 for the synthesis of 1.4 may be performed in an enantioselective manner as described in the literature (see K. Maruoka et al, *J. Am. Chem. Soc.* 2000, 122, 5228-5229 and M. North et al, *Tetrahedron Lett.* 2003, 44, 2045-2048).

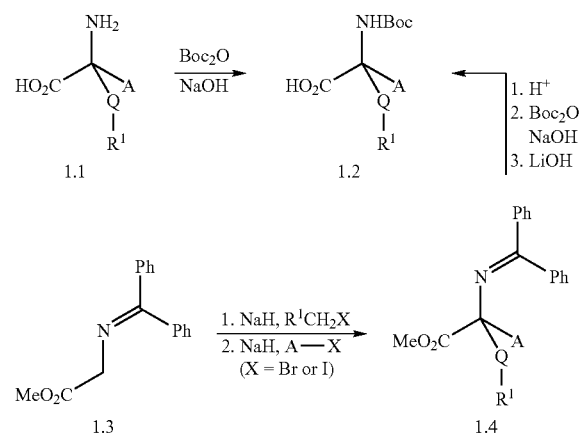

In Scheme 2, reduction of amino acid 1.1 with in-situ generated BH3 affords the corresponding amino alcohol, which can then be N-protected to afford compound 2.1. Oxidation of 2.1 affords aldehyde 2.2. Epoxidation of 2.2, followed by opening with ammonia affords amino alcohol 2.3.

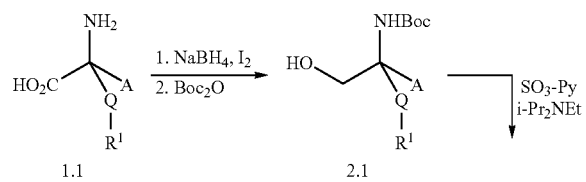

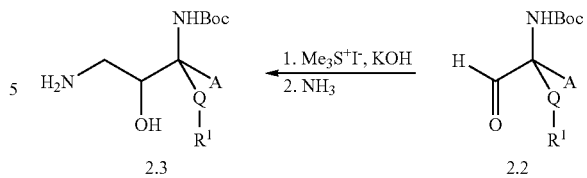

Scheme 3 outlines the synthesis of cyclopropylmethylamine derivatives ($NR^5R^6$) which are used in the following Schemes. Starting from cyclopropyl carboxylic acids of type 3.1, the benzyl amine 3.2 is generated via EDC coupling and borane reduction. Hydrogenation provides primary amine 3.3. Reductive methylation followed by hydrodenation leads to methyl amine 3.3. Further elaboration of 3.2 via amide coupling, borane reduction and hydrogenation of the benzyl group gives substituted amines of type 3.6 which are also used as coupling partners. Alternatively, reductive amination of 3.2 with various aldehydes followed by hydrogenation generates amines of type 3.7.

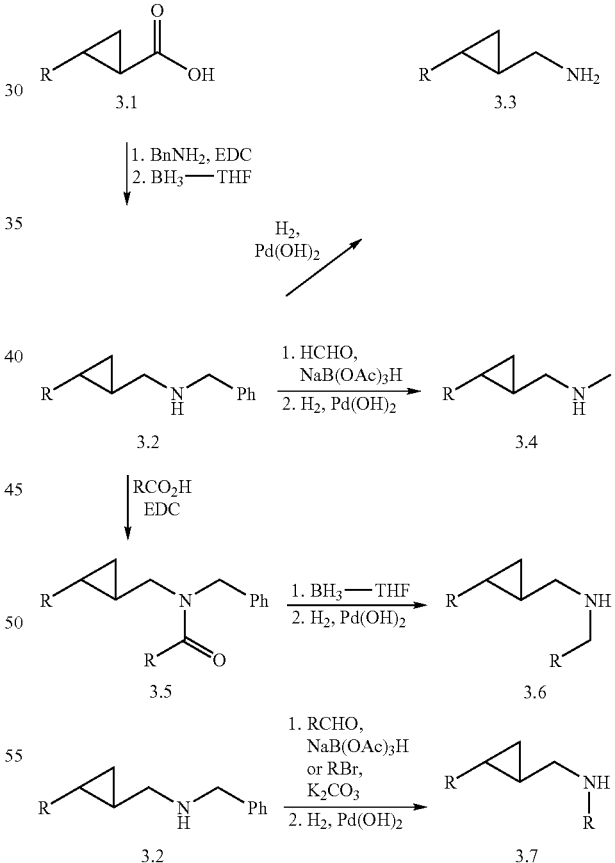

Scheme 4 describes the preparation of intermediates 4.2a-c and 4.3a-c, to be used in the elaboration of various heterocycles. While intermediates of type c have fully elaborated $R^7NSO_2R^4$ and $R^6R^5N$ moieties in place, intermediates of type a and b allow for introduction of those moieties after heterocycle elaboration.

Scheme 4
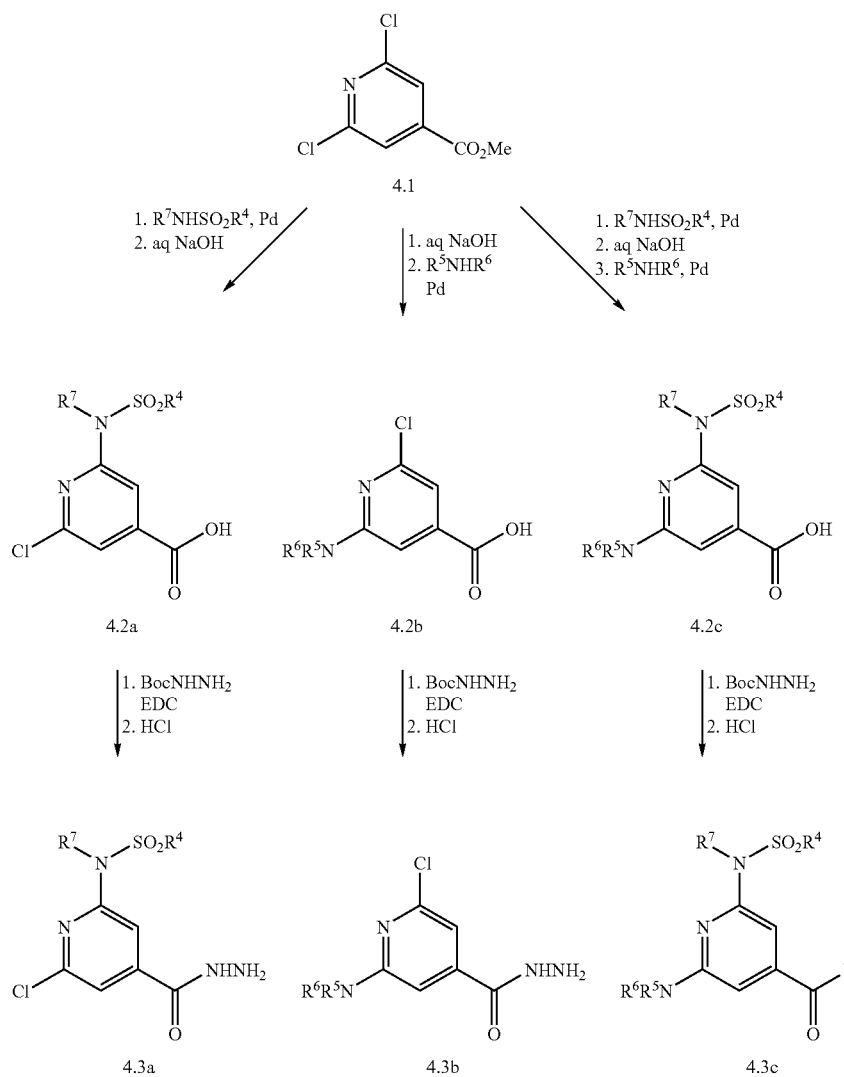
Scheme 5 describes the elaboration of oxadiazoles of type 5.1a-c and 5.2a-c by coupling of aminoacid derivatives of type 1.2 to acylhydrazides 4.3a-c followed by cyclodehydration with triphenylphosphine and carbon tetrabromide. Chlorides 5.1a,b are converted to 5.1c and then 5.2c via palladation and deprotection.
Scheme 5
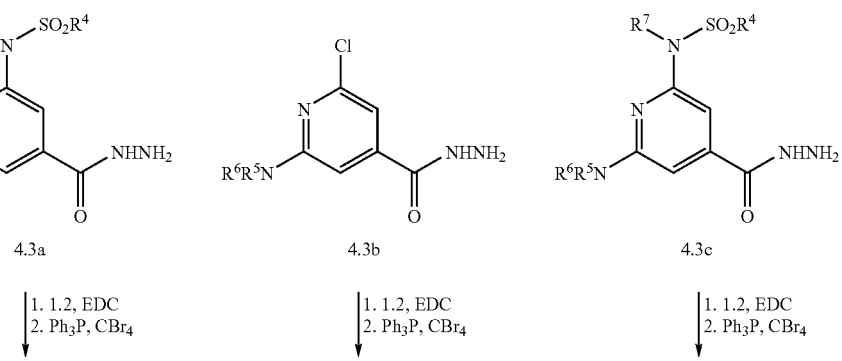

-continued
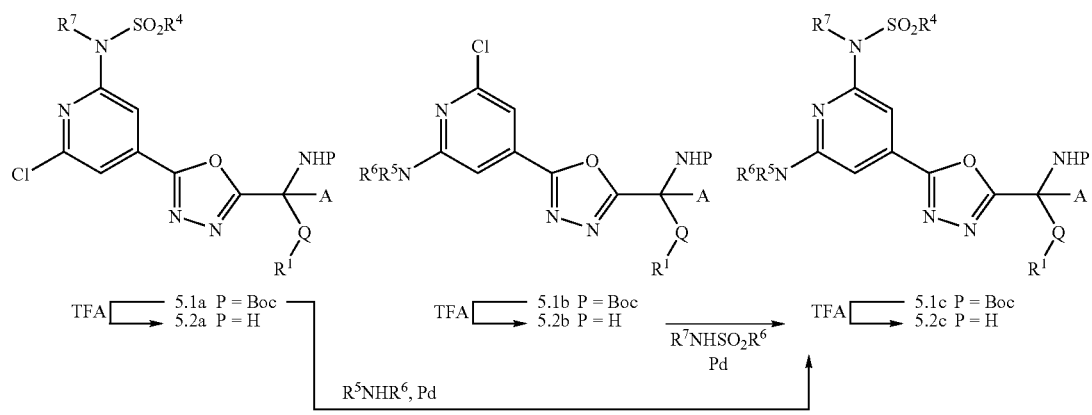
Scheme 6 describes the preparation of oxazoles of type 6.2: coupling of aminoalcohol 2.3 to acid 4.2, followed by oxidation to ketoamide 6.1 and cylodehydration.
Scheme 7 describes the preparation of furans of type 7.5
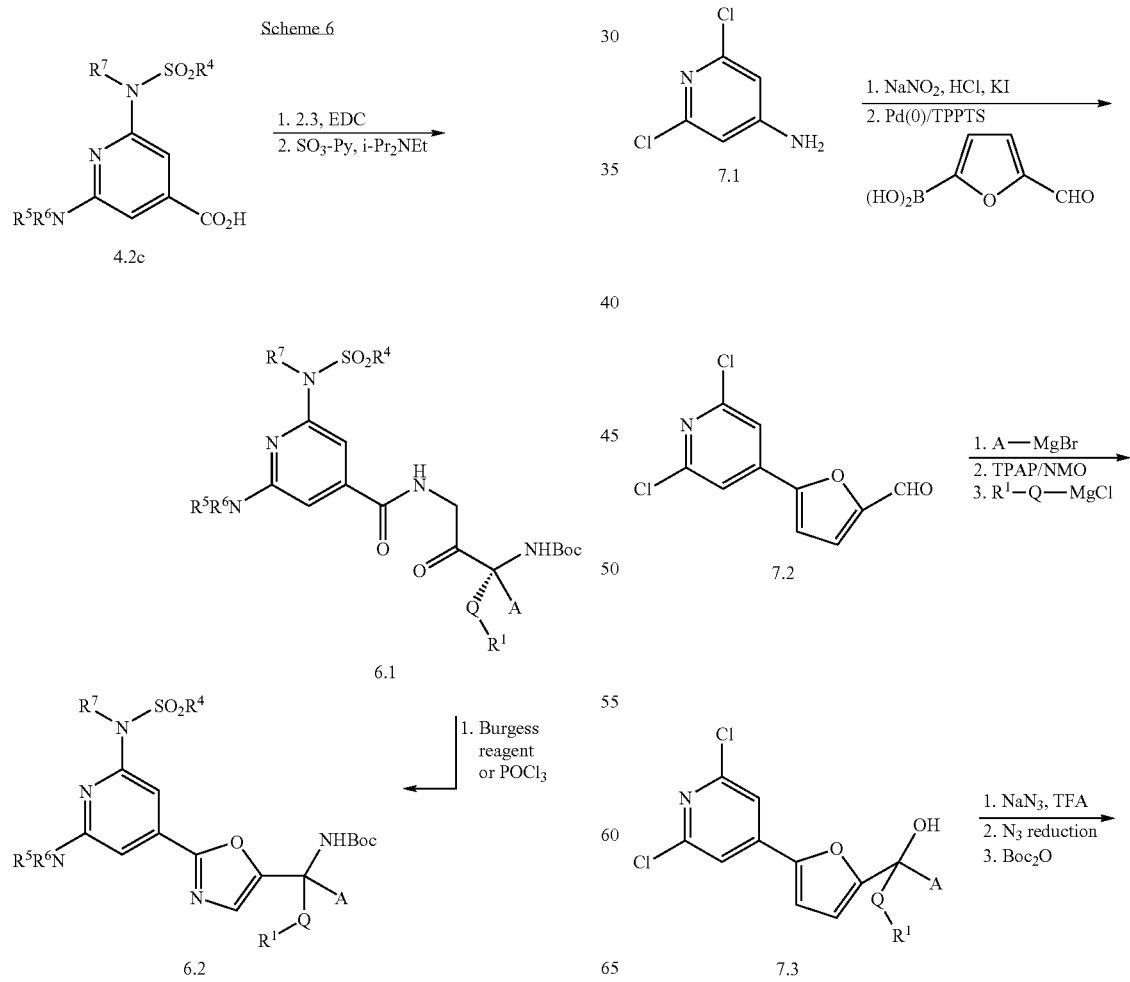

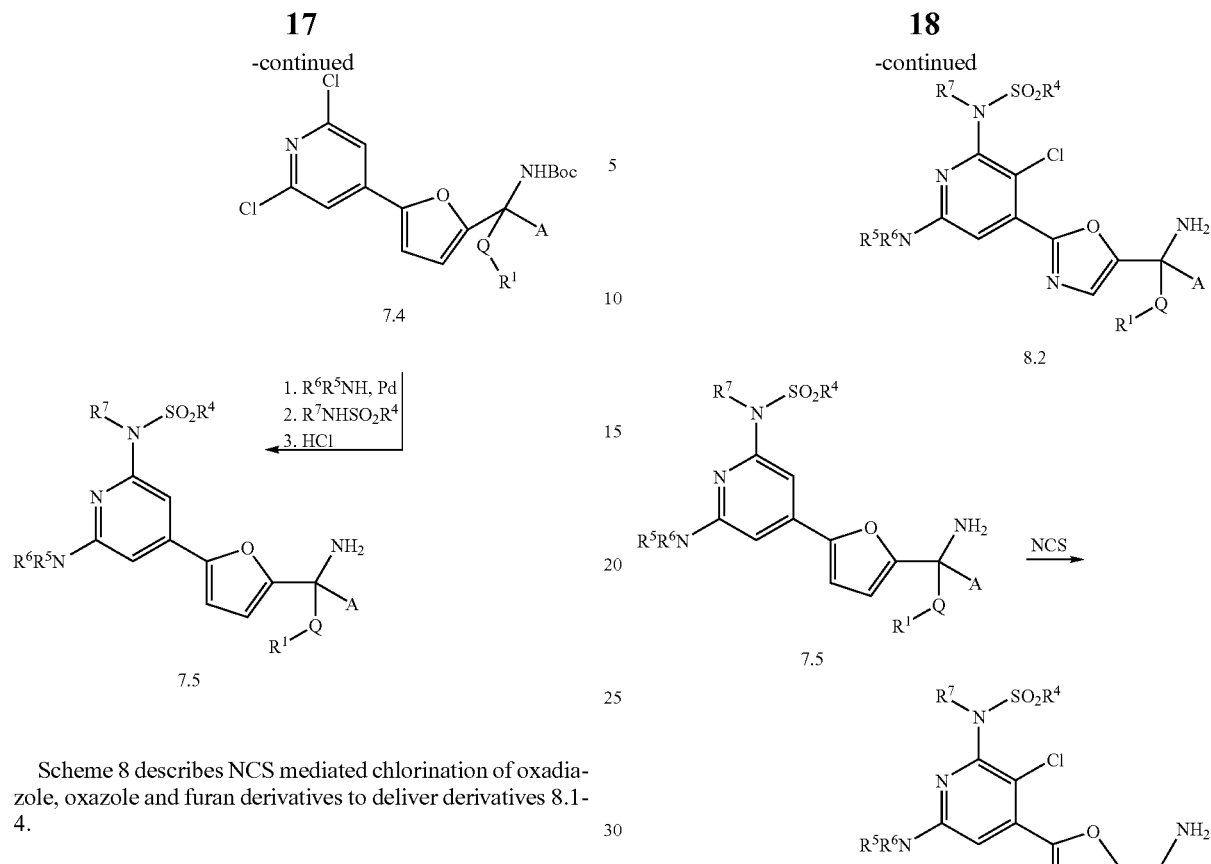

Scheme 8 describes NCS mediated chlorination of oxadiazole, oxazole and furan derivatives to deliver derivatives 8.1-4.

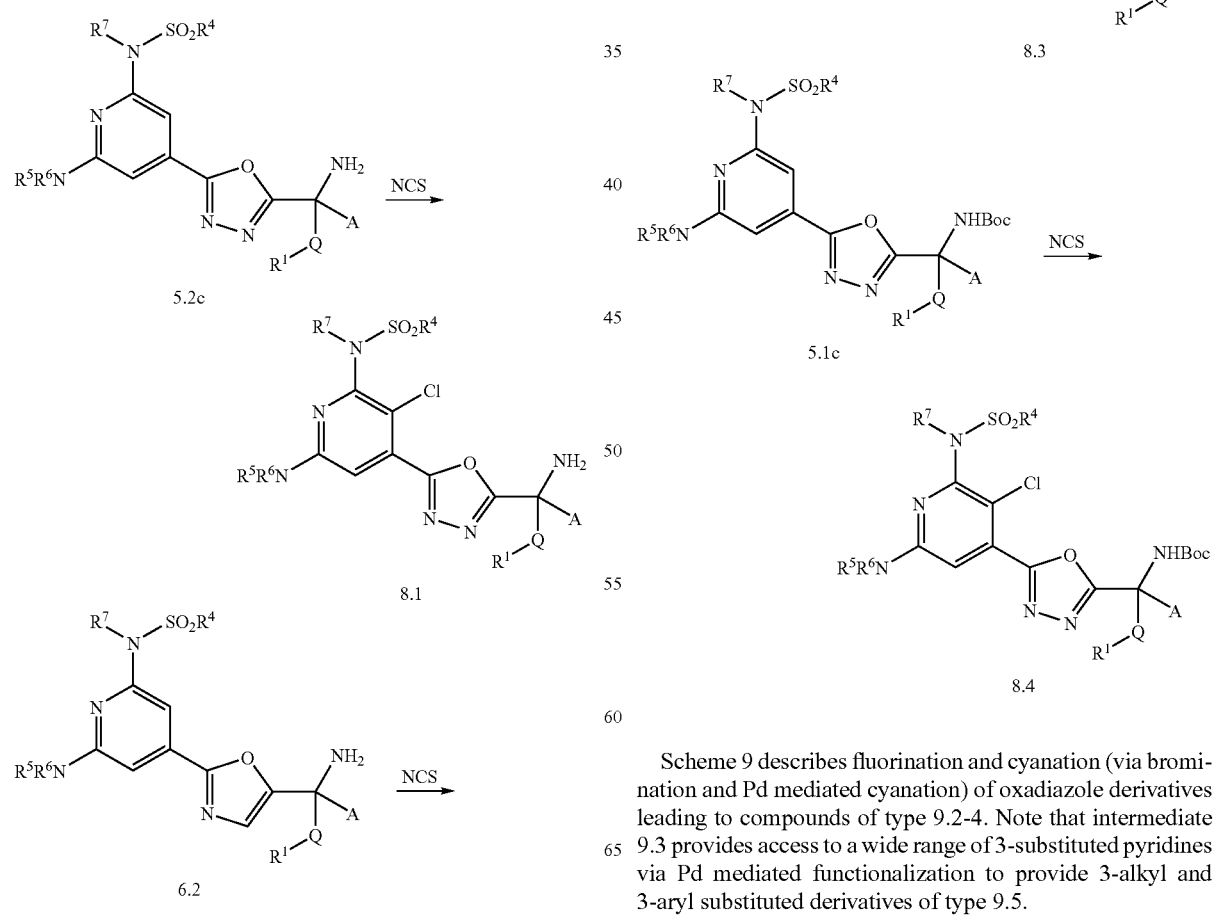

Scheme 9 describes fluorination and cyanation (via bromination and Pd mediated cyanation) of oxadiazole derivatives leading to compounds of type 9.2-4. Note that intermediate 9.3 provides access to a wide range of 3-substituted pyridines via Pd mediated functionalization to provide 3-alkyl and 3-aryl substituted derivatives of type 9.5.

Scheme 9
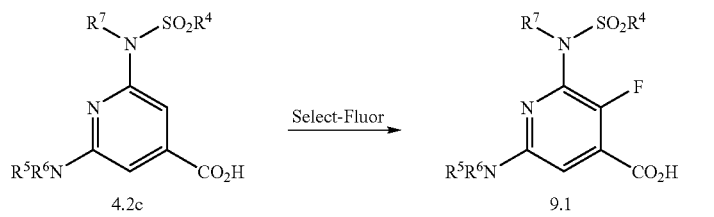
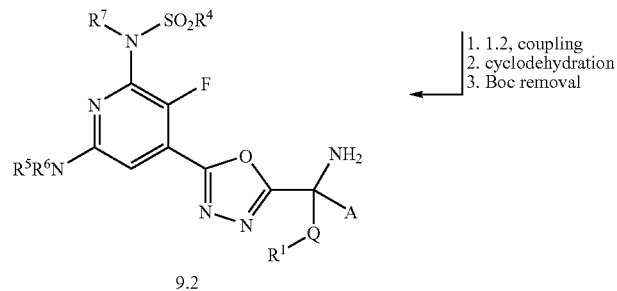
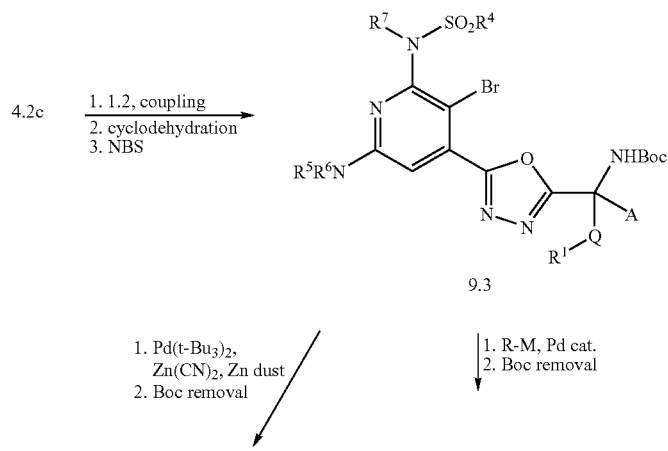
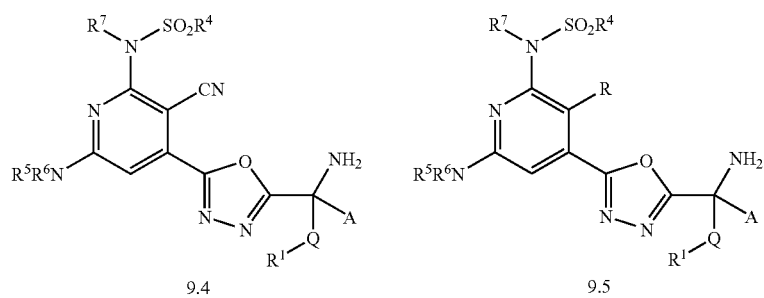

Scheme 10 describes the preparation of oxadiazole-Schiff base of type 10.2 that allows for late introduction of -Q-R₁ via alkylation.

Scheme 10

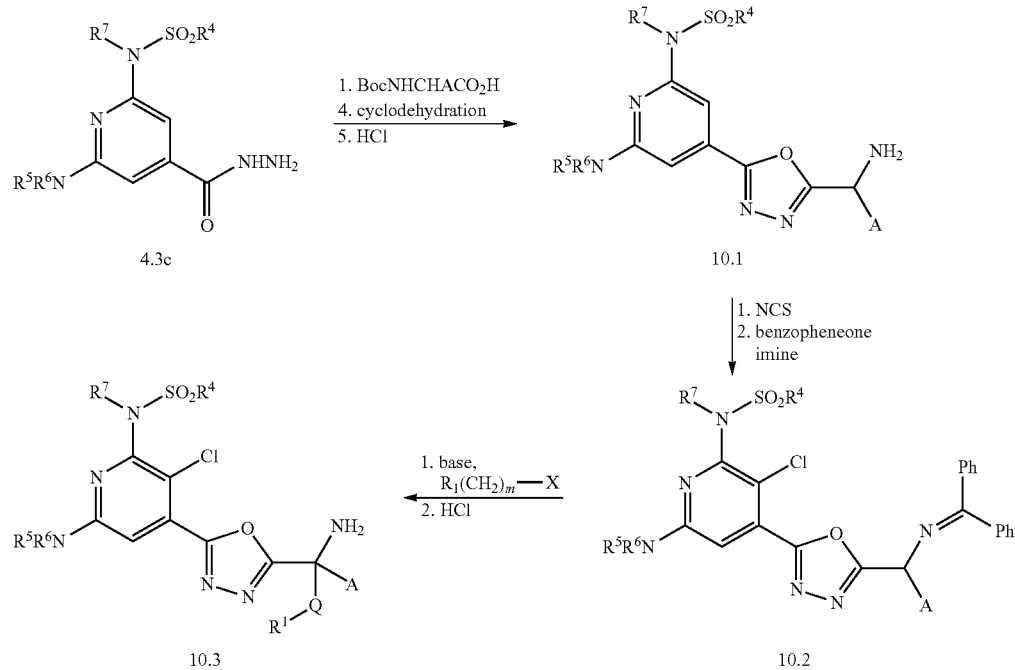

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; tau phpsphorylation inhibitors; M1 receptor positive allosteric modulators; blockers of Aβ oligomer formation; 5-HT modulators, such as PRX-03140, GSK 742467, SGS-518, FK-962, SL-65.0155, SRA-333 and xaliproden; p25/CDK5 inhibitors; NK1/NK3 receptor antagonists; COX-2 inhibitors; HMG-CoA reductase inhibitors; NSAIDs including ibuprofen; vitamin E; anti-amyloid antibodies, including anti-amyloid humanized monoclonal antibodies; anti-inflammatory compounds such as (R)-flurbiprofen, nitroflurbiprofen, rosiglitazone, ND-1251, VP-025, HT-0712 and EHT-202; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ antagonists such as ABT-834, ABT 829 and GSK 189254; AMPA agonists or AMPA modulators, such as CX-717, LY 451395 and S-18986; PDE IV inhibitors; GABAA inverse agonists; neuronal nicotinic agonists; selective M1 agonists; microtobubule affinity regulating kinase (MARK) ligands; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The compounds of the invention, like many protease inhibitors, are believed to be metabolized in vivo by cytochrome P-450 monooxygenase. Cytochrome P-450 is a family of isozymes which impact drug metabolism. Cytochrome P-450 isozymes (including the CYP3A4 isozyme) transform drug molecules in vivo, typically via oxidation. Metabolism by cytochrome P-450 often leads to unfavorable pharmacokinetics, and the need for more frequent and higher doses than are desirable. Administration of such drugs with an agent that inhibits metabolism by cytochrome P-450 may improve the pharmacokinetics (i.e., increase half-life, increase time to peak plasma concentration, increase blood levels) of the drug.

In one embodiment, the invention is directed to the combination or co-administration of a compound of the invention and a cytochrome P-450 inhibitor. The invention is also directed to a method for improving the pharmacokinetics of a compound of the invention which is metabolized by cytochrome P450 monooxygenase, by administering a compound of the invention with a cytochrome P-450 inhibitor.

The combination of a P-450 inhibitor and a compound of the invention may be administered as part of a unit dosage form combination product, or as a kit or treatment protocol wherein one or more p450 inhibitors are administered in separate dosage forms as part of a treatment regimen.

Exemplary p450 inhibitors include ketoconazole, clarithromycin, erythromycin, isoniazid, fluoxetine, midazolam, delavirdine, indinavir, ritonavir, dihydralazine, verapamil, troleandomycin, tamoxifen and irinotecan. Other p450 inhibitors are disclosed in Pea et al, *Clin Pharmacokinet* 2001, 40(11), 833-868; Zhou et al, *Current Drug Metabolism* 2004, 5, 415-442; and Wienkers, *J. Pharm Toxicol Methods* 2001, 45: 79-84. A preferred p450 inhibitor is ritonavir.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μL. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared starting from 100 μM with three fold series dilution) are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by ECL) are included in the reaction mixture (final DMSO concentration is 10%). All experiments are conducted at rt using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in one or both of the aforementioned assays, generally with an $IC_{50}$ from about 1 nM to 100 μM. Such a result is indicative of the intrinsic activity of the compounds in use as inhibitors of beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediate 1.2.1: N2-[(tert-butoxycarbonyl)amino]-2-methyl-3-pyridin-4-ylpropanoic acid
(Scheme 1)

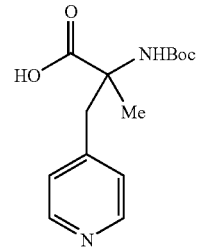

Step A: Schiff Base Formation

To a solution of alanine methyl ester hydrochloride (10.0 g, 71.6 mmol) in 100 mL $CH_2Cl_2$ was added benzophenone imine (12.0 mL, 71.6 mmol). A white ppt gradually came out of solution as the reaction was allowed to proceed at rt for 15 h. The reaction was diluted with $H_2O$ and $CH_2Cl_2$, and the layers were separate, the organic layer was washed with brine, dried over $Na_2SO_4$, filtered and concentrated to afford methyl-N-(diphenylmethylene)alaninate as a viscous oil which was used without further purification. $^1H$ NMR ($CDCl_3$, 400 MHz) δ 7.62 (m, 2H), 7.47-7.29 (m, 6H), 7.19-7.16 (m, 2H), 4.16 (q, J=6.8 Hz, 1H), 3.7 (s, 3H), 1.40 (d, J=6.8 Hz, 3H).

Step B: Alkylation

To a solution of methyl N-(diphenylmethylene)alaninate from Step A (9.78 g, 36.6 mmol) in 60 ml DMF at 0° C. was added a 1M solution of sodium bis(trimethylsilyl)amide in THF (45.72 ml, 45.72 mmol) over a 20 min period. After 30 min, a solution of 4-picolyl chloride hydrochloride (3.00 g, 18.29 mmol) in 40 ml DMF was added to the reaction via canula over a 25 min period. The reaction was warmed to rt and stirred for 5 h. The reaction was quenched with saturated aqueous $NH_4Cl$ and extracted with EtOAc (3×). The combined organic layers were washed with 3M LiCl (2×) and brine, dried over $Na_2SO_4$, filtered, and concentrated in vacuo. Purification by silica gel chromatography (0-40% EtOAc/hexanes) afforded methyl 2-[(diphenylmethylene)amino]-2-methyl-3-pyridin-4-ylpropanoate as a white solid (5.28 g, 81%). LCMS [M+H]=359.2. $^1H$ NMR ($d_4$-MeOH) δ 8.51 (dd, J=4.5, 1.5 Hz, 2H), 7.56 (dd, J=8.4, 1.4 Hz, 2H), 7.40-7.37 (m, 4H), 7.34-7.30 (m, 2H), 7.26-7.23 (m, 2H), 7.10-7.07 (m, 2H), 3.33 (A of AB, d, J=13.0 Hz, 1H), 3.27 (s, 3H), 3.18 (B of AB, d, J=12.9 Hz, 1H), 1.32 (s, 3H).

Step C: Removal of Schiff Base

To a suspension of methyl 2-[(diphenylmethylene)amino]-2-methyl-3-pyridin-4-ylpropanoate from Step B (5.28 g, 14.73 mmol) in 75 ml of 1:1 MeOH/THF was added 6N HCl (3.68 ml, 22.10 mmol). The reaction was concentrated in vacuo after stirring for 1.5 h at rt. Purification using ion exchange chromatography (SCX cartridge) afforded methyl 2-amino-2-methyl-3-pyridin-4-ylpropanoate as a yellow oil (2.76 g, 97%). LCMS [M+H]=195.3. $^1H$ NMR ($d_4$-MeOH) δ 8.43 (dd, J=4.6, 1.6 Hz, 2H), 7.24 (dd, J=4.6, 1.5 Hz, 2H), 3.70 (s, 3H), 3.09 (A of AB, d, J=12.9 Hz, 1H), 2.90 (1 of AB, d, J=13.0 Hz, 1H), 1.39 (s, 3H).

Step D: Boc Protection

To a suspension of methyl 2-amino-2-methyl-3-pyridin-4-ylpropanoate from Step C (2.76 g, 14.21 mmol) in 70 ml THF at 0° C. was added di-tert-butyl dicarbonate (4.03 g, 18.47 mmol). After 30 min, the reaction was warmed to rt and allowed to proceed over night. The reaction was diluted with EtOAc and washed with saturated aqueous $NH_4Cl$, water, and brine. The organic layer was dried over $Na_2SO_4$, filtered, and concentrated in vacuo. Purification on silica gel chromatography (0-60% $EtOAc/CH_2Cl_2$) afforded methyl 2-[(tert-butoxycarbonyl)amino]-2-methyl-3-pryidin-4-ylpropanoate as a yellow solid (3.22 g, 77%). LCMS [M+H]=295.2. $^1H$ NMR (400 MHz, $d_4$-MeOH) δ 8.43 (d, J=5.1 Hz, 2H), 7.21 (d, J=5.9 Hz, 2H), 3.73 (s, 3H), 3.44 (A of AB, d, J=13.2 Hz, 1H), 3.12 (B of AB, d, J=13.2 Hz, 1H), 1.46 (s, 9H), 1.30 (s, 3H).

Step E: Saponification

To a solution of methyl 2-[(tert-butoxycarbonyl)amino]-2-methyl-3-pryidin-4-ylpropanoate from Step D (0.25 g, 0.85 mmol) in 4.25 ml of 1:1 MeOH/THF was added 3N NaOH (0.43 ml, 1.27 mmol). The reaction was allowed to proceed at 50° C. for 1 h, at which point it was cooled to rt and quenched with 6N HCl (0.21 ml, 1.27 mmol). The reaction was concentrated in vacuo to yield 2-[(tert-butoxycarbonyl)amino]-2-methyl-3-pyridin-4-ylpropanoic acid NaCl as a white solid. LCMS [M+H]=281.3. $^1H$ NMR (400 MHz, $d_4$-MeOH) δ 8.44 (d, J=5.3 Hz, 2H), 7.28 (d, J=5.9 Hz, 2H), 3.43 (A of AB, d, J=12.6 Hz, 1H), 3.33 (B of AB, d, J=12.3 Hz, 1H), 1.47 (s, 9H), 1.41 (s, 3H).

Intermediate 1.2.2:
N-(tert-butoxycarbonyl)-2,5-dimethylnorleucine
(Scheme 1)

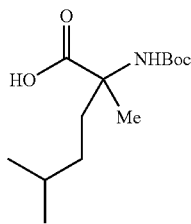 [SMILES: CC(C)CCC(C)(NC(=O)OC(C)(C)C)C(=O)O]

N-(tert-butoxycarbonyl)-2,5-dimethylnorleucine was prepared from isobutyl iodide and the alanine Schiff base as described for the preparation of intermediate 1.2.1

Intermediate 2.3.1: tert-butyl (3R-amino-1-benzyl-2RS-hydroxy-1-methylpropyl)carbamate (Scheme 2)

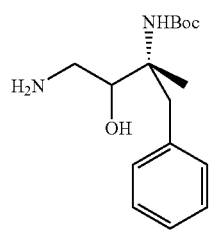

Step A: Reduction

To a solution of D-alpha-methyl-phenylalanine (1.74 g, 9.71 mmol) in 30 mL THF at rt was added $NaBH_4$ (0.92 g 24.27 mmol) in one portion. The solution was cooled to 0° C. Iodine (2.46 g, 9.71 mmol) in 5 mL THF was added dropwise over 30 min. After the addition was complete, the reaction was heated to reflux for 2 days. The reaction was then cooled to 0° C. and quenched by the addition of methanol until the bubbling subsided. The reaction mixture was acidified by the addition of 6N HCl until pH 1, stirred at 50° C. for 30 min and concentrated in vacuo. Purification using ion exchange chromatography (SCX cartridge) afforded 2R-amino-2-methyl-3-phenylpropan-1-ol as a white solid. $^1H$ NMR (400 MHz, $CDCl_3$) δ 7.35-7.18 (m, 5H), 3.36 (A of AB, d, J=10.4 Hz, 1H), 3.31 (B of AB, d, J=10.4 Hz, 1H), 2.70 (s, 2H), 1.04 (s, 3H).

Step B: Boc Protection

A solution of 2R-amino-2-methyl-3-phenylpropan-1-ol (4.14 g, 25 mmol) and ditertbutyldicarbonate (7.1 g, 32.5 mmol) was stirred at rt for 16 h, concentrated in to provide tert-butyl (1-benzyl-2R-hydroxy-1-methylethyl)carbamate), as a white solid. $^1H$ NMR (400 MHz, $CDCl_3$) δ 7.35-7.15 (m, 5H), 4.48 (br s, 1H), 4.17 (br s, 1H), 3.76-3.62 (m, 2H), 3.19 (A of AB, d, J=13.6 Hz, 1H), 2.81 (B of AB, d, J=13.6 Hz, 1H), 1.47 (s, 9H), 1.07 (s, 3H).

Step C: Oxidation

To a solution of tert-butyl (1-benzyl-2R-hydroxy-1-methylethyl)carbamate (6.7 g, 25.2 mmol) in DCM (100 mL) and DMSO (25 mL) was added triethylamine (10.5 mL, 75.7 mmol) and sulfurtrioxide-pyridine (10 g, 63.1 mmol). The reaction mixture was stirred at rt for 3.5 h, diluted with EtOAc, washed with 10% $KHSO_4$, saturated $NaHCO_3$, water, brine and aq LiCl, dried over sodium sulfate, concentrated in vacuo and purified by flash chromatography (silica, 0-20% EtOAc/hexanes) to provide tert-butyl (1-benzyl-1-methyl-2R-oxoethyl)carbamate as a white solid. $^1H$ NMR (400 MHz, $CDCl_3$) δ 9.53 (s, 1H), 7.35-7.22 (m, 3H), 7.12-7.00 (m, 2H), 4.84 (br s, 1H), 3.17 (A of AB, d, J=13.6 Hz, 1H), 3.08 (13 of AB, d, J=13.6 Hz, 1H), 1.51 (s, 9H), 1.27 (s, 3H).

Step D: Epoxidation

To a solution of N-(tert-butyl (1-benzyl-1-methyl-2R-oxoethyl)carbamate (1 g, 3.80 mmol) in acetonitrile (15 mL) was added 6 drops water, trimethylsulfonium iodide (775 mg, 3.80 mmol) and potassium hydroxide (511 mg, 9.11 mmol). The reaction was stirred at 60° C., sealed, for 1.5 h, additional trimethylsulfonium iodide (775 mg, 3.80 mmol) and potassium hydroxide (511 mg, 9.11 mmol) were added and the reaction was stirred at 60° C., sealed, for 3 h. The reaction mixture was diluted with EtOAc, washed with sat'd aq $NaHCO_3$, brine, dried over sodium sulfate, and concentrated in vacuo to provide tert-butyl (1-methyl-1-oxiran-2R-yl-2-phenylethyl)carbamate as an oil. MS (ES, M+H) 278.

Step E: Epoxide Opening

A solution of tert-butyl (1-methyl-1-oxiran-2R-yl-2-phenylethyl)carbamate (986 mg, 3.56 mmol) in EtOH (35 mL) and $NH_4OH$ (35 mL) was stirred at 60° C., sealed, for 16 h, concentrated in vacuo and purified by flash chromatography (silica, 0-30% (10% $NH_4OH/MeOH)/CH_2Cl_2$) to provide tert-butyl (3R-amino-1-benzyl-2-RS-hydroxy-1-methylpropyl)carbamate as a thick oil. $^1H$ NMR (400 MHz, $CD_3OD$, 1:1 diastereomeric mixture) δ 7.30-7.14 (m, 5H), 4.01 (br d, J=9.2 Hz, 0.5H), 3.54 (dd, J=10.0, 2 Hz, 0.5H), 3.39 (br s, 0.5H), 3.36 (br s, 0.5H), 2.94-2.56 (m, 4H), 1.47 (s, 9H), 1.03 (s, 1.5H), 0.99 (s, 1.5H).

Intermediate 3.2.1:
N-benzyl-1-(2-trans-methylcyclopropyl)methanamine
(Scheme 3)

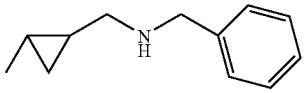

Step A: Coupling

To a solution of 2-methylcyclopropanecarboxylic acid (77.74 g, 777 mmol), benzyl amine (93.3 mL, 854 mmol) and DIPEA (141.5 mL, 854 mmol) were dissolved in 1200 mL of dichloromethane. To this solution at rt EDC-HCl (163.7 g, 854 mmol) was added as a solid portionwise and stirred overnight. The reaction mixture was poured onto 0.3M HCl. The layers were separated and washed once again with 0.3M HCl and satd. aqueous NaHCO$_3$. The organic layer was subsequently washed with H$_2$O, followed by brine, dried over Na$_2$SO$_4$ and the residue was recrystallized from EtOAc/hexanes to afford the coupled adduct as white crystals: $^1$H NMR (400 MHz, CDCl$_3$) δ 7.28 (m, 5H), 5.81 (br s, 1H), 4.43 (dd, J=5.6, 2.4 Hz, 2H), 1.37 (m, 1H), 1.17 (m, 1H), 1.07 (d, J=6.0 Hz, 3H), 1.04 (overlapping m, 1H), 0.56 (m, 1H).

Preparative chiral HPLC is optionally performed to afford the preferred enantiomer trans-S,S. In the following intermediates and examples, either the preferred enantiomer trans-S,S or the racemic mixture trans-S,S and trais-R,R were used without discrimination. For simplification, the methyl-cyclopropyl-methyl moiety is drawn as trans-racemic.

Step B: Reduction

A 500 mL flask charged with N-benzyl-trans-2-methylcyclopropanecarboxamide (from step B, 3.9 g, 20.6 mmol) in THF (801 mL). BH$_3$-THF (1.0 M, 105 mL, 105 mmol) was added dropwise via an addition funnel. Upon complete addition (10 min.) the mixture was refluxed for 5 h. The mixture was allowed to cool to rt and quenched carefully with MeOH (15 mL). The mixture was concentrated to dryness, dissolved in dichloromethane and washed with 3M KOH. The organic layer was isolated, washed with brine, then dried over Na$_2$SO$_4$ and concentrated to dryness. The crude material was treated with 1N HCl in dioxane for 1 h at 50° C. The mixture was concentrated to give hydrochloride salt as a white solid. The solid was dissolved in sat. aq. NaHCO$_3$ (80 mL) and extracted with CHCl$_3$ (2×150 mL). The combined organic layers were washed with brine, dried over Na$_2$SO$_4$ and the solvent removed via rotorary evaporation to give after drying in vacuo N-benzyl-1-(2-trans-methylcyclopropyl)methanamine as an off-white semi-solid (quant.): $^1$H NMR (400 MHz, CDCl$_3$) δ 7.28 (m, 5H), 3.80 (s, 2H), 2.50 (d, J=6.8 Hz, 2H), 2.4 (br s, 1H), 1.02 (d, J=6.0 Hz, 3H), 0.69 (m, 1H), 0.52 (m, 1H), 0.23 (m, 2H).

Intermediate 3.3.1:
N-methyl-1-(2-trans-methylcyclopropyl)methanamine
(Scheme 3)

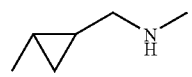

To a solution of N-benzyl-1-(2-trans-methylcyclopropyl) methenamine (8 g, 45.6 mmol, intermediate VI) in DCE (240 mL) and MeOH (120 mL) was added formaldehyde (34 mL, 456 mmol, 37% aqueous) and NaBH(OAc)$_3$ (19.3 g, 91 mmol). The reaction mixture was stirred at rt for 1 h, treated with sat'd aq NaHCO$_3$, concentrated near dryness, diluted with water and extracted with EtOAc (3×). The combined organic layer was washed with brine, dried over sodium sulfate, treated with HCl (50 mL, 50 mmol, 1M Et$_2$O), and concentrated in vacuo to afford N-benzyl-methyl-1-(2-trans-methylcyclopropyl)methanamine as the hydrochloride which was hydrogenated in the presence of 20% Pd(OH)$_2$/C (616 mg), in EtOH (400 mL), at 60° C., under 1 atm H$_2$ for 2 h. Filtration and concentration in vacuo provided N-methyl-1-(2-trans-methylcyclopropyl)methanamine as the hydrochloride. $^1$H NMR (400 MHz, CD$_3$OD) δ 2.88 (d, J=7.3 Hz, 2H), 2.69 (s, 3H), 1.09 (d, J=5.7 Hz, 3H), 0.78-0.70 (m, 2H), 0.52-0.50 (m, 1H), 0.50-0.40 (m, 1H).

Intermediate 3.4.1:
2-trans-methylcyclopropyl)methanamine (Scheme 3)

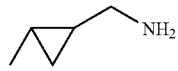

To a solution of N-benzyl-1-(2-trans-methylcyclopropyl) methanamine (intermediate 3.2.1, 255 mg, 1.46 mmol) in EtOH (20 mL) was added 1N HCl (1.53 mL, 1.53 mmol). The solution was degassed with argon and Pd(OH)$_2$ was added (30 mg). The reaction mixture was stirred at 60° C. under 1 atm of hydrogen for 16 h. Filtration on cellite and concentration provided 2-trans-methylcyclopropyl)methanamine as the hydrochloride. $^1$H NMR (400 MHz, CD$_3$OD+CDCl$_3$) δ 2.90-2.60 (m, 2H), 1.09 (bs, 3H), 0.90-0.70 (m, 2H), 0.60-0.35 (m, 2H).

Intermediate 3.6.1:
(2-methoxyethyl)[(2-methylcyclopropyl)methyl]amine
(Scheme 3)

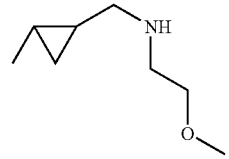

Step A: Coupling

To a solution of N-benzyl-1-(2-trans-methylcyclopropyl) methanamine hydrochloride (intermediate 3.2.1, 10 g, 47.2 mmol) in CHCl$_3$ (150 mL) was added diisopropylethyl amine (9.87 mL, 56.7 mmol), methoxyacetic acid (4.35 mL, 56.7 mmol), HOAt (1.29 g, 9.5 mmol) and EDC (10.87 g, 56.7 mmol), and the reaction mixture was stirred at rt for 18 h. The reaction mixture was concentrated in vacuo, diluted with EtOAc, washed with 10% KHSO$_4$, aq NaHCO$_3$ and brine, dried over sodium sulfate and concentrated in vacuo to give trans N-benzyl-2-methoxy-N-[(2-methylcyclopropyl)methyl]acetamide which was used as is in the next step.

Step B: Reduction

To a solution of trans N-benzyl-2-methoxy-N-[(2-methylcyclopropyl)methyl]acetamide (12.18 g, 49.2 mmol) in THF (100 mL) cooled to 0° C. was slowly added borane-THF (123.1 mL, 123.1 mmol, 1M THF). The reaction mixture was stirred at 70° C. for 2 h. The reaction mixture was cooled to 0° C. and carefully quenched with MeOH. Additional MeOH (20 mL) was added and the resulting mixture was stirred at reflux for 0.5 h. After concentration in vacuo to ca. 200 mL, HCl (g) saturated MeOH (25 mL) was added and the mixture stirred at 50° C. for 1 h. Additional HCl (g) saturated MeOH (25 mL) was added and the mixture stirred at 50° C. for 1 h. The reaction mixture was concentrated in vacuo, reconcentrated from EtOH, MeOH, and DCM several times to afford trans N-benzyl-2-methoxy-N-[(2-methylcyclopropyl)methyl]ethanamine hydrochloride as a colorless thick oil, used as is in the next step.

Step C: Hydrogenation

To a solution of trans N-benzyl-2-methoxy-N-[(2-methylcyclopropyl)methyl]ethanamine hydrochloride (16 g, 59.3 mmol) in EtOH (400 mL), degassed with Argon, was added Pd(OH)$_2$ (830 mg, 20%), and the mixture was stirred under 1 atm H$_2$, at room temperature for 4 h. The reaction mixture was purged with N$_2$, filtered on celite, under N$_2$, concentrated in vacuo, and dried under vacuum over P$_2$O$_5$ to give trans (2-methoxyethyl)[(2-methylcyclopropyl)methyl]amine hydrochloride as a white foam. $^1$H NMR (400 MHz, CDCl$_3$) δ 9.46 (bs, 2H), 3.84 (t, J=5.1 Hz, 2H), 3.40 (s, 3H), 3.23 (bt, J=5.1 Hz, 2H), 3.08-2.88 (m, 2H), 1.09 (d, J=6.1 Hz, 3H), 1.02-0.91 (m, 1H), 0.86-0.78 (m, 1H), 0.65-0.57 (m, 1H), 0.50-0.42 (m, 1H).

Intermediate 3.6.2: (2,2-difluoroethyl)[(2-methylcyclopropyl)methyl]amine

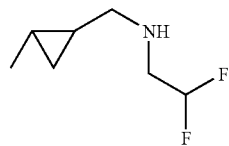

Prepared from N-benzyl-1-(2-trans-methylcyclopropyl)methanamine hydrochloride and difluoroacetic acid using a similar procedure as described in the preparation of intermediate 3.6.1. $^1$H NMR (400 MHz, CD$_3$OD) δ 6.35 (tt, 48, 3 Hz, 1H), 3.56 (td, J=15.6, 3.1 Hz, 2H), 3.03 (m, 2H), 1.11 (d, J=5.9 Hz, 3H), 0.83 (m, 2H), 0.60 (m, 1H), 0.50 (m, 1H).

Intermediate 3.6.3: (2-{[tert-butyl(dimethyl)silyl]oxy}ethyl)[(2-methylcyclopropyl)-methyl]amine

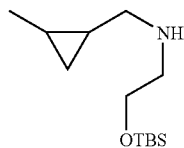

Prepared from (tert-butyl(dimethyl)silyloxy)ethyl amine and 2-methylcyclopropane carboxylic acid using a similar procedure as described for Intermediate 3.2.1. $^1$H NMR (400 MHz, CD$_3$OD) δ 3.74 (t, J=5.3 Hz, 2H), 2.76 (m, 2H), 2.52 (m, 2H), 1.04 (d, J=6.0 Hz, 3H), 0.90 (s, 9H), 0.68 (m, 1H), 0.55 (m, 1H), 0.29 (m, 1H), 0.24 (m, 1H), 0.07 (s, 6H).

Intermediate 3.6.4: {(1S)-[(1S,2)-2-methylcyclopropyl]ethyl}amine

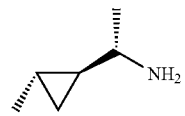

Step A. (2E)-1,1-diethoxybut-2-ene

Crotonaldehyde (23.64 mL, 285.35 mmol), triethyl orthoformate (57.02 mL, 342.42 mmol) and ammonium nitrate (2.28 g, 28.54 mmol) were combined in 60 mL EtOH. After 22 h at ambient temperature, the reaction was diluted with EtOAc (60 mL) and washed with saturated sodium bicarbonate solution (40 mL). The aqueous layer was back extracted with EtOAc (20 mL). The combined organics were washed with brine (40 mL), dried over Na$_2$SO$_4$, filtered and concentrated in vacuo to give 36.5 g (89%) of 1,1-diethoxybut-2-ene. $^1$H NMR (CDCl$_3$, 400 MHz) 5.84 (m, 1H); 5.54 (m, 1H); 4.82 (d, J=5.7 Hz, 1H); 3.64 (m, 2H); 3.49 (m, 2H); 1.73 (m, 3H); 1.21 (m, 6H).

Step B. Diisopropyl (4S,5S)-2-[(1E)-prop-1-enyl]-1,3-dioxolane-4,5-dicarboxylate A solution of (2E)-1,1-diethoxybut-2-ene (32.20 g, 223.27 mmol), (−)-diisopropyl D-tartrate (64.64 mL, 245.60 mmol) and pyridinium tosylate (2.24 g, 8.93 mmol) in 100 mL benzene was heated to 95° C. to distill off the solvent and EtOH produced. After 7 h at 95° C., the reaction was cooled to rt and concentrated in vacuo. Purification by normal phase chromatography (10->30% EtOAc/hexanes) yielded 35.37 g (55%) of diisopropyl (4S,5S)-2-[(1E)-prop-1-enyl]-1,3-dioxolane-4,5-dicarboxylate as an orange oil. $^1$H NMR (CDCl$_3$, 400 MHz) 6.03 (m, 1H); 5.86 (m, 2H); 5.12 (m, 2H); 4.71 (d, J=3.84 Hz, 1H); 4.63 (d, J=3.84 Hz, 1H); 1.78 (m, 3H); 1.30 (d, J=6.23 Hz, 12H); LC/MS [M+H]$^+$=287.

Step C. Diisopropyl (4S,5S)-2-[(1S,2S)-2-methylcyclopropyl]-1,3-dioxolane-4,5-dicarboxylate To a −20° C. solution of intermediate diisopropyl (4S,5S)-2-[(1E)-prop-1-enyl]-1,3-dioxolane-4,5-dicarboxylate (4.10 g, 14.32 mmol) in 60 mL hexanes was added IM diethylzinc in hexanes (42.96 mL, 42.96 mmol). Diiodomethane (6.92 mL, 85.92 mmol) was added dropwise with vigorous stirring. After 1 h at −20° C., the reaction was refrigerated at −5° C. After 17 h at −5° C., the reaction was stirred at 0° C. for an additional 5 h and then quenched with cold saturated ammonium chloride solution (100 mL) and extracted with Et$_2$O (100 mL×3). The combined organics were washed w/aqueous sodium thiosulfate (100 mL) and brine (100 mL), filtered, dried over Na$_2$SO$_4$, filtered again and concentrated in vacuo. Purification by normal phase chromatography (10->30% EtOAc/hexanes) yielded 3.85 g (89%) of diisopropyl (4S, 5S)-2-[(1S,2S)-2-methylcyclopropyl]-1,3-dioxolane-4,5-dicarboxylate as a yellow oil. $^1$H NMR (CDCl$_3$, 400 MHz) 5.12 (m, 2H); 4.78 (d, J=6.41 Hz, 1H); 4.66 (d, J=4.21 Hz, 1H); 4.57 (d, J=4.22 Hz, 1H); 1.30 (m, 12H); 1.09 (d, J=5.68 Hz, 3H); 0.94 (m, 2H); 0.67 (m, 1H); 0.39 (m, 1H); LC/MS [M+H]$^+$=301.

Step D. 2-methyl-N-{(1E)-[(1S,2S)-2-methylcyclopropyl]methylidene}propane-2-sulfinamide To a solution of diisopropyl (4S,5S)-2-[(1S,2S)-2-methylcyclopropyl]-1,3-dioxolane-4,5-dicarboxylate (0.450 g, 1.50 mmol) in 5 mL CH$_2$Cl$_2$/200 uL H$_2$O was added p-toluenesulfonic acid (0.071 g, 0.38 mmol). Reaction heated to reflux at 50° C. After 16 h at 50° C., the reaction was cooled to rt. Water droplets sitting at the top of the reaction were removed. Copper (II) sulfate (0.507 g, 2.85 mmol) and R-(+)-tert-butanesulfinamide (0.173 g, 1.43 mmol) were added. After 5.5 h at ambient temperature, the reaction was filtered over a pad of celite. The celite was washed with CH$_2$Cl$_2$ (200 mL) and the filtrate concentrated in vacuo. Purification by normal phase chromatography (0->50% EtOAc/hexanes) yielded 0.245 g (92%) of 2-methyl-N-{(1E)-[(1S,2S)-2-methylcyclopropyl]methylidene}propane-2-sulfinamide as a clear, colorless residue. $^1$H NMR (CDCl$_3$, 400 MHz) 7.46 (d, J=7.69 Hz, 11H); 1.62 (m, 11H); 1.25 (m, 2H); 1.10 (m, 12H); 0.82 (m, 1H); LC/MS [M+H]$^+$=188.

Step E. 2-methyl-N-{(1S)-1-[(1S,2S)-2-methylcyclopropyl]ethyl}propane-2-sulfinamide To a −78° C. solution of 2-methyl-N-{(1E)-[(1S,2S)-2-methylcyclopropyl]methylidene}propane-2-sulfinamide (0.300 g, 1.60 mmol) in 5 mL CH$_2$Cl$_2$ was added 3M methylmagnesium bromide in Et$_2$O (1.07 mL, 3.20 mmol). After 2 h at −78° C., the reaction was warmed to rt. After 1 h at ambient temperature, the reaction was quenched with saturated ammonium chloride solution (15 mL) and extracted with EtOAc (30 mL×2). The combined organics were washed with brine (15 mL), dried over Na$_2$SO$_4$, filtered and concentrated in vacuo. Purification by normal phase chromatography (0->80% EtOAc/hexanes) yielded 0.224 g (69%) of -methyl-N-{(1S)-1-[(1S,2S)-2-methylcyclopropyl]ethyl}propane-2-sulfinamide as a clear, colorless residue. $^1$H NMR (CDCl$_3$, 400 MHz) 2.77 (m, 1H); 1.31 (d, J=6.50 Hz, 3H); 1.21 (s, 9H); 1.03 (d, J=5.77 Hz, 3H); 0.54 (m, 3H); 0.30 (m, 1H); LC/MS [M+H]$^+$=204.

Step F. (1S)-1-[(1S,2S)-2-methylcyclopropyl]ethanaminium chloride

To a 0° C. solution of 2-methyl-N-{(1S)-1-[(1S,2S)-2-methylcyclopropyl]ethyl}propane-2-sulfinamide (0.210 g, 1.03 mmol) in 4 mL MeOH was added 2M HCl in Et$_2$O (0.52 mL, 1.03 mmol). Reaction stirred from 0° C. to rt over 18 h and then concentrated in vacuo. The resulting material was taken up in Et$_2$O (4 mL) and concentrated in vacuo twice to give (1S)-1-[(1S,2S)-2-methylcyclopropyl]ethanaminium chloride as a white solid. $^1$H NMR (CDCl$_3$, 400 MHz) 2.60 (m, 1H); 1.37 (d, J=6.59 Hz, 3H); 1.08 (d, J=6.04 Hz, 3H); 0.77 (m, 1H); 0.64 (m, 2H); 0.42 (m, 1H); LC/MS [M+H]$^+$=100.

Intermediate 3.6.5: {(1R)-1-[(1S,2S)-2-methylcyclopropyl]ethyl}amine

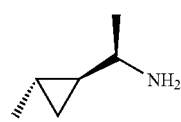

Prepared using protocol as described for intermediate 3.6.4, with the modification of S-(+)-tert-butanesulfinamide being used in step D. LC/MS [M+H]$^+$=100.

Intermediate 3.6.6: (2-methoxyethyl)[(2-methylcyclopropyl)methyl]amine

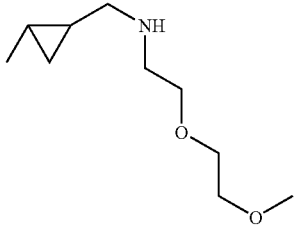

Prepared from 2-(2-methoxyethoxy)ethanamine and trans-2-methylcyclopropanecarboxylic acid using steps A and B in the procedure described for the synthesis of Intermediate 3.6.1.

Intermediate 3.6.7: (2-methoxyethyl)[(2-methylcyclopropyl)methyl]amine

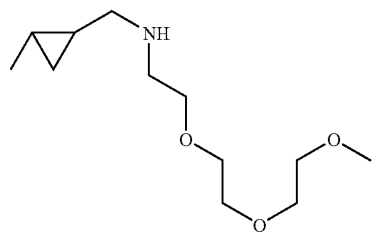

Prepared from 2-[2-(2-methoxyethoxy)ethoxy]ethanamine and trans-2-methylcyclopropanecarboxylic acid using steps A and B in the procedure described for the synthesis of Intermediate 3.6.1. MS (ES, M+H) 232.

Intermediate 3.6.8: (1-(trans-2-methylcyclopropyl)-N-[(1-methyl-1H-pyrazol-3-yl)methyl]methanamine

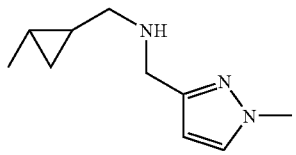

Prepared from intermediate 3.4.1 and 1-methyl-1H-pyrazole-3-carboxylic acid using steps A and B in the procedure described for the synthesis of Intermediate 3.6.1.

Intermediate 3.6.9: 1-(trans-2-methylcyclopropyl)-N-[(1-methyl-1H-imidazol-2-yl)methyl]methanamine

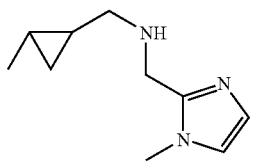

Prepared from intermediate 3.4.1 and 1-methyl-1H-imidazole-2-carboxylic acid using steps A and B in the procedure described for the synthesis of Intermediate 3.6.1.

Intermediate 3.6.10: 1-(trans-2-methylcyclopropyl)-N-[(1-methyl-1H-pyrazol-4-yl)methyl]methanamine

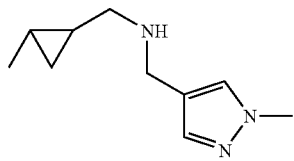

Prepared from intermediate 3.4.1 and 1-methyl-1H-pyrazole-4-carboxylic acid using steps A and B in the procedure described for the synthesis of Intermediate 3.6.1.

Intermediate 3.7.1: ethyl N-[(trans-2-methylcyclopropyl)methyl]glycinate

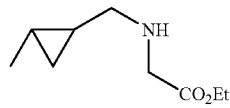

Step A: Reductive Amination.

A DCE solution (50 mL) of Intermediate 3.2.1 as hydrochloride (2.0 g, 9.45 mmol) was cooled to 0° C. and treated with ethyl glyoxylate (1.01 g, 2.2 mL, 9.92 mmol, 50% toluene solution) followed by NaHB(OAc)$_3$ (2.83 g, 13.2 mmol). The solution was warmed to rt and stirred overnight. At this time aqueous bicarbonate was added and the solution stirred for 20 min. The mixture was extracted repeatedly with EtOAc and the combined organic layers washed with brine. Upon drying over Na$_2$SO$_4$, solvent removal and further drying under reduced pressure 2.0 g of ethyl N-benzyl-N-[(trans-2-methylcyclopropyl)methyl]glycinate was obtained as a white semi-solid. LC/MS [M+H]=262.2.

Step B: Hydrogenation.

A 250 mL flask charged with above substrate (2.0 g, 7.6 mmol) in 75 mL of EtOH was purged with N$_2$ for 10 min. To this solution was added 10% Pd(OH)$_2$ (80 mg) followed by HCl (2.0 mL, 7.6 mmol, 4.0 N dioxane solution). The contents were put under a hydrogen atmosphere using a balloon. After stirring overnight the mixture was filtered over Celite. An additional equivalent of HCl was added and the mixture concentrated and dried in vacuo to give 1.6 g of above titled product as hydrochloride salt (off-white solid): $^1$H NMR (CD$_3$OD, 400 MHz) 34.28 (q, J=7.2 Hz, 2H); 3.95 (s, 2H); 2.95 (m, 2H); 1.29 (t, J=7.2 Hz, 3H); 1.07 (d, J=5.6 Hz, 3H); 0.82 (m, 2H); 0.55 (m, 1H); 0.45 (m, 2H); LC/MS [M+H]=176.3.

Intermediate 4.2a.1: 2-chloro-6-[methyl(methylsulfonyl)amino]isonicotinic acid (Scheme 4)

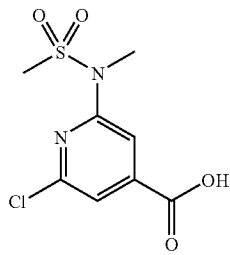 [SMILES: CN(c1cc(C(=O)O)cc(Cl)n1)S(C)(=O)=O]

Prepared from Methyl 2,6-dichloroisonicotinate and methyl(methylsulfonyl)amine as described in the preparation of intermediate 4.2c.1, steps A and B.

Intermediate 4.2b.1: 2-chloro-6-{(2-methoxyethyl)[(trans-2-methylcyclopropyl)methyl]amino}isonicotinic acid (Scheme 4)

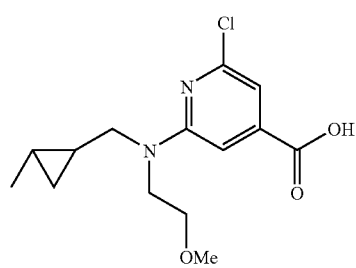 [SMILES: COCCN(CC1CC1C)c1cc(C(=O)O)cc(Cl)n1]

Prepared from 2,6-dichloroisonicotinic acid and intermediate 3.6.1 following a similar procedure as described for the preparation of intermediate 4.2c.1, step C. MS M+1=299.

Intermediate 4.2b.2: 2-chloro-6-{(2-methyl)[(trans-2-methylcyclopropyl)methyl]amino}isonicotinic acid (Scheme 4)

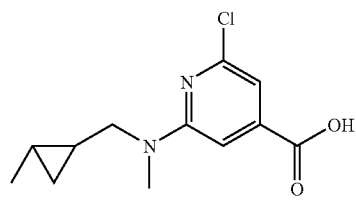 [SMILES: CC1CC1CN(C)c1cc(C(=O)O)cc(Cl)n1]

Prepared from 2,6-dichloroisonicotinic acid and intermediate 3.3.1 following a similar procedure as described for the preparation of intermediate 4.2c.1, step C. MS M+1=255.

Intermediate 4.2c.1: 2-{(2-methoxyethyl)[(trans-2-methylcyclopropyl)methyl]amino}-6-methyl(methylsulfonyl)amino}isonicotic acid (Scheme 4)

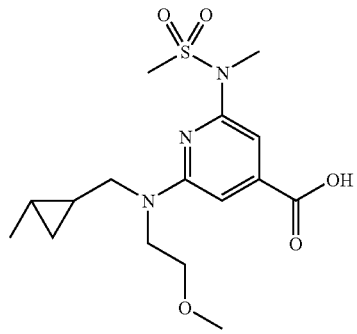 [SMILES: COCCN(CC1CC1C)c1cc(C(=O)O)cc(N(C)S(C)(=O)=O)n1]

Step A: Sulfonamide Incorporation

Methyl 2,6-dichloroisonicotinate (25 g, 121.3 mmol), methyl(methylsulfonyl)amine (3.18 g, 29.12 mmol), potassium phosphate (38.6 g, 182 mmol), Xantphos (4.2 g, 7.28 mmol) and tris(dibenzylideneacetone)dipalladium (2.22 g, 2.43 mmol) were added to a dry, argon flushed flask. Dioxane (1200 mL) was added, the solution degassed with argon and the reaction was heated to 100° C. for 16 hours. The reaction was cooled to rt, filtered through celite and evaporated in vacuo. Flash chromatography (silica, 0-50% 0 to 40% EtOAc in hexane) gave methyl 2-chloro-6-[methyl(methylsulfonyl)amino]isonicotinate as a yellow oil: $^1$H NMR (400 MHz, CDCl$_3$) δ 7.88 (s, 1H), 7.68 (s, 1H), 3.96 (s, 3H), 3.44 (s, 3H), 3.11 (s, 3H).

Step B: Hydrolysis

To a solution of methyl 2-chloro-6-[methyl(methylsulfonyl)amino]isonicotinate (90.2 g, 323.6 mmol) in 1:1 THF:MeOH (1 L) was added a NaOH (388 mL, 388 mmol, 1N). The reaction mixture was stirred at rt for 2 h, acidified to pH 3-4 with 1N HCl, extracted with dichloromethane (×2), dried over sodium sulfate and concentrated in vacuo to provide 2-chloro-6-[methyl(methylsulfonyl)amino]isonicotinic acid (intermediate 4.2c.1) as a white solid. $^1$H NMR (400 MHz, CD$_3$OD) δ 7.88 (s, 1H), 7.63 (s, 1H), 3.39 (s, 3H), 3.13 (s, 3H).

Step C: Amine Incorporation

A suspension of 2-chloro-6-[methyl(methylsulfonyl)amino]isonicotinic acid (20 g, 75.6 mmol), trans (2-methoxyethyl)[(2-methylcyclopropyl)methyl]amine hydrochloride (17.65 g, 98.2 mmol), potassium phosphate (48.12 g, 226.7 mmol) in DMA (300 mL) was degassed with argon for 10 min. Pd(PtBu$_3$)$_2$ (1.93 g, 3.78 mmol) was added and the reaction mixture was degassed with argon for 10 min. The reaction mixture was stirred at 110° C. for 24 hours. The reaction was cooled to rt, filtered through celite, rinsed with EtOAc, diluted with water, the pH was adjusted to 3-4 with 1N HCl, extracted with EtOAc (×3). The organic layer was washed with aq LiCl, dried over sodium sulfate and concentrated in vacuo to give 2-{(2-methoxyethyl)[(trans-2-methylcyclopropyl)methyl]amino}-6-[methyl(methylsulfonyl)amino]isonicotinic acid. $^1$H NMR (400 MHz, CDCl$_3$) δ 7.05 (s, 1H), 7.62 (s, 1H), 3.76 (t, J=6.3 Hz, 2H), 3.60 (t, J=6.3 Hz, 2H), 3.52-3.43 (m, 1H), 3.39 (s, 3H), 3.36 (s, 3H), 3.38-3.30 (m, 1H), 3.18 (s, 3H), 1.23 (d, J=6.1 Hz, 3H), 0.82-0.64 (m, 2H), 0.46-0.39 (m, 1H), 0.32-0.25 (m, 1H).

Intermediate 4.2c.2: 2-{benzyl[(2-methylcyclopropyl)methyl]amino}-6-[methyl(methylsulfonyl)amino]isonicotinic acid (Scheme 4)

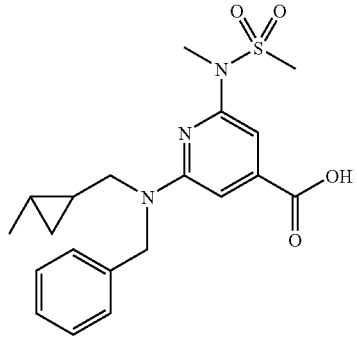 [SMILES: CC1CC1CN(Cc1ccccc1)c1cc(C(=O)O)cc(N(C)S(C)(=O)=O)n1]

Prepared from Methyl 2,6-dichloroisonicotinate, methyl (methylsulfonyl)amine and intermediate 3.2.1 following a similar procedure as described for the preparation of intermediate 4.2c.1. $^1$H NMR (400 MHz, CD$_3$OD) δ 7.88 (s, 1H), 7.63 (s, 1H), 3.39 (s, 3H), 3.13 (s, 3H).

Intermediate 4.2c.3: 2-{methyl[(2-methylcyclopropyl)methyl]amino}-6-[methyl(methylsulfonyl)amino]isonicotinic acid (Scheme 4)

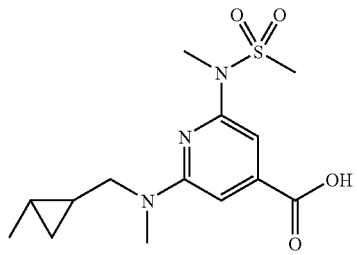 [SMILES: CC1CC1CN(C)c1cc(C(=O)O)cc(N(C)S(C)(=O)=O)n1]

Prepared from Methyl 2,6-dichloroisonicotinate, methyl (methylsulfonyl)amine and intermediate 3.3.1 following a similar procedure as described for the preparation of intermediate 4.2c.1. $^1$H NMR (400 MHz, CD$_3$OD) δ 7.02 (s, 1H), 6.96 (s, 1H), 3.55 (A of ABX, dd, J=14.4, 6.0 Hz, 1H), 3.29 (B of ABX, dd, J=14.4, 7.2 Hz, 1H), 3.35 (s, 3H), 3.15 (s, 3H), 3.12 (s, 3H), 1.03 (d, J=6.0 Hz, 3H), 0.82-0.66 (m, 2H), 0.48-0.41 (m, 1H), 0.28-0.22 (m, 1H).

Intermediate 4.2c.4: 2-{(2,2-difluoroethyl)[(2-trans-methylcycloprogpyl)methyl]amino}-6-[(2-methoxyethyl)(methylsulfonyl)amino]isonicotinic acid (Scheme 4)

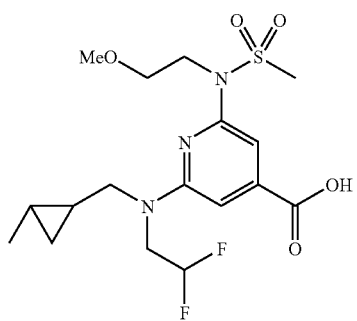 [SMILES: COCCN(c1cc(C(=O)O)cc(N(CC(F)F)CC2CC2C)n1)S(C)(=O)=O]

Prepared from Methyl 2,6-dichloroisonicotinate, 2-methoxyethyl(methylsulfonyl)amine and intermediate 3.6.2 following a similar procedure as described for the preparation of intermediate 4.2c.1. MS M+1=422.

Intermediate 4.2c.5: 2-{(2-methoxyethyl)[(2-trans-methylcyclopropyl)methyl]amino}-6-[(2-methoxyethyl)(methylsulfonyl)amino]isonicotinic acid (Scheme 4)

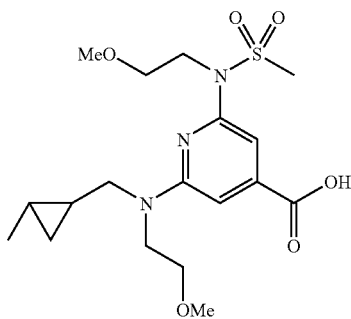 [SMILES: COCCN(CC1CC1C)c1cc(C(=O)O)cc(N(CCOC)S(C)(=O)=O)n1]

Prepared from Methyl 2,6-dichloroisonicotinate, 2-methoxyethyl(methylsulfonyl)amine and intermediate 3.6.1 following a similar procedure as described for the preparation of intermediate 4.2c.1. MS M+1=416.

Intermediate 4.2c.6: 2-{(2-methoxyethyl)[(2-trans-methylcyclopropyl)methyl]amino}-6-[(2-methoxyethyl)(methylsulfonyl)amino]isonicotinic acid (Scheme 4)

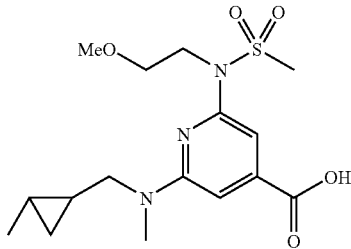 [SMILES: COCCN(c1cc(C(=O)O)cc(N(C)CC2CC2C)n1)S(C)(=O)=O]

Prepared from Methyl 2,6-dichloroisonicotinate, 2-methoxyethyl(methylsulfonyl)amine and intermediate 3.3.1 following a similar procedure as described for the preparation of intermediate 4.2c.1. MS M+1=372.

Intermediate 4.2c.7: 2-(1,1-dioxidoisothiazolidin-2-yl)-6-{(2-methoxyethyl)[(trans-2-methlcyclopropyl)methyl]amino}isonicotinic acid (Scheme 4)

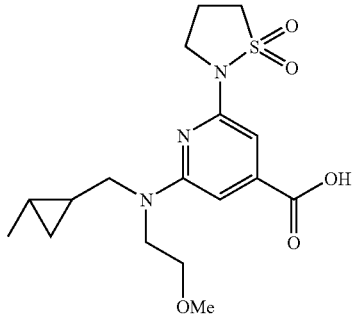 [SMILES: COCCN(CC1CC1C)c1cc(C(=O)O)cc(N2CCCS2(=O)=O)n1]

Prepared from Methyl 2,6-dichloroisonicotinate, isothiazolidine 1,1-dioxide and intermediate 3.6.1 following a similar procedure as described for the preparation of intermediate 4.2c.1. MS M+1=384.

Intermediate 4.2c.8: 2-{benzyl[(trans-2-methylcyclopropyl)methyl]amino}-6-(1,1-dioxidoisothiazolidin-2-yl)isonicotinic acid (Scheme 4)

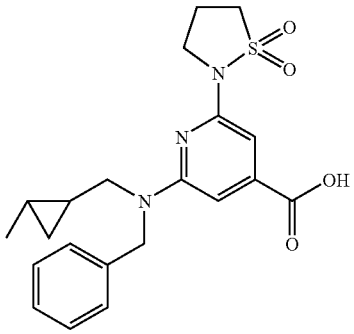 [SMILES: CC1CC1CN(Cc1ccccc1)c1cc(C(=O)O)cc(N2CCCS2(=O)=O)n1]

Prepared from Methyl 2,6-dichloroisonicotinate, isothiazolidine 1,1-dioxide and intermediate 3.2.1 following a similar procedure as described for the preparation of intermediate 4.2c.1. MS M+1=416.

Intermediate 4.2c.9: 2-{(2-{[tert-butyl(dimethyl)silyl]oxy}ethyl)[(trans-2-methylcyclopropyl)methyl]amino}-6-[methyl(methylsulfonyl)amino]isonicotinic acid (Scheme 4)

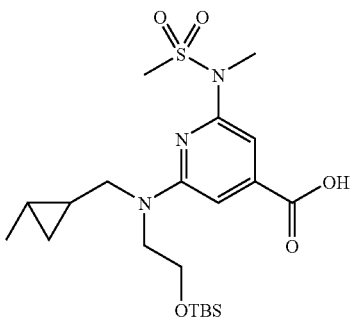 [SMILES: CC1CC1CN(CCO[Si](C)(C)C(C)(C)C)c1cc(C(=O)O)cc(N(C)S(C)(=O)=O)n1]

Prepared from Methyl 2,6-dichloroisonicotinate, methyl(methylsulfonyl)amine and intermediate 3.6.3 following a similar procedure as described for the preparation of intermediate 4.2c.1. MS M+1=472.

Intermediate 4.2c.10: 2-({(1R)-1-[(2S)-2-methylcyclopropyl]ethyl}amino)-6-[methyl(methylsulfonyl)amino]isonicotinic acid (Scheme 4)

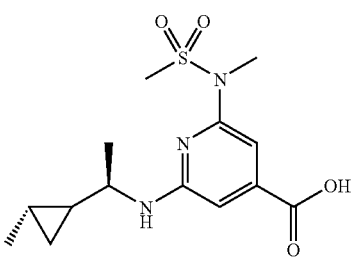 [SMILES: C[C@H]1CC1[C@@H](C)Nc1cc(C(=O)O)cc(N(C)S(C)(=O)=O)n1]

Prepared from Methyl 2,6-dichloroisonicotinate, methyl (methylsulfonyl)amine and intermediate 3.6.5 following a similar procedure as described for the preparation of intermediate 4.2c.1. MS M+1=328.

Intermediate 4.2c.11: 2-{benzyl[(2-methylcyclopropyl)methyl]amino}-6-[methyl(isopropylsulfonyl)amino]isonicotinic acid (Scheme 4)

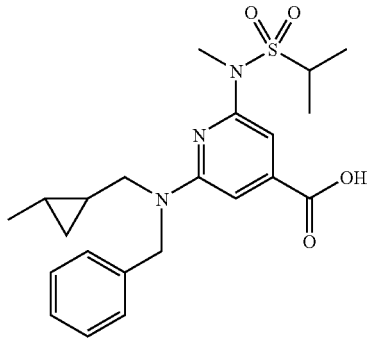 [SMILES: CC1CC1CN(Cc1ccccc1)c1cc(C(=O)O)cc(N(C)S(=O)(=O)C(C)C)n1]

Prepared from Methyl 2,6-dichloroisonicotinate, methyl (isopropylsulfonyl)amine and intermediate 3.2.1 following a similar procedure as described for the preparation of intermediate 4.2c.1. MS M+1=432.

Intermediate 4.2c.12: 2-{benzyl[(2-methylcyclopropyl)methyl]amino}-6-[methyl(ethylsulfonyl)amino]isonicotinic acid (Scheme 4)

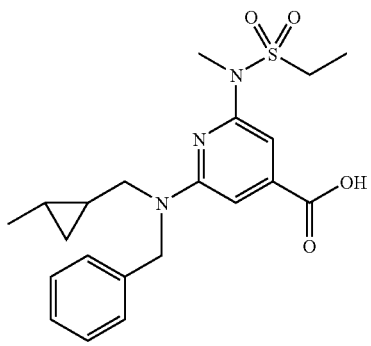 [SMILES: CCS(=O)(=O)N(C)c1cc(C(=O)O)cc(N(Cc2ccccc2)CC2CC2C)n1]

Prepared from Methyl 2,6-dichloroisonicotinate, methyl (ethylsulfonyl)amine and intermediate 3.2.1 following a similar procedure as described for the preparation of intermediate 4.2c.1. MS M+1=418.

Intermediate 4.2c.13: 2-[benzyl(methylsulfonyl)amino]-6-{(2-methoxyethyl)[(trans-2-methylcyclopropyl)methyl]amino}isonicotinic acid (Scheme 4)

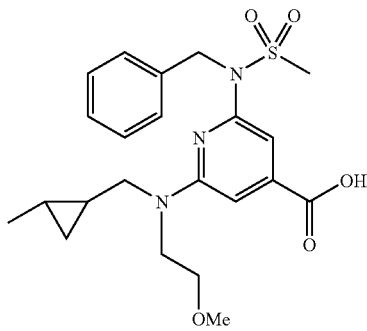 [SMILES: COCCN(CC1CC1C)c1cc(C(=O)O)cc(N(Cc2ccccc2)S(C)(=O)=O)n1]

Prepared from Methyl 2,6-dichloroisonicotinate, benzyl (methylsulfonyl)amine and intermediate 3.6.1 following a similar procedure as described for the preparation of intermediate 4.2c.1. MS M+1=448.

Methyl 2-chloro-6-(methylamino)isonicotinate

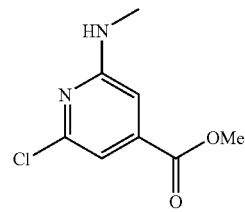

Step A: Methylamine Coupling

To a solution of 2,6-dichloroisonicotinic acid (25 g, 130.2 mmol) in 52 mL water was added 60 mL of 40% methylamine in water. Reaction heated to reflux at 100° C. After 16 h, reaction was cooled to rt. Reaction was acidified with 1N HCl (200 mL) and extracted with EtOAc (300 mL×4). The combined organics were washed with brine (150 mL), dried over $Mg_2SO_4$, filtered, and concentrated in vacuo to give 24.2 g (100%) of 2-chloro-6-(methylamino)isonicotinic acid as a brown solid. LC/MS [M+H]$^+$ 187.0.

Step B: Esterification

To a solution of 2-chloro-6-(methylamino)isonicotinic acid (18.1 g, 97 mmol) in 600 mL MeOH was added thionyl chloride (7.783 mL, 107 mmol) very slowly (emits HCl gas violently). Reaction refluxed to 65° C. for 2 h. After 2 h, reaction was concentrated in vacuo. The residue was dissolved in EtOAc (400 mL) and neutralized with saturated $NaHCO_3$ solution (300 mL). The aqueous solution was extracted with EtOAc (150 mL×3). The combined organics were washed with brine (150 mL), dried over $Mg_2SO_4$, filtered, and concentrated in vacuo. Purification by normal phase chromatography (5% EtOAc/hexanes, then 20% EtOAc/hexanes) yielded 11.3 g (58%) of methyl 2-chloro-6-(methylamino)isonicotinate as a yellow brown solid. $^1$H NMR (CDCl$_3$, 400 mHz) 7.08 (d, J=0.91 Hz, 1H); 6.84 (d, J=0.73 Hz, 1H); 5.09 (s, NH); 3.92 (s, 3H); 2.96 (d, J=5.31 Hz, 3H); LC/MS [M+H]$^+$=201.0.

Intermediate 4.2c.14: 2-{(2-methoxyethyl)[(trans-2-methylcyclopropyl)methyl]amino}-6-[methyl(pyridin-3-ylsulfonyl)amino]isonicotinic acid

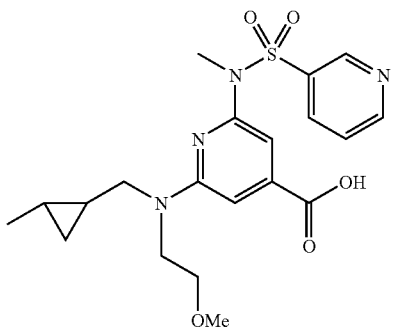 [SMILES: COCCN(CC1CC1C)c1cc(C(=O)O)cc(N(C)S(=O)(=O)c2cccnc2)n1]

Step A: Sulfonylation

To a solution of methyl 2-chloro-6-(methylamino)isonicotinate (2.00 g, 9.97 mmol) in 3:1 CH$_2$Cl$_2$:pyridine (100 mL total) was added 3-pyridine sulfonyl chloride hydrochloride (6.40 g, 29.9 mmol) and dimethylaminopyridine (0.609 g, 4.98 mmol). Reaction heated to reflux at 50° C. After 36 h, reaction cooled to rt. Reaction diluted with CH$_2$Cl$_2$ (200 mL) and washed with 1N HCl (150 mL) solution. The aqueous solution was extracted with CH$_2$Cl$_2$ (100 mL×2). The combined organics were washed with brine (100 mL), dried over Mg$_2$SO$_4$, filtered, and concentrated in vacuo. Purification by normal-phase chromatography (20->40% EtOAc/hexanes) yielded 3.12 g (92%) of methyl 2-chloro-6-[methyl(pyridin-3-ylsulfonyl)amino]isonicotinate as a yellow residue. $^1$H NMR (CDCl$_3$, 400 MHz) 8.95 (d, J=0.64 Hz, 1H); 8.82 (m, 1H); 8.03 (m, 2H); 7.67 (m, 1H); 7.45 (m, 1H); 3.99 (s, 3H); 3.39 (s, 3H); LC/MS [M+H]$^+$=341.9.

Step B: Hydrolysis

To a solution of methyl 2-chloro-6-[methyl(pyridin-3-ylsulfonyl)amino]isonicotinate (3.12 g, 9.13 mmol) in 1:1 MeOH:THF (60 mL total) was added 1N NaOH solution (27 mL, 27.4 mmol). After 1 h, reaction was concentrated in vacuo. Reaction was diluted with EtOAc (100 mL) and acidified with 1N HCl (50 mL) solution. The aqueous solution was extracted with EtOAc (100 mL×3). The combined organics were washed with brine (100 mL), dried over Mg$_2$SO$_4$, filtered, and concentrated in vacuo to give 2.63 g (88%) of 2-chloro-6-[methyl(pyridin-3-ylsulfonyl)amino]isonicotinic acid as a white solid. LC/MS [M+H]$^+$=328.1.

Intermediate 4.2c.15: 2-[[(3,5-dimethylisoxazol-4-yl)sulfonyl](methyl)amino]-6-{(2-methoxyethyl)[(trans-2-methylcyclopropyl)methyl]amino}isonicotinic acid

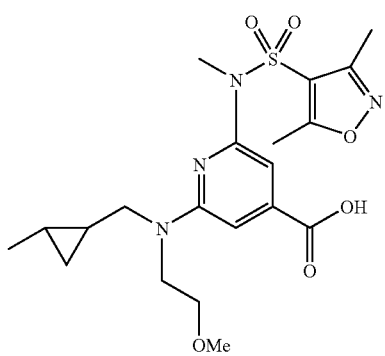 [SMILES: COCCN(CC1CC1C)c1cc(C(=O)O)cc(N(C)S(=O)(=O)c2c(C)noc2C)n1]

Prepared from methyl 2-chloro-6-(methylamino)isonicotinate and 3,5-dimethylisoxazole-4-sulfonyl chloride as described in the preparation of intermediate 4.2c.14. MS M+1=453.

Intermediate 4.2c.16: 2-{(2-methoxyethyl)[(trans-2-methylcyclopropyl)methyl]amino}-6-{methyl[(1-methyl-1H-imidazol-4-yl)sulfonyl]amino} isonicotinic acid

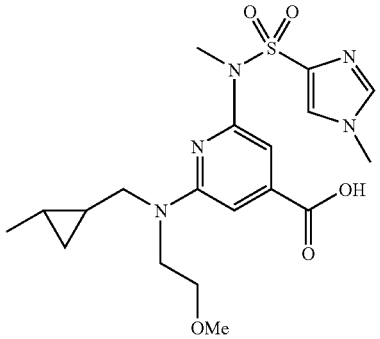 [SMILES: COCCN(CC1CC1C)c1cc(C(=O)O)cc(N(C)S(=O)(=O)c2cn(C)cn2)n1]

Prepared from methyl 2-chloro-6-(methylamino)isonicotinate and 1-methyl-1H-imidazole-4-sulfonyl chloride as described in the preparation of intermediate 4.2c.14. MS M+1=438.

Intermediate 4.2c.17: 2-[({4-(benzyloxy)carbonyl]piperazin-1-yl}sulfonyl)(methyl)amino]-6-{(2-methoxyethyl)[(trans-2-methylcyclopropyl)methyl]amino}isonicotinic acid (Scheme 4)

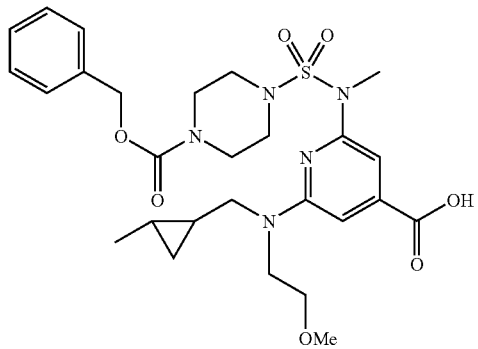 [SMILES: COCCN(CC1CC1C)c1cc(C(=O)O)cc(N(C)S(=O)(=O)N2CCN(C(=O)OCc3ccccc3)CC2)n1]

Prepared from Methyl 2,6-dichloroisonicotinate, benzyl 4-[(methylamino)sulfonyl]piperazine-1-carboxylate and intermediate 3.6.1 following a similar procedure as described for the preparation of intermediate 4.2c.1. MS M+1=576.

Intermediate 4.2c.18: 2-[[(1,2-dimethyl-1H-imidazol-4-yl)sulfonyl](methyl)amino]-6-{(2-methoxyethyl)[(trans-2-methylcyclopropyl)methyl]amino}isonicotinic acid

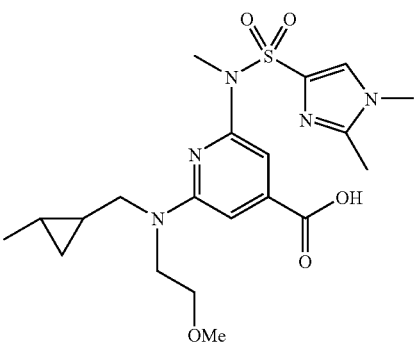

Prepared from methyl 2-chloro-6-(methylamino)isonicotinate and 1,2-dimethyl-1H-imidazole-4-sulfonyl chloride as described in the preparation of intermediate 4.2c.14. MS M+1=576.

Intermediate 4.2c.19: 2-{(2-methoxyethyl)[(trans-2-methylcyclopropyl)methyl]amino}-6-[methyl(morpholin-4-ylsulfonyl)amino]isonicotinic acid (Scheme 4)

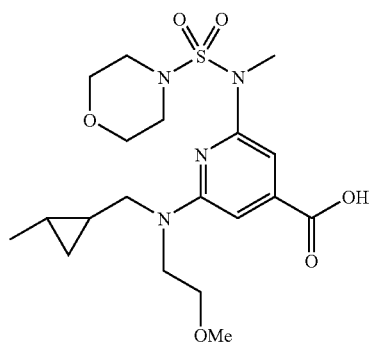 [SMILES: COCCN(CC1CC1C)c1cc(C(=O)O)cc(N(C)S(=O)(=O)N2CCOCC2)n1]

Prepared from Methyl 2,6-dichloroisonicotinate, N-methylmorpholine-4-sulfonamide and intermediate 3.6.1 following a similar procedure as described for the preparation of intermediate 4.2c.1. MS M+1=443.

Intermediate 4.2c.20: 2-{(2-methoxyethyl)[(trans-2-methylcyclopropyl)methyl]amino}-6-(methyl{[(3-methylisoxazol-5-yl)methyl]sulfonyl}amino)isonicotinic acid

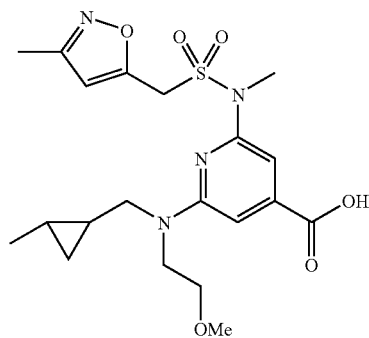 [SMILES: COCCN(CC1CC1C)c1cc(C(=O)O)cc(N(C)S(=O)(=O)Cc2cc(C)no2)n1]

Prepared from Methyl 2,6-dichloroisonicotinate, N-methyl-1-(3-methylisoxazol-5-yl)methanesulfonamide and intermediate 3.6.1 following a similar procedure as described for the preparation of intermediate 4.2c.1. MS M+1=453.

Intermediate 4.2c.21: 2-[[(dimethylamino)sulfonyl](methyl)amino]-6-{(2-methoxyethyl)[(trans-2-methylcyclopropyl)methyl]amino}isonicotinic acid

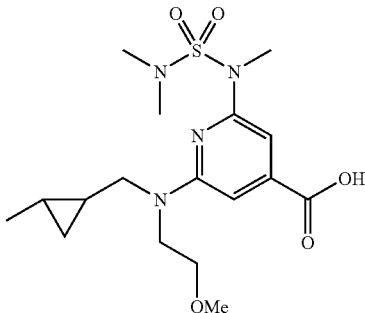 [SMILES: COCCN(CC1CC1C)c1cc(C(=O)O)cc(N(C)S(=O)(=O)N(C)C)n1]

Prepared from Methyl 2,6-dichloroisonicotinate, N,N,N'-trimethylsulfamide and intermediate 3.6.1 following a similar procedure as described for the preparation of intermediate 4.2c.1. MS M+1=401.

Intermediate 4.2c.22: 2-{(2-methoxyethyl)[(2-methylcyclopropyl)methyl]amino}-6-[methyl(pyrrolidin-1-ylsulfonyl)amino]isonicotinic acid

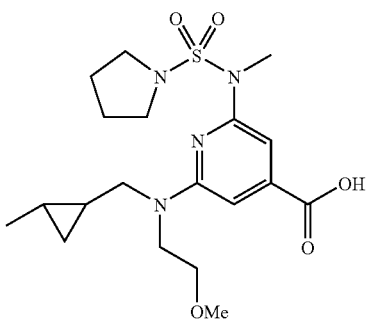 [SMILES: COCCN(CC1CC1C)c1cc(C(=O)O)cc(N(C)S(=O)(=O)N2CCCC2)n1]

Prepared from Methyl 2,6-dichloroisonicotinate, N-methylpyrrolidine-1-sulfonamide and intermediate 3.6.1 following a similar procedure as described for the preparation of intermediate 4.2c.1. MS M+1=427.

Intermediate 4.3c.1: N-(4-(hydrazinocarbonyl)-6-{(2-methoxyethyl)[(trans-2-methylcyclopropyl)methyl]amino}pyridin-2-yl)-N-methylmethanesulfonamide (Scheme 4)

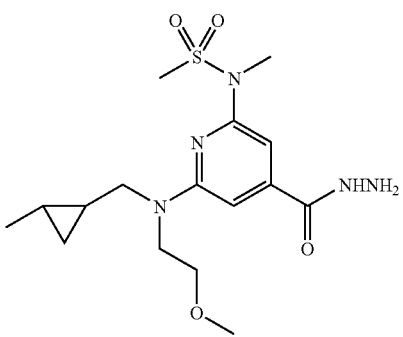 [SMILES: COCCN(CC1CC1C)c1cc(C(=O)NN)cc(N(C)S(C)(=O)=O)n1]

Step A: Coupling

To a solution of 2-{(2-methoxyethyl)[(trans-2-methylcyclopropyl)methyl]amino}-6-[methyl(methylsulfonyl)amino]isonicotinic acid (14.05 g, 37.8 mmol) in DCM (150 mL) was added diisopropylethyl amine (7.91 mL, 45.4 mmol), Boc-hydrazine (6 g, 45.4 mmol), HOAt (1.03 g, 7.6 mmol) and EDC (8.7 g, 45.4 mmol), and the reaction mixture was stirred at rt for 16 h. The reaction mixture was diluted with EtOAc, washed with 10% $KHSO_4$, aq $NaHCO_3$ and brine, dried over sodium sulfate, concentrated in vacuo, and purified by flash chromatography (silica, 30% to 70% EtOAc in hexane) to give tert-butyl 2-{2-{(2-methoxyethyl)[(trans-2-methylcyclopropyl)methyl]amino}-6-[methyl(methylsulfonyl)amino]isonicotinoyl}hydrazinecarboxylate. MS M+1=486.

Step B: Boc Removal

HCl(g) was bubbled through a solution of tert-butyl 2-{2-{(2-methoxyethyl)[(trans-2-methylcyclopropyl)methyl]amino}-6-[methyl(methylsulfonyl)amino]isonicotinoyl}hydrazinecarboxylate (13.6 g, 28 mmol) in DCM (50 mL) cooled to 0° C. After reaction completion by LC, the reaction mixture was concentrated in vacuo to give N-(4-(hydrazinocarbonyl)-6-{(2-methoxyethyl)[(trans-2-methylcyclopropyl)methyl]amino}pyridin-2-yl)-N-methyl-methanesulfonamide as the hydrochloride. $^1$H NMR (400 MHz, $CD_3OD$) δ 6.89 (s, 1H), 6.88 (s, 1H), 3.79 (t, J=6.1 Hz, 2H), 3.62 (t, J=6.3 Hz, 2H), 3.52-3.48 (m, 1H), 3.42-3.35 (m, 1H), 3.33 (s, 3H), 3.31 (s, 3H), 3.16 (s, 3H), 1.04 (d, J=5.9 Hz, 3H), 0.85-0.70 (m, 2H), 0.51-0.42 (m, 1H), 0.31-0.23 (m, 1H).

Note that every acid intermediate of type 4.2c can be converted to the corresponding acyl hydrazide of type 4.3c.

Intermediate 5.2c.1: N-(4-[5-(1R-amino-1-methyl-2-phenylethyl)-1,3,4-oxadiazol-2-yl]-6-{(2-methoxyethyl)[trans-2-methylcyclopropyl)methyl]amino}pyridin-2-yl)-N-methylmethanesulfonamide (Scheme 5)

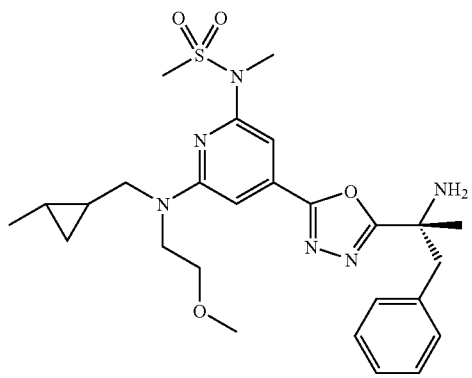 [SMILES: COCCN(CC1CC1C)c1cc(-c2nnc([C@](C)(N)Cc3ccccc3)o2)cc(N(C)S(C)(=O)=O)n1]

Step A: Coupling

To a solution of N-(4-(hydrazinocarbonyl)-6-{(2-methoxyethyl)[(trans-2-methylcyclopropyl)methyl]amino}pyridin-2-yl)-N-methylmethanesulfonamide hydrochloride (intermediate 4.3c.1, 11.81 g, 28 mmol) in DMF (100 mL) was added diisopropylethyl amine (9.75 mL, 56 mmol), Boc-D-alphamethyl-phenyl alanine (8.6 g, 30.8 mmol), HOAt (1.9 g, 14 mmol) and EDC (8.05 g, 42 mmol), and the reaction mixture was stirred at RT for 16 h. The reaction mixture was diluted with EtOAc, washed with 10% $KHSO_4$, aq $NaHCO_3$ and aq LiCl (×3), dried over sodium sulfate, concentrated in vacuo, and purified by flash chromatography (silica, 30% to 70% EtOAc in hexane) to give tert-butyl [(1R)-1-benzyl-2-oxo-(2-{2-{(2-methoxyethyl)[(2-methylcyclopropyl)methyl]amino}-6-[methyl(methylsulfonyl)amino]isonicotinoyl}hydrazino)-1-methylethyl]carbamate. MS M+1=647.

Step B: Cyclodehydration

To a solution of tert-butyl [(1R)-1-benzyl-2-oxo-(2-{2-{(2-methoxyethyl)[(2-methylcyclopropyl)methyl]amino}-6-[methyl(methylsulfonyl)amino]isonicotinoyl}hydrazino)-1-methylethyl]carbamate (16.2 g, 25 mmol), triphenylphosphine (7.88 g, 30.1 mmol) and imidazole (2.05 g, 30.1 mmol) in DCM (150 mL) cooled to 0° C. was added carbon tetrabromide (9.97 g, 30.1 mmol) and the reaction mixture was stirred at RT for 16 h. The reaction mixture was concentrated in vacuo, and purified by flash chromatography (silica, 20% to 50% EtOAc in hexane) to give tert-butyl [(1R)-1-(5-{2-{(2-methoxyethyl)[(trans-2-methylcyclopropyl)methyl]amino}-6-[methyl(methylsulfonyl)amino]pyridin-4-yl}-1,3,4-oxadiazol-2-yl)-1-methyl-2-phenylethyl]carbamate. MS M+1=629.

Step C: Boc Removal

To a solution of tert-butyl [(1R)-1-(5-{2-{(2-methoxyethyl)[(trans-2-methylcyclopropyl)methyl]amino}-6-[methyl(methylsulfonyl)amino]pyridin-4-yl}-1,3,4-oxadiazol-2-yl)-1-methyl-2-phenylethyl]carbamate (14.65 g, 23.3 mmol) in DCM (95 mL) cooled to 0° C. was added TFA (35 mL) and the reaction mixture was stirred at rt for 3 h, concentrated in vacuo, and concentrated again from MeOH and then DCM a few times, to give N-(4-[5-(1R-amino-1-methyl-2-phenylethyl)-1,3,4-oxadiazol-2-yl]-6-{(2-methoxyethyl)[(trans-2-methylcyclopropyl)methyl]amino}pyridin-2-yl)-N-methylmethanesulfonamide as a TFA salt. MS M+1=529. $^1$H NMR (400 MHz, $CDCl_3$) δ 7.32-7.26 (m, 3H), 7.21 (s, 1H), 7.09 (s, 1H), 7.08-7.02 (m, 2H), 3.82 (t, J=5.5 Hz, 2H), 3.75 (t, J=5.5 Hz, 2H), 3.54-3.41 (m, 2H), 3.45 (s, 3H), 3.42 (s, 3H), 3.42-3.36 (m, 2H), 3.16 (s, 3H), 1.96 (s, 3H), 1.05 (d, J=5.8 Hz, 3H), 0.79-0.70 (m, 2H), 0.50-0.44 (m, 1H), 0.42-0.35 (m, 1H).

Intermediate 5.2c.2: N-(4-{5-[(1R)-1-amino-2-(4-fluorophenyl)-1-methylethyl]-1,3,4-oxadiazol-2-yl}-6-{(2-methoxyethyl)[(trans-2-methylcyclopropyl)methyl]amino}pyridin-2-yl)-N-methylmethanesulfonamide (Scheme 5)

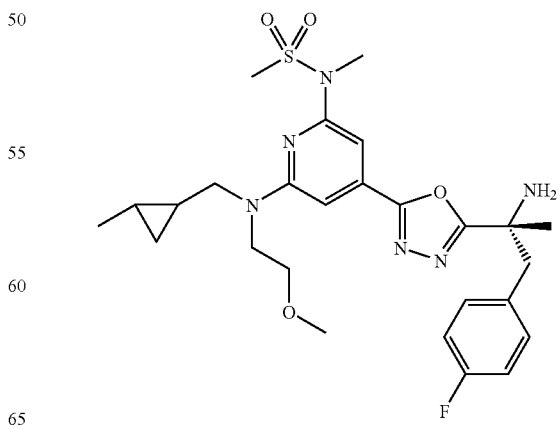

Step A: Coupling

To a solution of N-(4-(hydrazinocarbonyl)-6-{(2-methoxyethyl)[(trans-2-methylcyclopropyl)methyl]amino}pyridin-2-yl)-N-methylmethanesulfonamide hydrochloride (intermediate 4.3c.1, 10.16 g, 24.1 mmol) in DMF (240 mL) was added diisopropylethyl amine (8.39 mL, 48.2 mmol), Boc-D-alphamethyl-4-fluorophenyl alanine (7.88 g, 26.5 mmol), HOAt (1.64 g, 12.0 mmol) and EDC (6.92 g, 36.1 mmol), and the reaction mixture was stirred at rt for 16 h. The reaction mixture was diluted with EtOAc, washed with 10% $KHSO_4$, aq $NaHCO_3$ and aq LiCl (×3), dried over sodium sulfate, an concentrated in vacuo to give tert-butyl [(1R)-1-(4-fluorophenylmethyl)-2-oxo-(2-{2-{(2-methoxyethyl)[(2-methylcyclopropyl)methyl]amino}-6-[methyl(methylsulfonyl)amino]isonicotinoyl}hydrazino)-1-methylethyl]carbamate. MS M+1=665.

Step B: Cyclodehydration

To a solution of tert-butyl [(1R)-1-(4-fluorophenylmethyl)-2-oxo-(2-{2-{(2-methoxyethyl)[(2-methylcyclopropyl)methyl]amino}-6-[methyl(methylsulfonyl)amino]isonicotinoyl}hydrazino)-1-methylethyl]carbamate (16.64 g, 25.0 mmol), triphenylphosphine (7.89 g, 30.1 mmol) and imidazole (2.05 g, 30.1 mmol) in DCM (150 mL) cooled to 0° C. was added carbon tetrabromide (9.98 g, 30.1 mmol) and the reaction mixture was stirred at rt for 16 h. The reaction mixture was filtered, concentrated in vacuo, and purified by flash chromatography (silica, 20% to 50% EtOAc in hexane) to give tert-butyl [(1R)-2-(4-fluorophenyl)-1-(5-{2-{(2-methoxyethyl)[(trans-2-methylcyclopropyl)methyl]amino}-6-[methyl(methylsulfonyl)amino]pyridin-4-yl]-1,3,4-oxadiazol-2-yl)-1-methyl-2-phenylethyl]carbamate. MS M+1=647.

Step C: Boc Removal

To a solution of tert-butyl [(1R)-2-(4-fluorophenyl)-1-(5-{2-{(2-methoxyethyl)[(trans-2-methylcyclopropyl)methyl]amino}-6-[methyl(methylsulfonyl)amino]pyridin-4-yl}-1,3,4-oxadiazol-2-yl)-1-methyl-2-phenylethyl]carbamate (11.58 g, 17.9 mmol) in DCM (75 mL) cooled to 0° C. was added TFA (25 mL) and the reaction mixture was stirred at rt for 16 h, concentrated in vacuo, and reconcentrated several times from DCM, to give N-(4-{5-[(1R)-1-amino-2-(4-fluorophenyl)-1-methylethyl]-1,3,4-oxadiazol-2-yl}-6-{(2-methoxyethyl)[(trans-2-methylcyclopropyl)methyl]amino}pyridin-2-yl)-N-methylmethanesulfonamide as a TFA salt. MS M+1=547. $^1$H NMR (400 MHz, $CD_3OD$) δ 7.10 (m, 5H), 7.01 (s, 1H), 3.82 (t, J=5.86 Hz, 2H), 3.64 (t, J=5.86, 2H), 3.50 (AB overlapping m, 4H), 3.39 (s, 3H), 3.35 (s, 3H), 3.18 (s, 3H), 1.88 (s, 3H), 1.05 (d, J=5.86, 3H), 0.78 (m, 2H), 0.49 (m, 1H), 0.30 (m, 1H).

Additional intermediates wherein X is an oxadiazole were prepared as described in Table 1.

TABLE I

Oxadiazole Intermediates

| Int # | intermediates | Mode of prep | Structure | ES M + 1 |
|---|---|---|---|---|
| 5.1a.1 | 4.2a.1, Boc-D-alpha-methyl-phenylalanine | Coupling, cyclodehydration, See 4.3c.1 and 5.2c.1 (no Boc removal) | 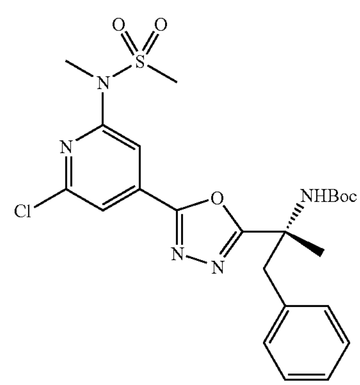 [SMILES: CN(c1cc(-c2nnc([C@@](C)(Cc3ccccc3)NC(=O)OC(C)(C)C)o2)cc(Cl)n1)S(C)(=O)=O] | 522 |
| 5.1b.1 | 4.2b.1, Boc-D-alpha-methyl-phenylalanine | Coupling, cyclodehydration, See 4.3c.1 and 5.2c.1 (no Boc removal) | 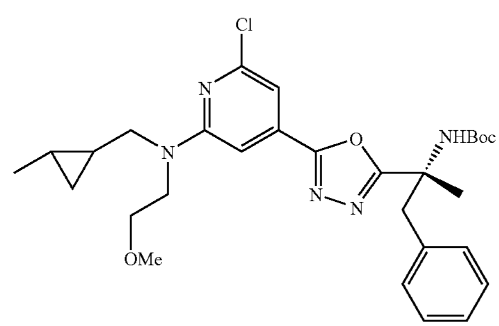 [SMILES: COCCN(CC1CC1C)c1cc(-c2nnc([C@@](C)(Cc3ccccc3)NC(=O)OC(C)(C)C)o2)cc(Cl)n1] | 557 |

TABLE I-continued

Oxadiazole Intermediates

| Int # | intermediates | Mode of prep | Structure | ES M + 1 |
|---|---|---|---|---|
| 5.1b.2 | 4.2b.2, Boc-D-alpha-methyl-phenylalanine | Coupling, cyclodehydration, See 4.3c.1 and 5.2c.1 (no Boc removal) | 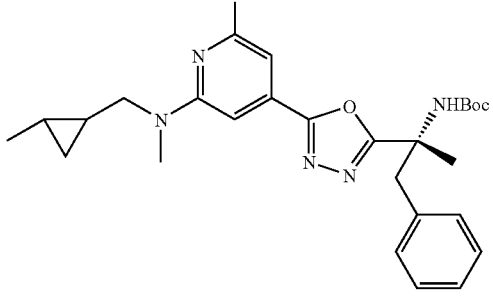 | 512 |
| 5.1c.1 | 5.1a.1 and 3.7.1 | Pd coupling as in 4.2c.1 stepC | 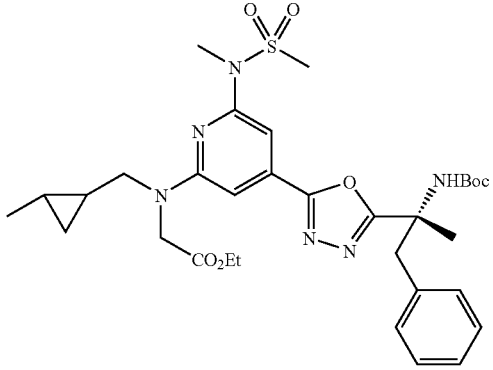 [SMILES: CCOC(=O)CN(CC1CC1C)c1cc(-c2nnc([C@@](C)(Cc3ccccc3)NC(=O)OC(C)(C)C)o2)cc(N(C)S(C)(=O)=O)n1] | 657 |
| 5.1c.2 | 4.2c.13, Boc-D-alpha-methyl-phenylalanine | Coupling, cyclodehydration, See 4.3c.1 and 5.2c.1 (no Boc removal), N-debenzylation | 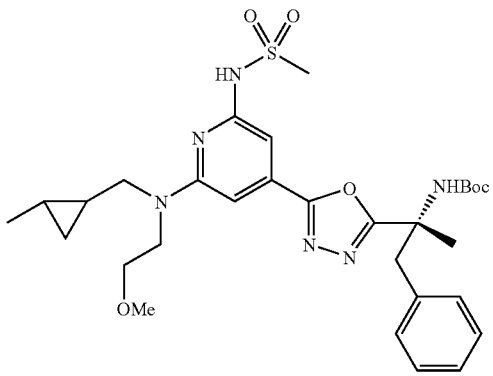 [SMILES: COCCN(CC1CC1C)c1cc(-c2nnc([C@@](C)(Cc3ccccc3)NC(=O)OC(C)(C)C)o2)cc(NS(C)(=O)=O)n1] | 615 |
| 5.2c.3 | 4.2c.2, Boc-D-alpha-methyl-phenylalanine | Coupling, cyclodehydration, Bn hydrogenation, Boc removal, See 5.2c.1 | 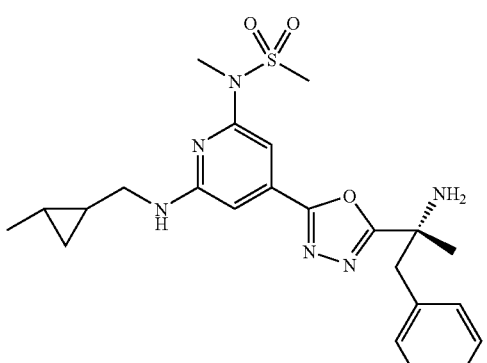 | 471 |

TABLE I-continued

Oxadiazole Intermediates

| Int # | intermediates | Mode of prep | Structure | ES M + 1 |
|---|---|---|---|---|
| 5.2c.4 | 4.2c.2, Boc-D-alpha-methyl-4-fluoro-phenylalanine | Coupling, cyclodehydration, Bn hydrogenation, Boc removal, See 4.3c.1 and 5.2c.1 | 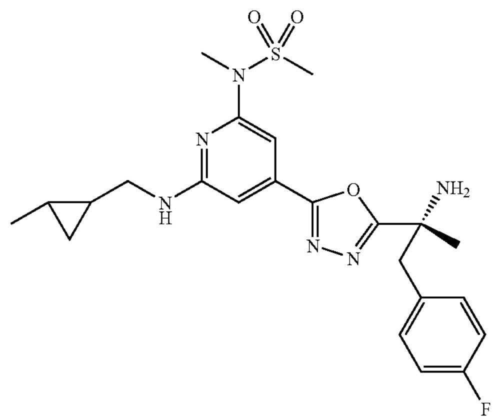 [SMILES: CC1CC1CNc1cc(-c2nnc([C@](C)(N)Cc3ccc(F)cc3)o2)cc(N(C)S(C)(=O)=O)n1] | 489 |
| 5.2c.5 | 4.2c.3, Boc-D-alpha-methyl-phenylalanine | Coupling, cyclodehydration, Boc removal, See See 4.3c.1 and 5.2c.1 | 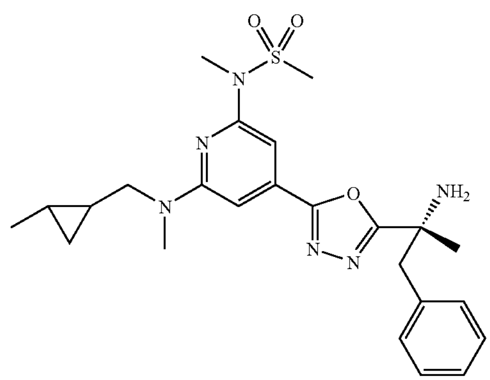 [SMILES: CC1CC1CN(C)c1cc(-c2nnc([C@](C)(N)Cc3ccccc3)o2)cc(N(C)S(C)(=O)=O)n1] | 485 |
| 5.2c.6 | 4.2c.3, Boc-D-alpha-methyl-4-fluoro-phenylalanine | Coupling, cyclodehydration, Boc removal, See See 4.3c.1 and 5.2c.1 | 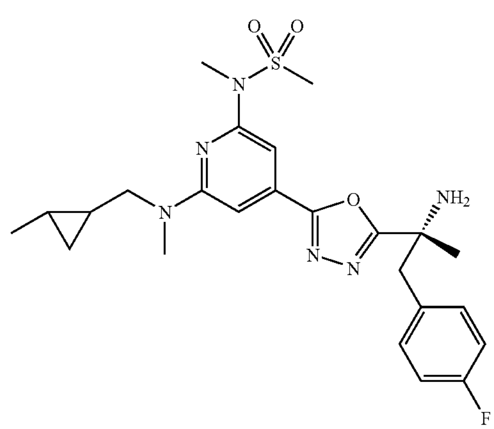 [SMILES: CC1CC1CN(C)c1cc(-c2nnc([C@](C)(N)Cc3ccc(F)cc3)o2)cc(N(C)S(C)(=O)=O)n1] | 503 |

TABLE I-continued

Oxadiazole Intermediates

| Int # | intermediates | Mode of prep | Structure | ES M + 1 |
|---|---|---|---|---|
| 5.2c.7 | 4.2c.4, Boc-D-alpha-methyl-phenylalanine | Coupling, cyclodehydration, Boc removal, See See 4.3c.1 and 5.2c.1 | 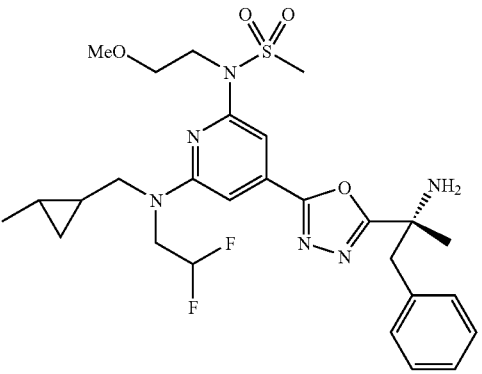 [SMILES: COCCN(c1cc(-c2nnc([C@](C)(N)Cc3ccccc3)o2)cc(N(CC(F)F)CC2CC2C)n1)S(C)(=O)=O] | 579 |
| 5.2c.8 | 4.2c.5, Boc-D-alpha-methyl-phenylalanine | Coupling, cyclodehydration, Boc removal, See See 4.3c.1 and 5.2c.1 | 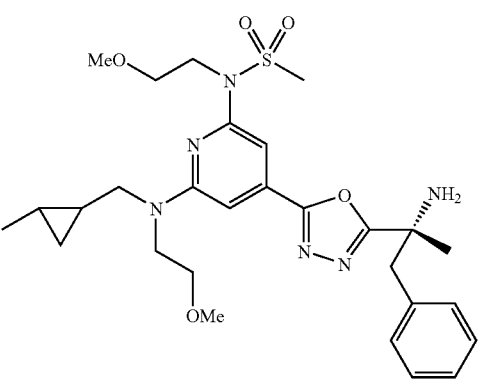 [SMILES: COCCN(CC1CC1C)c1cc(-c2nnc([C@](C)(N)Cc3ccccc3)o2)cc(N(CCOC)S(C)(=O)=O)n1] | 573 |
| 5.2c.9 | 4.2c.6, Boc-D-alpha-methyl-phenylalanine | Coupling, cyclodehydration, Boc removal, See See 4.3c.1 and 5.2c.1 | 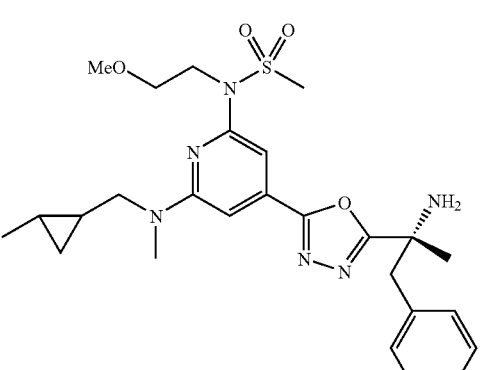 | 519 |
| 5.2c.10 | 4.2c.7, Boc-D-alpha-methyl-phenylalanine | Coupling, cyclodehydration, Boc removal, See See 4.3c.1 and 5.2c.1 | 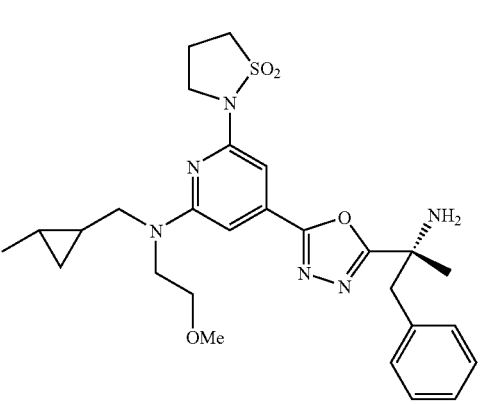 [SMILES: COCCN(CC1CC1C)c1cc(-c2nnc([C@](C)(N)Cc3ccccc3)o2)cc(N2CCCS2(=O)=O)n1] | 541 |

TABLE I-continued

Oxadiazole Intermediates

| Int # | intermediates | Mode of prep | Structure | ES M + 1 |
|---|---|---|---|---|
| 5.2c.11 | 4.2c.8, Boc-D-alpha-methyl-phenylalanine | Coupling, cyclodehydration, Bn hydrogenation, Boc removal, See 4.3c.1 and 5.2c.1 | 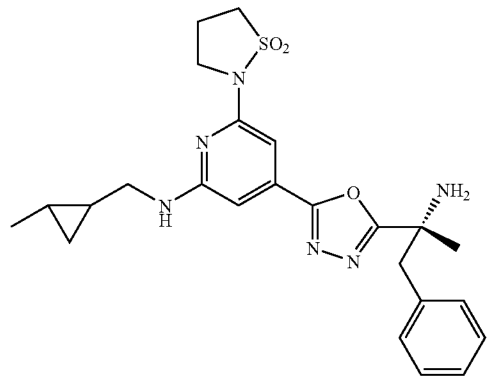 [SMILES: CC1CC1CNc1cc(-c2nnc([C@](C)(N)Cc3ccccc3)o2)cc(N2CCCS2(=O)=O)n1] | 483 |
| 5.2c.12 | 4.2c.9, Boc-D-alpha-methyl-phenylalanine | Coupling, cyclodehydration, TBAF desylation, Boc removal, See 4.3c.1 and 5.2c.1 | 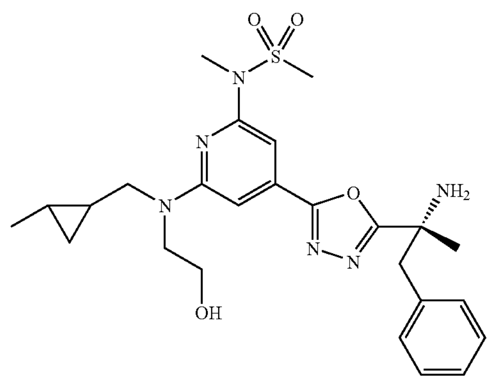 [SMILES: CC1CC1CN(CCO)c1cc(-c2nnc([C@](C)(N)Cc3ccccc3)o2)cc(N(C)S(C)(=O)=O)n1] | 515 |
| 5.2c.13 | 4.2c.10, Boc-D-alpha-methyl-phenylalanine | Coupling, cyclodehydration, Boc removal, See 4.3c.1 and 5.2c.1 | 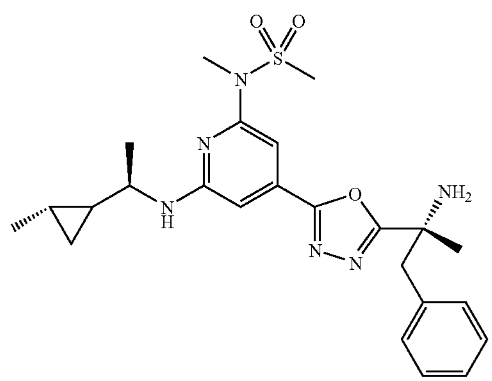 [SMILES: C[C@H]1CC1[C@@H](C)Nc1cc(-c2nnc([C@](C)(N)Cc3ccccc3)o2)cc(N(C)S(C)(=O)=O)n1] | 485 |
| 5.2c.14 | 4.2c.11, Boc-D-alpha-methyl-phenylalanine | Coupling, cyclodehydration, Bn hydrogenation, Boc removal, See 4.3c.1 and 5.2c.1 | 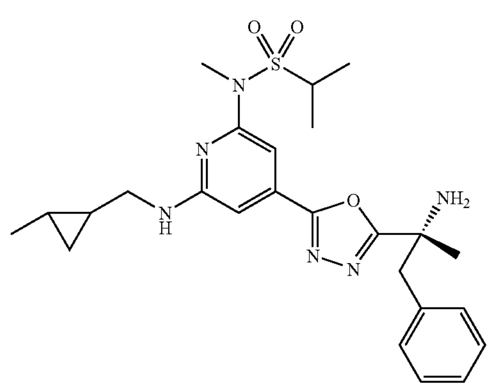 [SMILES: CC1CC1CNc1cc(-c2nnc([C@](C)(N)Cc3ccccc3)o2)cc(N(C)S(=O)(=O)C(C)C)n1] | 499 |

TABLE I-continued

Oxadiazole Intermediates

| Int # | intermediates | Mode of prep | Structure | ES M + 1 |
|---|---|---|---|---|
| 5.2c.15 | 4.2c.12, Boc-D-alpha-methyl-phenylalanine | Coupling, cyclodehydration, Bn hydrogenation, Boc removal, See 4.3c.1 and 5.2c.1 | 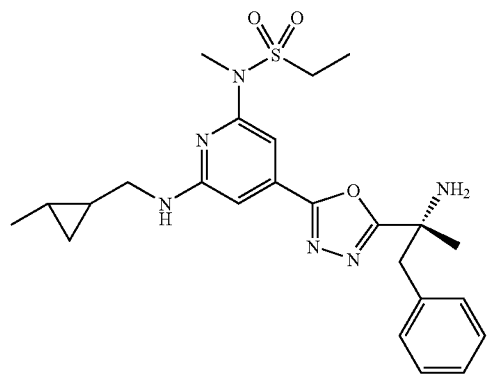 [SMILES: CCS(=O)(=O)N(C)c1cc(-c2nnc([C@](C)(N)Cc3ccccc3)o2)cc(NCC2CC2C)n1] | 485 |
| 5.2c.16 | 5.1b.2 | Methanesulfonamide/Pd coupling as in 4.2c.1 stepA, Boc removal | 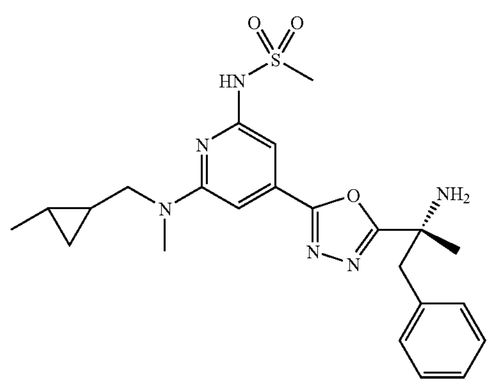 [SMILES: CC1CC1CN(C)c1cc(-c2nnc([C@](C)(N)Cc3ccccc3)o2)cc(NS(C)(=O)=O)n1] | 471 |
| 5.2c.17 | 5.1a.1 and 3.6.6 | Pd coupling as in 4.2c.1 stepC, Boc removal | 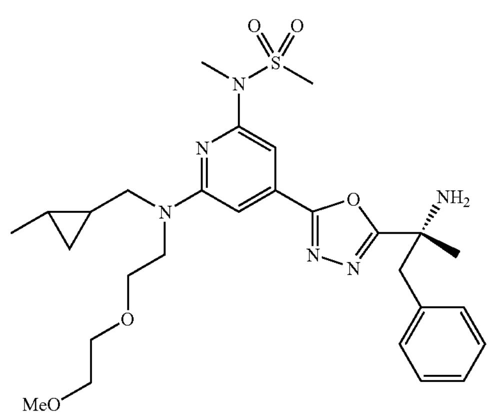 [SMILES: COCCOCCN(CC1CC1C)c1cc(-c2nnc([C@](C)(N)Cc3ccccc3)o2)cc(N(C)S(C)(=O)=O)n1] | 572 |

TABLE I-continued
Oxadiazole Intermediates
| Int # | intermediates | Mode of prep | Structure | ES M + 1 |
|---|---|---|---|---|
| 5.2c.18 | 5.1a.1 and 3.6.7 | Pd coupling as in 4.2c.1 stepC, Boc removal | 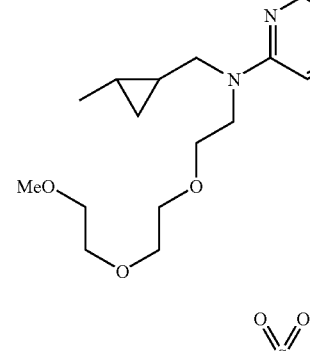 | 616 |
| 5.2c.19 | 5.1a.1 and 3.6.8 | Pd coupling as in 4.2c.1 stepC, Boc removal | 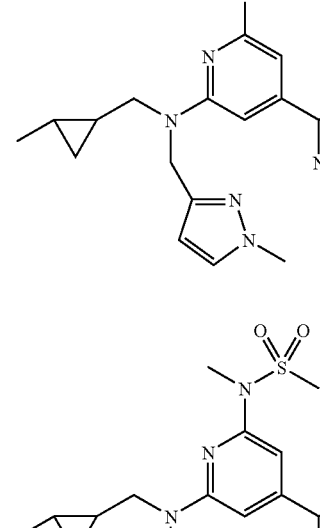 | 564 |
| 5.2c.20 | 5.1a.1 and 3.6.9 | Pd coupling as in 4.2c.1 stepC, Boc removal | 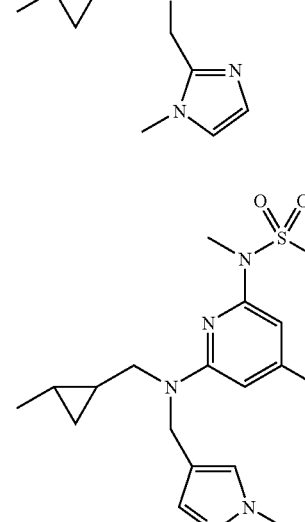 | 564 |
| 5.2c.21 | 5.1a.1 and 3.6.10 | Pd coupling as in 4.2c.1 stepC, Boc removal | 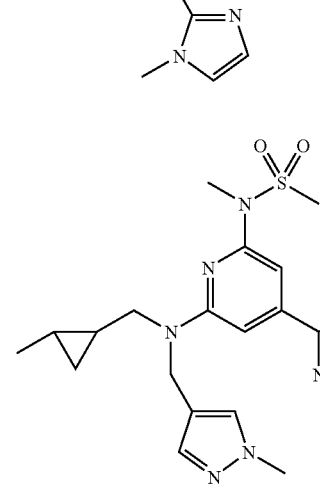 | 564 |

TABLE I-continued

Oxadiazole Intermediates

| Int # | intermediates | Mode of prep | Structure | ES M + 1 |
|---|---|---|---|---|
| 5.2c.22 | 5.1c.1 | Boc removal | 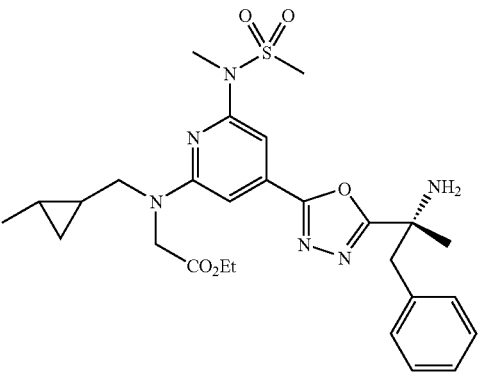 [SMILES: CCOC(=O)CN(CC1CC1C)c1cc(-c2nnc([C@](C)(N)Cc3ccccc3)o2)cc(N(C)S(C)(=O)=O)n1] | 557 |
| 5.2c.23 | 4.2c.14, Boc-D-alpha-methyl-phenylalanine | Coupling, cyclodehydration, Boc removal, See 4.3c.1 and 5.2c.1 | 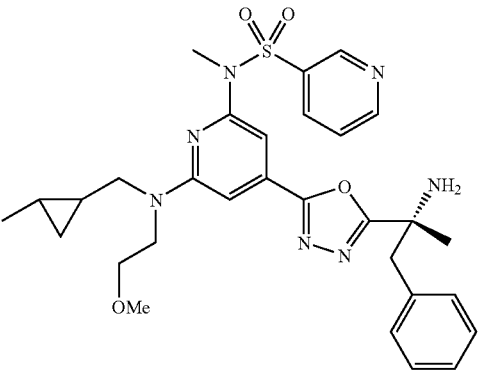 [SMILES: COCCN(CC1CC1C)c1cc(-c2nnc([C@](C)(N)Cc3ccccc3)o2)cc(N(C)S(=O)(=O)c2cccnc2)n1] | 591 |
| 5.2c.24 | 4.2c.15, Boc-D-alpha-methyl-phenylalanine | Coupling, cyclodehydration, Boc removal, See 4.3c.1 and 5.2c.1 | 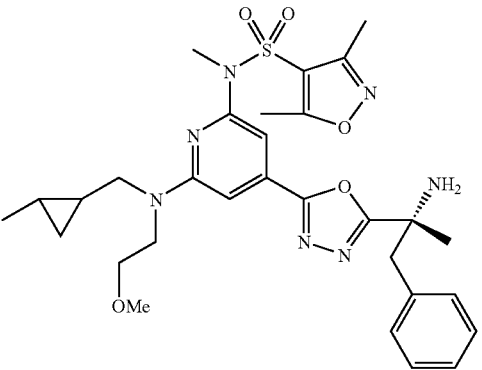 [SMILES: COCCN(CC1CC1C)c1cc(-c2nnc([C@](C)(N)Cc3ccccc3)o2)cc(N(C)S(=O)(=O)c2c(C)noc2C)n1] | 609 |
| 5.2c.25 | 4.2c.16, Boc-D-alpha-methyl-phenylalanine | Coupling, cyclodehydration, Boc removal, See 4.3c.1 and 5.2c.1 | 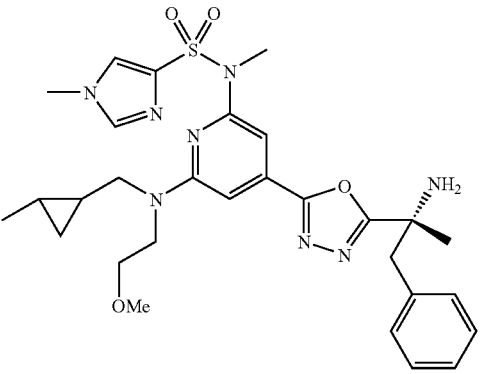 [SMILES: COCCN(CC1CC1C)c1cc(-c2nnc([C@](C)(N)Cc3ccccc3)o2)cc(N(C)S(=O)(=O)c2cn(C)cn2)n1] | 594 |

TABLE I-continued

Oxadiazole Intermediates

| Int # | intermediates | Mode of prep | Structure | ES M + 1 |
|---|---|---|---|---|
| 5.2c.26 | 4.2c.17, Boc-D-alpha-methyl-phenylalanine | Coupling, cyclodehydration, Cbz removal, Boc removal, See 4.3c.1 and 5.2c.1 | 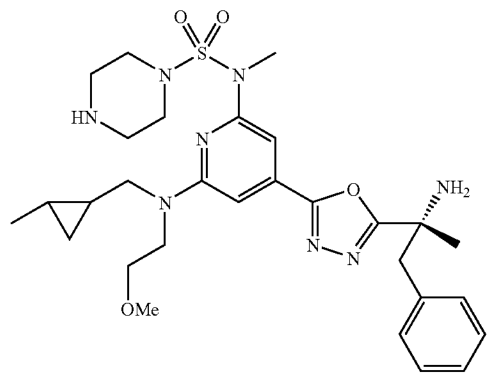 [SMILES: COCCN(CC1CC1C)c1cc(-c2nnc([C@](C)(N)Cc3ccccc3)o2)cc(N(C)S(=O)(=O)N2CCNCC2)n1] | 598 |
| 5.2c.27 | 4.2c.17, Boc-D-alpha-methyl-phenylalanine | Coupling, cyclodehydration, Cbz removal, MeI alkylation, Boc removal, See 4.3c.1 and 5.2c.1 | 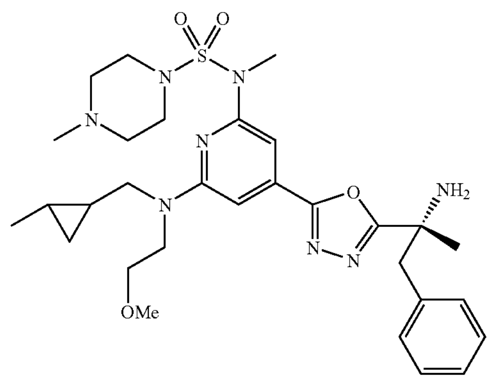 [SMILES: COCCN(CC1CC1C)c1cc(-c2nnc([C@](C)(N)Cc3ccccc3)o2)cc(N(C)S(=O)(=O)N2CCN(C)CC2)n1] | 612 |
| 5.2c.28 | 4.2c.17, Boc-D-alpha-methyl-phenylalanine | Coupling, cyclodehydration, Cbz removal, acetylation, Boc removal, See 4.3c.1 and 5.2c.1 | 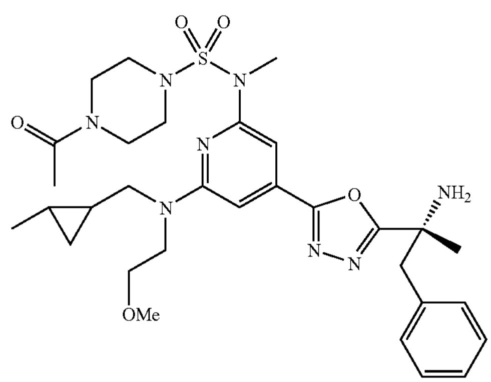 [SMILES: COCCN(CC1CC1C)c1cc(-c2nnc([C@](C)(N)Cc3ccccc3)o2)cc(N(C)S(=O)(=O)N2CCN(C(C)=O)CC2)n1] | 640 |
| 5.2c.29 | 4.2c.18, Boc-D-alpha-methyl-phenylalanine | Coupling, cyclodehydration, Boc removal, See 4.3c.1 and 5.2c.1 | 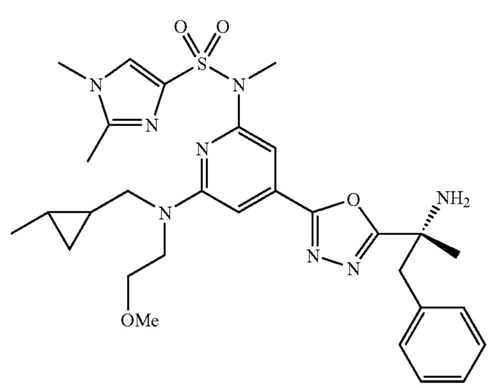 [SMILES: COCCN(CC1CC1C)c1cc(-c2nnc([C@](C)(N)Cc3ccccc3)o2)cc(N(C)S(=O)(=O)c2cn(C)c(C)n2)n1] | 608 |

TABLE I-continued

Oxadiazole Intermediates

| Int # | intermediates | Mode of prep | Structure | ES M + 1 |
|---|---|---|---|---|
| 5.2c.30 | 4.2c.19, Boc-D-alpha-methyl-phenylalanine | Coupling, cyclodehydration, Boc removal, See 4.3c.1 and 5.2c.1 | 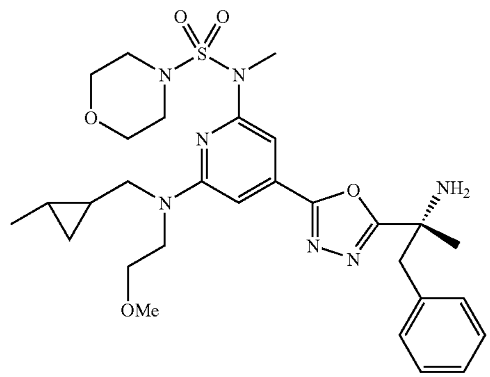 [SMILES: COCCN(CC1CC1C)c1cc(-c2nnc([C@](C)(N)Cc3ccccc3)o2)cc(N(C)S(=O)(=O)N2CCOCC2)n1] | 599 |
| 5.2c.31 | 4.2c.20, Boc-D-alpha-methyl-phenylalanine | Coupling, cyclodehydration, Boc removal, See 4.3c.1 and 5.2c.1 | 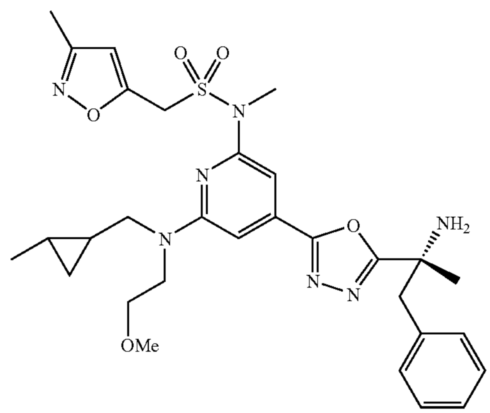 [SMILES: COCCN(CC1CC1C)c1cc(-c2nnc([C@](C)(N)Cc3ccccc3)o2)cc(N(C)S(=O)(=O)Cc2cc(C)no2)n1] | 609 |
| 5.2c.32 | 4.2c.21, Boc-D-alpha-methyl-phenylalanine | Coupling, cyclodehydration, Boc removal, See 4.3c.1 and 5.2c.1 | 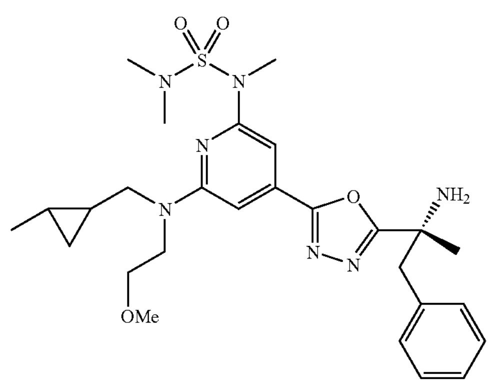 [SMILES: COCCN(CC1CC1C)c1cc(-c2nnc([C@](C)(N)Cc3ccccc3)o2)cc(N(C)S(=O)(=O)N(C)C)n1] | 557 |
| 5.2c.33 | 4.2c.22, Boc-D-alpha-methyl-phenylalanine | Coupling, cyclodehydration, Boc removal, See 4.3c.1 and 5.2c.1 | 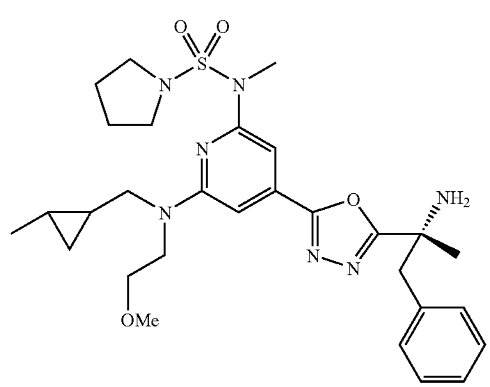 [SMILES: COCCN(CC1CC1C)c1cc(-c2nnc([C@](C)(N)Cc3ccccc3)o2)cc(N(C)S(=O)(=O)N2CCCC2)n1] | 583 |

TABLE I-continued

Oxadiazole Intermediates

| Int # | intermediates | Mode of prep | Structure | ES M + 1 |
|---|---|---|---|---|
| 5.2c.34 | 5.1.b1 | Pd coupling with N-cyclopentylmethanesulfonamide as in 4.2c.1 stepA, Boc removal | 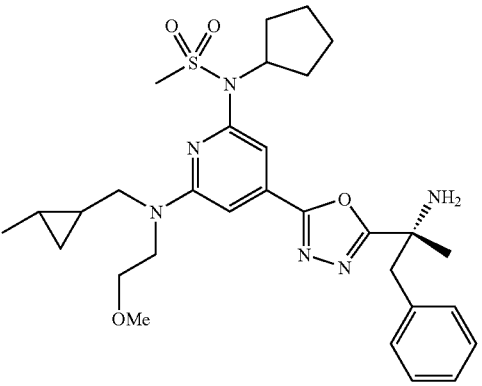 [SMILES: COCCN(CC1CC1C)c1cc(-c2nnc([C@](C)(N)Cc3ccccc3)o2)cc(N(C2CCCC2)S(C)(=O)=O)n1] | 582 |
| 5.2c.35 | 5.1.b1 | Pd coupling with N-cyclobutylmethanesulfonamide as in 4.2c.1 stepA, Boc removal | 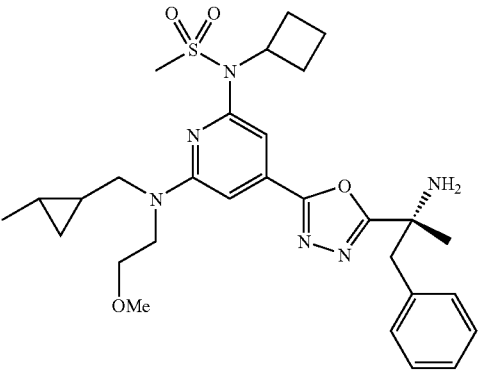 [SMILES: COCCN(CC1CC1C)c1cc(-c2nnc([C@](C)(N)Cc3ccccc3)o2)cc(N(C2CCC2)S(C)(=O)=O)n1] | 568 |
| 5.2c.36 | 5.1.b1 | Pd coupling with N-phenylsulfonamide as in 4.2c.1 stepA, Boc removal | 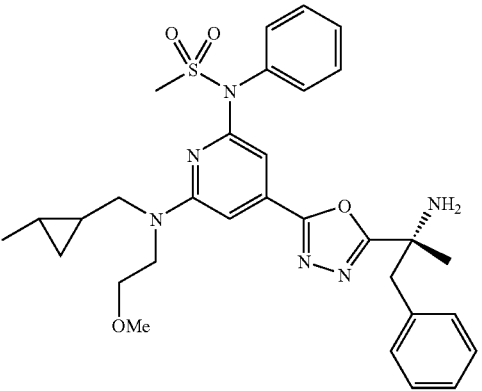 [SMILES: COCCN(CC1CC1C)c1cc(-c2nnc([C@](C)(N)Cc3ccccc3)o2)cc(N(c2ccccc2)S(C)(=O)=O)n1] | 590 |
| 10.1.1 | 4.2c.2, Boc-methyl alanine | Coupling, cyclodehydration, Boc removal, See 5.2c.1 | 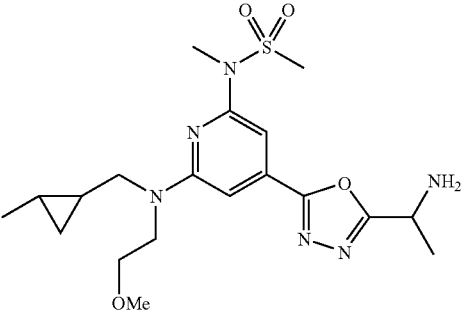 [SMILES: COCCN(CC1CC1C)c1cc(-c2nnc(C(C)N)o2)cc(N(C)S(C)(=O)=O)n1] | 439 |

Intermediate 6.2.1: [(1R)-1-(2-{2-(benzyl{[trans-2-methyl cyclopropyl]methyl}amino-6-[methyl(methylsulfonyl)amino]pyridin-4-yl}-1,3-oxazol-5-yl)-1-methyl-2-phenylethyl]carbamate

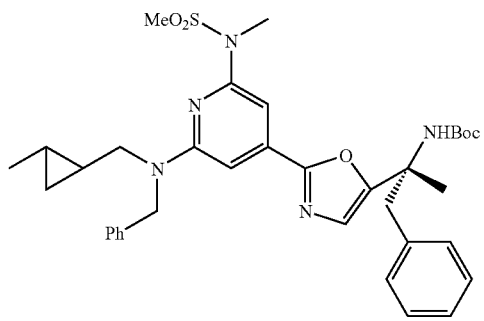 [SMILES: CC1CC1CN(Cc1ccccc1)c1cc(-c2ncc([C@@](C)(Cc3ccccc3)NC(=O)OC(C)(C)C)o2)cc(N(C)S(C)(=O)=O)n1]

Step A: Coupling

To a solution of Intermediate 4.2c.2 (0.452 g, 1.121 mmol) and Intermediate 2.3.1 (0.300 g, 1.019 mmol) in 12 mL DMF was added EDC (0.240 g, 1.253 mmol) and HOAt (0.153 g, 1.121 mmol). After 15 h, the reaction was diluted with H$_2$O and EtOAc, then washed with 10% KHSO$_4$, satd. NaHCO$_3$, 3M LiCl (3×) and brine. The organics were dried over Na$_2$SO$_4$, filtered and concentrated to afford tert-butyl [(1R)-1-benzyl-3-({2-(benzyl {[trans-(1S,2S)-2-methyl cyclopropyl]methyl}amino)-6-[methyl(methylsulfonyl)amino]isonicotinoyl}amino)-2-hydroxy-1-methylpropyl]carbamate as a mixture of two diastereomers, which was used without further purification. LCMS (M+H)=680.

Step B: Oxidation

To a solution of tert-butyl [(1R)-1-benzyl-3-({2-(benzyl {[trans-(1S,2s)-2-methyl cyclopropyl]methyl}amino)-6-[methyl(methylsulfonyl)amino]isonicotinoyl}amino)-2-hydroxy-1-methylpropyl]carbamate (0.693 g, 1.019 mmol) from Step A and triethylamine (0.426 mL, 3.058 mmol) in 10 mL CH$_2$Cl$_2$ was added sulfur trioxide pyridine complex (0.406 g, 2.55 mmol) in 2.5 mL DMSO After 15 h, the reaction was diluted with EtOAc, then washed with 10% aq. KHSO$_4$, satd. NaHCO$_3$, 3M LiCl and brine, then dried over Na$_2$SO$_4$, filtered and concentrated. The residue was purified using normal phase silica gel chromatography (10->40% EA/hex) to afford tert-butyl [(1R)-1-benzyl-3-({2-(benzyl {[trans-(1S,2S)-2-methylcyclopropyl]methyl}amino)-6-[methyl(methylsulfonyl)amino]isonicotinoyl}amino)-1-methyl-2-oxopropyl]carbamate as a white foam. $^1$H NMR (400 MHz, CDCl$_3$) δ 7.32-7.26 (m, 5H), 7.23-7.19 (m, 3H), 7.10 (d, J=11.7 Hz, 2H), 6.81 (s, 1H), 6.80 (s, 2H), 4.86 (m, 2H), 4.62 (m, 2H), 4.48 (m, 2H), 3.56 (m, 2H), 3.33-3.28 (m, 5H), 3.05 (d, J=13.7 Hz), 2.84 (s, 3H), 1.55 (s, 3H), 1.31 (s, 9H), 0.98 (d, J=5.9 Hz, 3H), 0.62 (m, 1H), 0.60 (m, 1H), 0.36 (m, 1H), 0.26 (m, 1H). LCMS (M+H)=678.

Step C: Dehydration

To a solution of tert-butyl [(1R)-1-benzyl-3-({2-(benzyl {[trans-(1S,2S)-2-methylcyclopropyl]methyl}amino)-6-[methyl(methylsulfonyl)amino]isonicotinoyl}amino)-1-methyl-2-oxopropyl]carbamate (0.230 g, 0.339 mmol) in 4 mL 1,2-dichloroethane was added methoxycarbonylsulfamoyl-triethylammonium hydroxide (0.485 g, 2.04 mmol, Burgess reagent). The reaction was microwaved at 100° C. for 40 min, then purified directly by normal phase silica gel chromatography (10->40% EtOAc/hex) to afford tert-butyl[(1R)-1-(2-{2-(benzyl {[(1S,2S)-2-methylcyclopropyl]methyl}amino)-6-[methyl(methylsulfonyl)amino]pyridin-4-yl}-1,3-oxazol-5-yl)-1-methyl-2-phenylethyl]carbamate as a white foam. $^1$H NMR (400 MHz, CDCl$_3$) ☐ 7.31-7.19 (m, 9H), 7.05-7.02 (m, 3H), 6.93 (s, 1H), 4.89 (m, 2H), 3.57 (dd, J=14.8, 5.9 Hz, 1H), 3.47 (m, 1H), 3.34-3.30 (m, 4H), 3.11 (d, J=13.2 Hz, 1H), 2.88 (s, 3H), 1.59 (s, 3H), 1.34 (s, 9H), 0.98 (d, J=5.9 Hz, 3H), 0.82 (m, 1H), 0.61 (m, 1H), 0.36 (m, 1H), 0.27 (m, 1H). LCMS (M+H)=660.

Intermediate 6.2.2: tert-butyl [(1R)-1-(2-{2-{(2-methoxyethyl)[(trans-2-methylcyclopropyl)methyl]amino}-6-[methyl(methylsulfonyl)amino]pyridin-4-yl}-1,3-oxazol-5-yl)-1-methyl-2-phenylethyl] carbamate

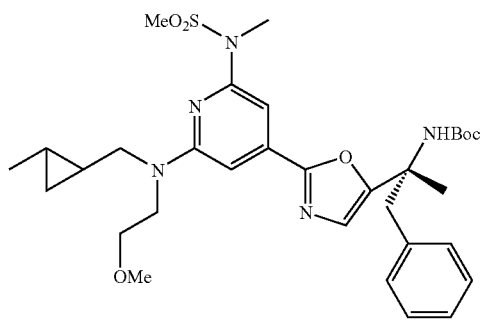 [SMILES: COCCN(CC1CC1C)c1cc(-c2ncc([C@@](C)(Cc3ccccc3)NC(=O)OC(C)(C)C)o2)cc(N(C)S(C)(=O)=O)n1]

Prepared from intermediates 4.2c.1 and 2.3.1 using a similar procedure as described in the preparation of intermediate 6.2.1. MS M+1=628.

Intermediate 8.4.1: N-{4-(5-{(1R)-1-[(tert-butoxycarbonyl)amino]-1-methyl-2-phenylethyl}-1,3,4-oxadiazol-2-yl)-6-[methyl(methylsulfonyl)amino] pyridin-2-yl}-N-[(trans-2-methylcyclopropyl) methyl]glycine (Scheme 8)

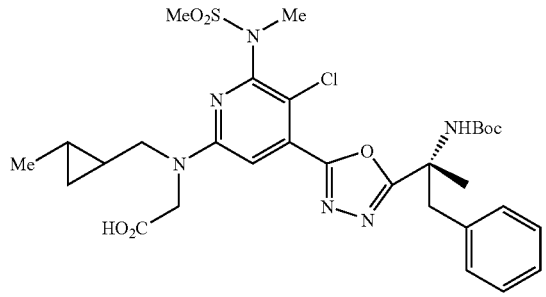 [SMILES: CC1CC1CN(CC(=O)O)c1cc(-c2nnc([C@@](C)(Cc3ccccc3)NC(=O)OC(C)(C)C)o2)c(Cl)c(N(C)S(C)(=O)=O)n1]

Step A: Chlorination.

In a flask charged with Intermediate 5.2c.22 (1.9 g, 3.41 mmol) in DCM (34 mL) at rt was added N-chlorosuccinimide (455 mg, 3.41 mmol). The reaction was stirred until disappearance of starting material as evident by LC/MS. At this time the mixture was concentrated to dryness and purified by RP-HPLC using an AcCN/H$_2$O linear gradient. Product containing fractions were pooled and freeze-dried to give 780 mg of the 3-chloro product: $^1$H NMR (CD$_3$OD, 400 MHz) δ 7.27 (m, 3H); 7.13 (s, 1H); 7.08 (m, 2H); 4.37 (s, 2H); 4.17 (q, J=7.1 Hz, 2H); 3.55 (dd, J=14.8, 5.9 Hz, 2H); 3.35 (m, 2H); 3.20 (s, 3H); 3.18 (s, 3H); 1.60 (s, 3H); 1.41 (s, 9H); 1.24 (t, J=7.1 Hz, 3H); 1.05 (d, J=6.7, 3H); 0.80 (m, 2H); 0.47 (m, 1H); 0.32 (m, 1H); LC/MS [M+H]=691.0

Step B: Hydrolysis.

The above intermediate from Step A (750 mg, 1.09 mmol) was dissolved in 11 mL THF. To this 5 mL 4.0 N LiOH was added. After stirring overnight the mixture was neutralized to pH 4.0 with 1N HCl. The mixture was repeatedly extracted with EtOAc (3×25 mL) and the combined layers sequentially washed with aqueous bicarbonate, water and brine. After drying over $Na_2SO_4$ and solvent removal under reduced pressure the title intermediate was obtained as a yellow foam: $^1$H NMR (CD$_3$OD, 400 MHz) δ 7.27 (m, 3H); 7.18 (m, 3H); 4.32 (s, 2H); 3.50 (m, 2H); 3.35 (m, 2H); 3.20 (s, 3H); 3.18 (s, 3H); 1.60 (s, 3H); 1.41 (s, 9H); 1.09 (d, J=6.3, 3H); 0.80 (m, 2H); 0.47 (m, 1H); 0.32 (m, 1H); LC/MS [M+H]=663.0.

Intermediate 8.4.2: tert-butyl [(1R)-1-(5-{2-{(2-methoxyethyl)[(trans-2-methylcyclopropyl)methyl]amino}-6-[(methylsulfonyl)amino]pyridin-4-yl}-1,3,4-oxadiazol-2-yl)-1-methyl-2-phenylethyl]carbamate (Scheme 8)

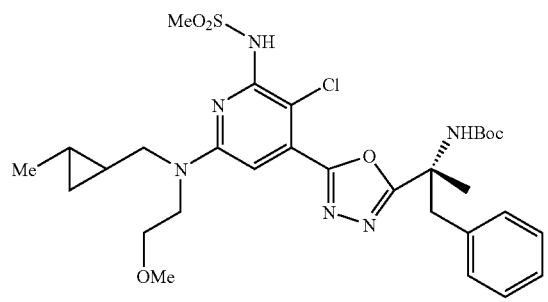 [SMILES: COCCN(CC1CC1C)c1cc(-c2nnc([C@@](C)(Cc3ccccc3)NC(=O)OC(C)(C)C)o2)c(Cl)c(NS(C)(=O)=O)n1]

Prepared from intermediate 5.1c.2 using NCS, as described in the preparation of intermediate 8.4.1. MS M+1=615.

Intermediate 9.1.1: 3-fluoro-6-{(2-methoxyethyl)[(trans-2-methylcyclopropyl)methyl]amino}-2-[methyl(methylsulfonyl)amino]isonicotinic acid (Scheme 9)

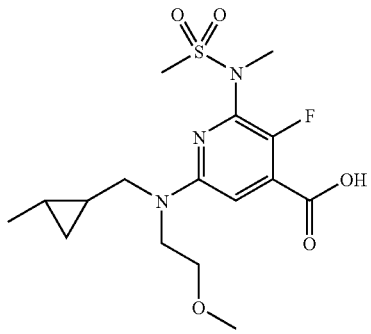 [SMILES: COCCN(CC1CC1C)c1cc(C(=O)O)c(F)c(N(C)S(C)(=O)=O)n1]

A solution of 2-{(2-methoxyethyl)[(2-methylcyclopropyl)methyl]amino}-6-[methyl(methylsulfonyl)amino]isonicotic acid (intermediate 4.2c.1, 0.05 g, 0.135 mmol) in acetonitrile (3 mL) was treated with 1-chloromethyl-4-fluoro-1,4-diazoniabicyclo[2.2.2]octane bis(tetrafluoroborate) (0.047 g, 0.134 mmol) and stirred at ambient temperature for 16 hr. The reaction was purified by reverse phase LC to give 3-fluoro-6-{(2-methoxyethyl)[(2-methylcyclopropyl)methyl]amino}-2-[methyl(methylsulfonyl)amino]isonicotinic acid as a pale yellow solid: LCMS [M+H]$^+$=390.3.

Intermediate 9.1.2: 6-{benzyl[(trans-2-methylcyclopropyl)methyl]amino}-3-fluoro-2-[methyl(methylsulfonyl)amino]isonicotinic acid (Scheme 9)

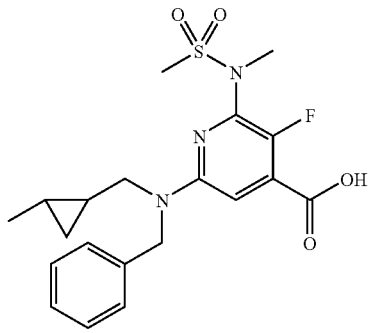 [SMILES: CC1CC1CN(Cc1ccccc1)c1cc(C(=O)O)c(F)c(N(C)S(C)(=O)=O)n1]

Prepared from intermediate 4.2c.2 using a similar procedure as described for the preparation of intermediate 9.1.1. MS M+1=422.

Intermediate 9.3.1: tert-butyl [(1R)-1-(5-{3-bromo-6-{[(trans-2-methylcyclopropyl)methyl]amino}-2-methyl(methylsulfonyl)amino]pyridin-4-yl}-1,3,4-oxadiazol-2-yl)-1-methyl-2-phenylethyl]carbamate (Scheme 9)

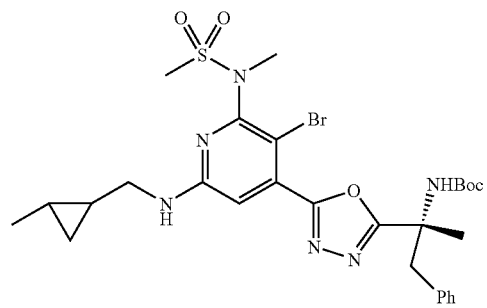 [SMILES: CC1CC1CNc1cc(-c2nnc([C@@](C)(Cc3ccccc3)NC(=O)OC(C)(C)C)o2)c(Br)c(N(C)S(C)(=O)=O)n1]

To a solution of tert-butyl [(1R)-1-methyl-1-(5-{2-{[(trans-2-methylcyclopropyl)methyl]amino}-6-[methyl(methylsulfonyl)amino]pyridin-4-yl}-1,3,4-oxadiazol-2-yl)-2-phenylethyl]carbamate (intermediate 5.2c.3 prior to Boc removal, 250 mg, 0.438 mmol) in 8 mL CH$_2$Cl$_2$ was added NBS (78 mg, 0.438 mmol). After 2 h, the reaction was concentrated and purified by normal phase silica gel chromatography (20->40% EtOAc/hexanes) to afford tert-butyl [(1R)-1-(5-{3-bromo-6-{[(trans-2-methylcyclopropyl)methyl]amino}-2-[methyl(methylsulfonyl)amino]pyridin-4-yl}-1,3,4-oxadiazol-2-yl)-1-methyl-2-phenylethyl]carbamate as a yellow solid. $^1$H NMR (CDCl$_3$, 400 MHz) δ 7.31-7.26 (m, 3H), 7.06-7.04 (m, 2H), 6.90 (s, 1H), 4.94 (m, 1H), 3.57 (d, J=13.2 Hz, 1H), 3.42 (d, J=13.1 Hz, 1H), 3.24 (s, 3H), 3.23 (s, 3H), 3.18 (m, 1H), 3.07 (m, 1H), 1.71 (s, 3H), 1.43 (s, 9H), 1.09 (d, J=6.0 Hz, 3H), 0.80 (m, 1H), 0.70 (m, 1H), 0.41 (m, 1H), 0.33 (m, 1H). LCMS (M+H)=649, 651 (Br pattern).

Intermediate 10.2.1: N-[3-chloro-4-(5-{1-[(diphenylmethylene)amino]ethyl}-1,3,4-oxadiazol-2-yl)-6-((3-methoxypropyl){trans-2-methylcyclopropyl]methyl}amino)pyridin-2-yl]-N-methylmethanesulfonamide (Scheme 10)

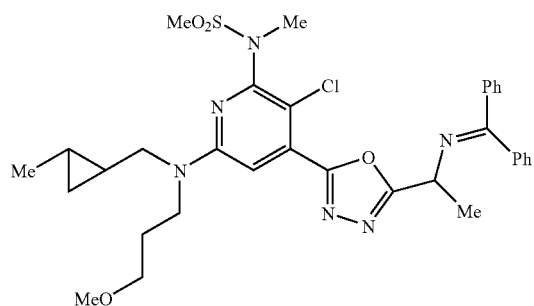 [SMILES: COCCCN(CC1CC1C)c1cc(-c2nnc(C(C)N=C(c3ccccc3)c3ccccc3)o2)c(Cl)c(N(C)S(C)(=O)=O)n1]

Step A: Chlorination

To a solution of N-[4-[5-(1-aminoethyl)-1,3,4-oxadiazol-2-yl]-6-((2-methoxyethyl) {[trans-2-methylcyclopropyl]methyl}amino)pyridin-2-yl]-N-methylmethanesulfonamide trifluoroacetate salt (intermediate 10.1.1, 3.600 g, 6.51 mmol) in 100 mL $CH_2Cl_2$ was added N-chlorosuccinimide (0.870 g, 6.51 mmol). After 12 h, the reaction was concentrated, and the resulting residue constituting a 3:1 mixture of the desired: undesired chlorine regioisomers was purified using preparative HPLC (Sunfire C18 Prep OBD column, 30×150 mm, 35 mL/min) to afford the desired compound. The fractions containing the desired chlorine regioisomer were partitioned between EtOAc and sat. $NaHCO_3$, the layers were separated, the organics were washed with brine and concentrated to afford N-[4-[5-(1-aminoethyl)-1,3,4-oxadiazol-2-yl]-3-chloro-6-((2-methoxyethyl) {[trans-2-methylcyclopropyl]methyl}amino)pyridin-2-yl]-N-methylmethanesulfonamide as a yellow foam. $^1H$ NMR (400 MHz, $CDCl_3$) δ 7.12 (s, 1H), 4.40 (br s, 1H), 3.71 (m, 2H), 3.54 (m, 2H), 3.43 (dd, J=14.8, 6 Hz, 1H), 3.33-3.28 (m, 4H), 3.24 (s, 3H), 3.19 (s, 3H), 1.61 (d, J=5.9 Hz, 3H), 1.02 (d, J=5.9 Hz, 3H), 0.74-0.64 (m, 2H), 0.41 (m, 1H), 0.29 (m, 1H). LCMS [M+H]$^+$=473 (chlorine pattern).

Step B: Hydrochloride Salt Formation

To a solution of N-[4-[5-(1-aminoethyl)-1,3,4-oxadiazol-2-yl]-3-chloro-6-((2-methoxyethyl){[trans-2-methylcyclopropyl]methyl}amino)pyridin-2-yl]-N-methylmethanesulfonamide (0.060 g, 0.102 mmol) in 1 mL $CH_2Cl_2$ at 0° C. was added 4M HCl in dioxane (0.038 mL, 0.153 mmol). The reaction was concentrated to afford N-[4-[5-(1-aminoethyl)-1,3,4-oxadiazol-2-yl]-3-chloro-6-((2-methoxyethyl){[trans-2-methylcyclopropyl]methyl}amino)pyridin-2-yl]-N-methylmethanesulfonamide hydrochloride as a yellow foam. LCMS [M+H]$^+$=473 (chlorine pattern).

Step B: Schiff Base Formation

To a solution of product (0.720 g, 1.413 mmol) from Step B in $CH_2Cl_2$ was added benzophenone imine (0.356 mL, 2.12 mmol). The reaction was allowed to proceed for 15 h at room temperature, then diluted with $H_2O$ and extracted with EtOAc (3×). The combined organics were washed with brine, dried over $Na_2SO_4$, filtered and concentrated. The residue was purified by silica gel chromatography (5->50% EtOAc/hex) to afford N-[4-(5-{1-[(diphenylmethylene)amino]ethyl}-1,3,4-oxadiazol-2-yl)-6-((2-methoxyethyl){[trans-2-methylcyclopropyl]methyl}amino)pyridin-2-yl]-N-methylmethanesulfonamide as a yellow foam. $^1H$ NMR (400 MHz, $CDCl_3$) δ 7.62 (d, J=7.1 Hz, 2H), 7.52-7.45 (m, 2H), 7.40-7.37 (m, 2H), 7.33-7.24 (m, 4H), 7.14 (s, 1H), 4.93 (q, J=6.4 Hz, 1H), 3.71 (m, 2H), 3.54 (t, J=6.1 Hz, 2H), 3.45-3.42 (m, 1H), 3.34-3.27 (m, 4H), 3.24 (s, 3H), 3.20 (s, 3H), 1.68 (d, J=6.6 Hz, 3H), 1.01 (d, J=5.9 Hz, 3H), 0.89-0.64 (m, 2H), 0.40 (m, 1H), 0.26 (m, 1H). LCMS [M+H]$^+$=637 (chlorine pattern).

EXAMPLE 1

N-(4-[5-(1R-amino-1-methyl-2-phenylethyl)-1,3,4-oxadiazol-2-yl]-3-chloro-6-{(trans-2-methoxyethyl)[(2-methylcyclopropyl)methyl]amino}pyridin-2-yl)-N-methylmethanesulfonamide (Scheme 8)

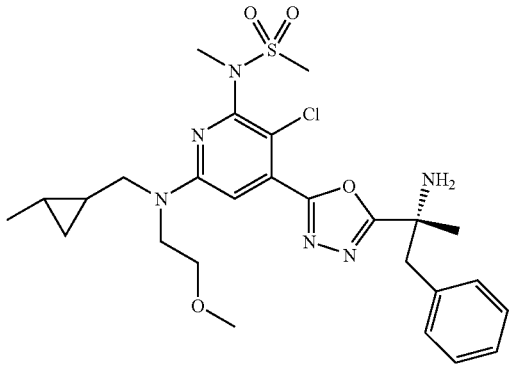 [SMILES: COCCN(CC1CC1C)c1cc(-c2nnc([C@](C)(N)Cc3ccccc3)o2)c(Cl)c(N(C)S(C)(=O)=O)n1]

A solution of N-(4-[5-(1R-amino-1-methyl-2-phenylethyl)-1,3,4-oxadiazol-2-yl]-6-{(2-methoxyethyl)[(trans-2-methylcyclopropyl)methyl]amino}pyridin-2-yl)-N-methylpropane-2-sulfonamide trifluoroacetate (Intermediate 5.2c.1, 10.77 g, 16.75 mmol) in DCM (145 mL) was treated with NCS (2.35 g, 17.6 mmol) and the solution was stirred at ambient temperature for 24 hr. An additional 115 mg of NCS was added and the reaction was stirred at ambient temperature for 8 hr. The reaction was evaporated in vacuo and purified by reverse phase HPLC to give N-(4-[5-(1R-amino-1-methyl-2-phenylethyl)-1,3,4-oxadiazol-2-yl]-3-chloro-6-{(2-methoxyethyl)[(2-methylcyclopropyl)methyl]amino}pyridin-2-yl)-N-methylmethanesulfonamide trifluoroacetate as a pale yellow solid: $^1H$ NMR (400 MHz, $CD_3OD$) δ 7.34 (t, J=3.11, 3H), 7.12 (s, 1H), 7.08 (m, 2H), 3.79 (t, J=5.9 Hz, 2H), 3.62 (t, J=5.7 Hz, 2H), 3.53 (dd, J=14.8, 5.9 Hz, 1H), 3.44 (s, 2H), 3.40 (dd, J=15.0, 7.0 Hz, 1H), 3.34 (s, 3H), 3.26 (s, 3H), 3.24 (s, 3H), 1.87 (s, 3H), 1.05 (d, J=5.9 Hz, 3H), 0.79 (m, 2H), 0.49 (m, 1H), 0.31 (m, 1H). LCMS [M+H]$^+$=563.3.

Use of the preferred enantiomer trans-S,S from Intermediate 3.2.1, step A, affords the preparation of the preferred enantiopure S,S,R example.

EXAMPLE 2

N-(4-{5-[(1R)-1-amino-2-(4-fluorophenyl-1-methyl-ethyl]-1,3,4-oxadiazol-2-yl}-3-chloro-6-{(2-methoxyethyl)[(2-methylcyclopropyl)methyl]amino}pyridin-2-yl)-N-methylmethanesulfonamide
(Scheme 8)

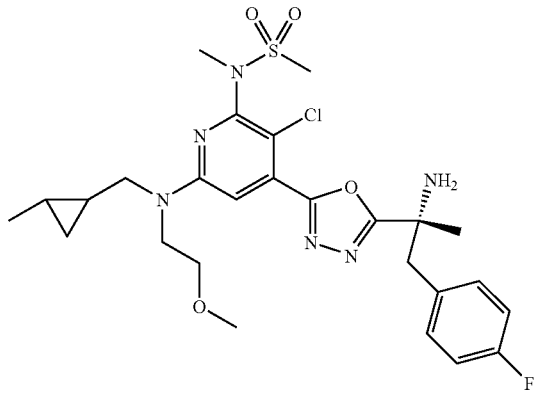 [SMILES: COCCN(CC1CC1C)c1cc(-c2nnc([C@](C)(N)Cc3ccc(F)cc3)o2)c(Cl)c(N(C)S(C)(=O)=O)n1]

A solution of N-(4-{5-[(1R)-1-amino-2-(4-fluorophenyl)-1-methylethyl]-1,3,4-oxadiazol-2-yl}-6-{(2-methoxyethyl)[(trans-2-methylcyclopropyl)methyl]amino}pyridin-2-yl)-N-methylmethanesulfonamide trifluoroacetate (Intermediate 5.2c.2, 9.79 g, 17.9 mmol) in DCM (250 mL) was treated with NCS (2.39 g, 17.9 mmol) and the solution was stirred at ambient temperature for 60 hr. An additional 360 mg of NCS was added in three portions over 72 hr while the reaction was stirred at ambient temperature. The reaction was evaporated in vacuo and purified by reverse phase HPLC to isolate the desired chlorine isomer. The material was purified further by flash chromatography (silica, 0% to 3% isopropanol in $CHCl_3$) to give N-(4-{5-[(1R)-1-amino-2-(4-fluorophenyl)-1-methylethyl]-1,3,4-oxadiazol-2-yl}-3-chloro-6-{(2-methoxyethyl)[(2-methylcyclopropyl)methyl]amino}pyridin-2-yl)-N-methylmethanesulfonamide: $^1$H NMR (400 MHz, $CDCl_3$) δ 7.13 (s, 1H), 7.02 (m, 2H), 6.93 (m, 2H), 3.74 (t, J=6.05, 2H), 3.57 (t, J=6.04, 2H), 3.41 (AB overlapping m, 5H), 3.28 (m, 4H), 3.22 (s, 3H), 3.07 (B of AB overlapping m, 1H), 1.86 (s, 2H), 1.64 (s, 3H), 1.05 (d, J=5.86, 3H), 0.78-0.67 (m, 2H), 0.43 (m, 1H), 0.31 (m, 1H). LCMS $[M+H]^+$=581.0.

Additional 3-Cl substituted pyridyl derivatives with an oxadiazole group were prepared as described below in Table 2.

TABLE 2

| | | 3-Cl Derivatives | | |
|---|---|---|---|---|
| Ex # | intermediate | Mode of prep | structure | ES M + 1 |
| 3 | 5.2c.3 | Ex 1 | | 505 |
| 4 | 5.2c.4 | Ex 1 | | 523 |

TABLE 2-continued
3-Cl Derivatives
| Ex # | intermediate | Mode of prep | structure | ES M + 1 |
|---|---|---|---|---|
| 5 | 5.2c.5 | Ex 1 | 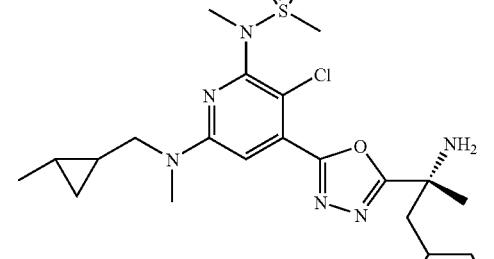 | 519 |
| 6 | 5.2c.6 | Ex 1 | 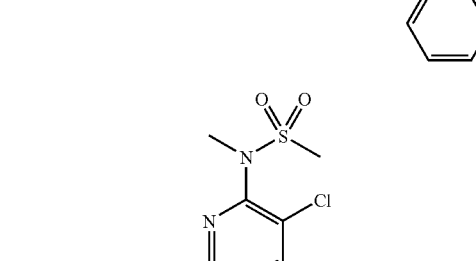 | 537 |
| 7 | 5.2c.7 | Ex 1 | 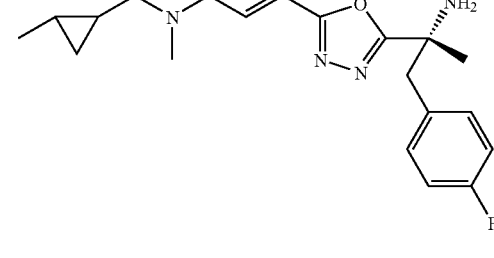 | 613 |
| 8 | 5.2c.8 | Ex 1 | 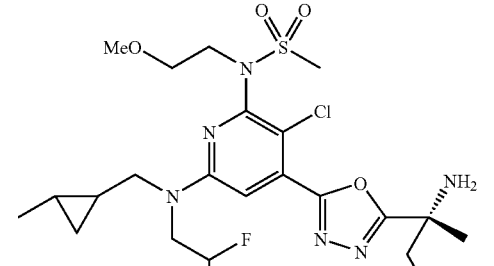 | 607 |

TABLE 2-continued

| | | | 3-Cl Derivatives | |
|---|---|---|---|---|
| Ex # | intermediate | Mode of prep | structure | ES M + 1 |
| 9 | 5.2c.9 | Ex 1 | | 563 |
| 10 | 5.2c.10 | Ex 1 | | 575 |
| 11 | 5.2c.11 | Ex 1 | | 517 |
| 12 | 5.2c.12 | Ex 1 | | 549 |

TABLE 2-continued

| 3-Cl Derivatives | | | | |
|---|---|---|---|---|
| Ex # | intermediate | Mode of prep | structure | ES M + 1 |
| 13 | 5.2c.13 | Ex 1 | | 519 |
| 14 | 5.2c.14 | Ex 1 | | 533 |
| 15 | 5.2c.15 | Ex 1 | | 519 |
| 16 | 5.2c.16 | Ex 1 | | 505 |

TABLE 2-continued

| | | | 3-Cl Derivatives | |
|---|---|---|---|---|
| Ex # | intermediate | Mode of prep | structure | ES M + 1 |
| 17 | 5.2c.17 | Ex 1 | | 607 |
| 18 | 5.2c.18 | Ex 1 | | 651 |
| 19 | 5.2c.19 | Ex 1 | | 599 |

TABLE 2-continued

| | | 3-Cl Derivatives | | |
|---|---|---|---|---|
| Ex # | intermediate | Mode of prep | structure | ES M + 1 |
| 20 | 5.2c.20 | Ex 1 | | 599 |
| 21 | 5.2c.21 | Ex 1 | | 599 |
| 22 | 5.2c.22 | Ex 1 | | 591 |
| 22a | 8.4.1 | Boc Removal | | 563 |

TABLE 2-continued

3-Cl Derivatives

| Ex # | intermediate | Mode of prep | structure | ES M + 1 |
|---|---|---|---|---|
| 23 | 5.2c.23 | Ex 1 | 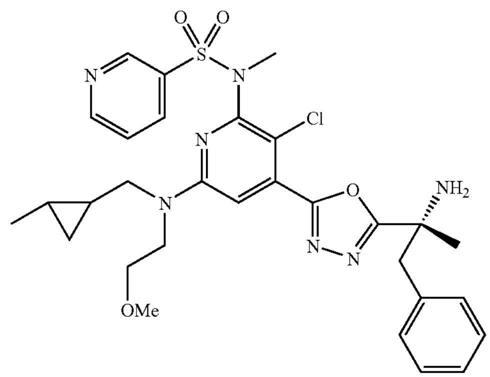 [SMILES: COCCN(CC1CC1C)c1cc(-c2nnc([C@](C)(N)Cc3ccccc3)o2)c(Cl)c(N(C)S(=O)(=O)c2cccnc2)n1] | 626 |
| 24 | 5.2c.24 | Ex 1 | 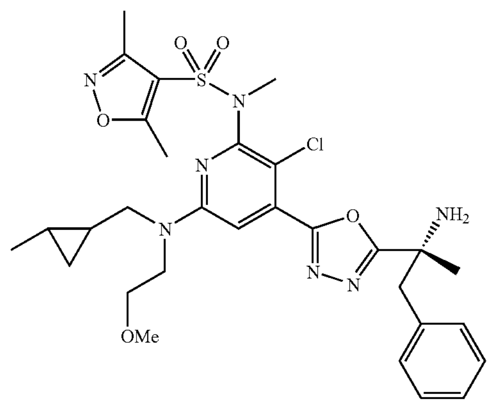 [SMILES: COCCN(CC1CC1C)c1cc(-c2nnc([C@](C)(N)Cc3ccccc3)o2)c(Cl)c(N(C)S(=O)(=O)c2c(C)noc2C)n1] | 644 |
| 25 | 5.2c.25 | Ex 1 | 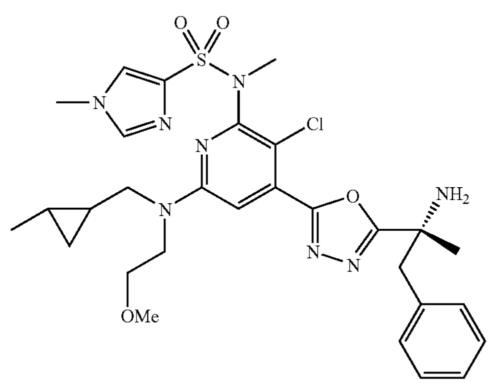 [SMILES: COCCN(CC1CC1C)c1cc(-c2nnc([C@](C)(N)Cc3ccccc3)o2)c(Cl)c(N(C)S(=O)(=O)c2cn(C)cn2)n1] | 629 |
| 26 | 5.2c.26 | Ex 1 | 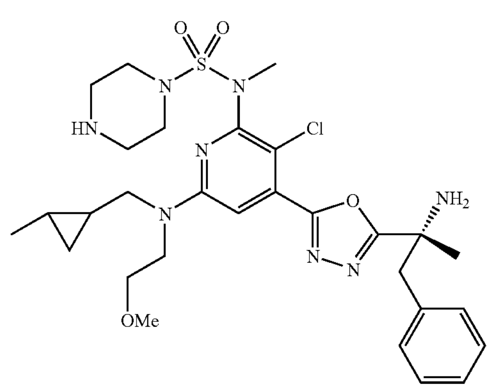 [SMILES: COCCN(CC1CC1C)c1cc(-c2nnc([C@](C)(N)Cc3ccccc3)o2)c(Cl)c(N(C)S(=O)(=O)N2CCNCC2)n1] | 633 |

TABLE 2-continued

3-Cl Derivatives

| Ex # | intermediate | Mode of prep | structure | ES M + 1 |
|---|---|---|---|---|
| 27 | 5.2c.27 | Ex 1 | 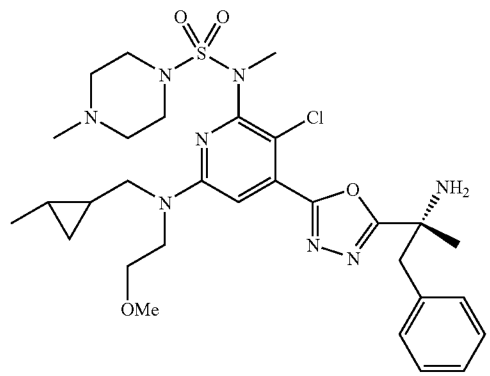 [SMILES: COCCN(CC1CC1C)c1cc(-c2nnc([C@](C)(N)Cc3ccccc3)o2)c(Cl)c(N(C)S(=O)(=O)N2CCN(C)CC2)n1] | 647 |
| 28 | 5.2c.28 | Ex 1 | 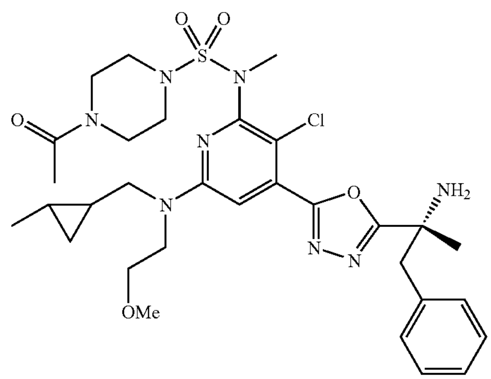 [SMILES: COCCN(CC1CC1C)c1cc(-c2nnc([C@](C)(N)Cc3ccccc3)o2)c(Cl)c(N(C)S(=O)(=O)N2CCN(C(C)=O)CC2)n1] | 675 |
| 29 | 5.2c.29 | Ex 1 | 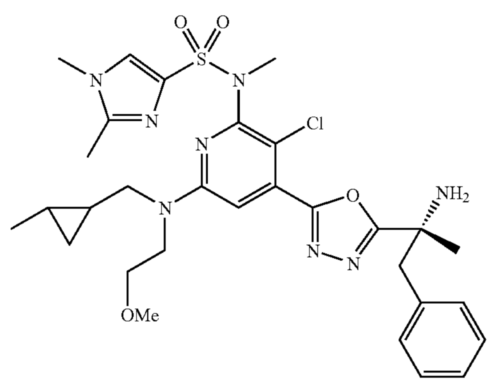 [SMILES: COCCN(CC1CC1C)c1cc(-c2nnc([C@](C)(N)Cc3ccccc3)o2)c(Cl)c(N(C)S(=O)(=O)c2cn(C)c(C)n2)n1] | 643 |
| 30 | 5.2c.30 | Ex 1 | 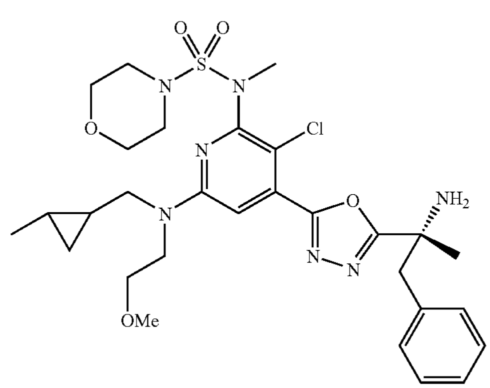 [SMILES: COCCN(CC1CC1C)c1cc(-c2nnc([C@](C)(N)Cc3ccccc3)o2)c(Cl)c(N(C)S(=O)(=O)N2CCOCC2)n1] | 634 |

TABLE 2-continued

3-Cl Derivatives

| Ex # | intermediate | Mode of prep | structure | ES M + 1 |
|---|---|---|---|---|
| 31 | 5.2c.31 | Ex1 | 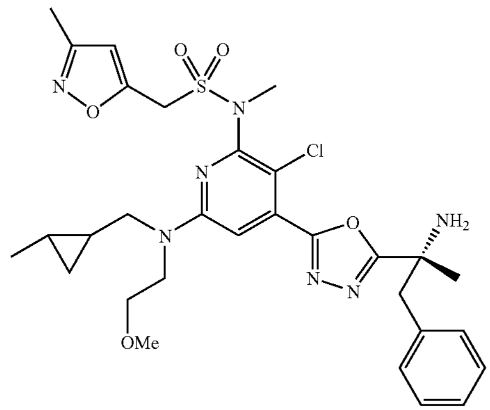 [SMILES: COCCN(CC1CC1C)c1cc(-c2nnc([C@](C)(N)Cc3ccccc3)o2)c(Cl)c(N(C)S(=O)(=O)Cc2cc(C)no2)n1] | 644 |
| 32 | 5.2c.32 | Ex 1 | 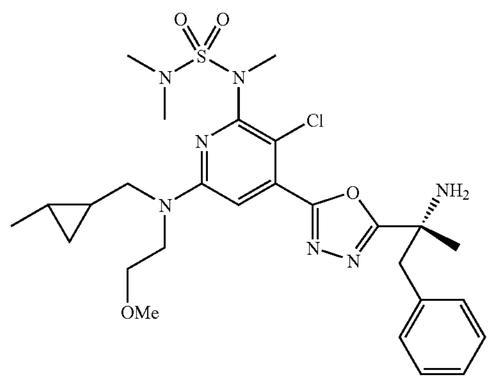 [SMILES: COCCN(CC1CC1C)c1cc(-c2nnc([C@](C)(N)Cc3ccccc3)o2)c(Cl)c(N(C)S(=O)(=O)N(C)C)n1] | 592 |
| 33 | 5.2c.33 | Ex 1 | 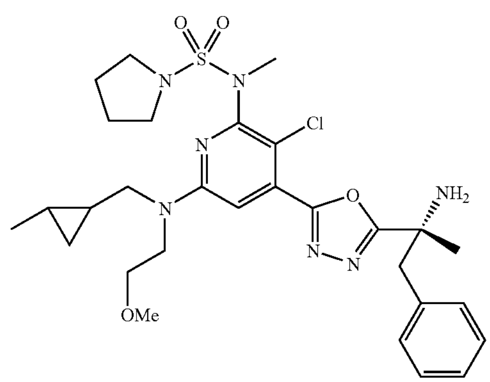 [SMILES: COCCN(CC1CC1C)c1cc(-c2nnc([C@](C)(N)Cc3ccccc3)o2)c(Cl)c(N(C)S(=O)(=O)N2CCCC2)n1] | 618 |
| 34 | 5.2c.34 | Ex 1 | 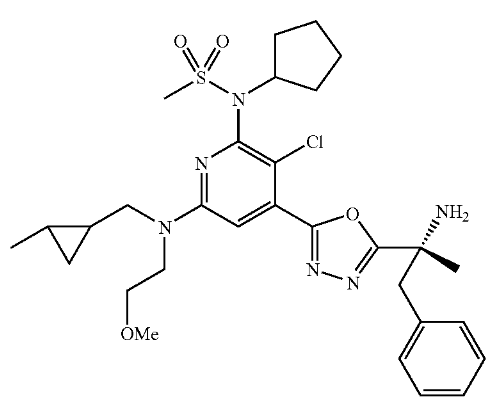 [SMILES: COCCN(CC1CC1C)c1cc(-c2nnc([C@](C)(N)Cc3ccccc3)o2)c(Cl)c(N(C2CCCC2)S(C)(=O)=O)n1] | 617 |

TABLE 2-continued

3-Cl Derivatives

| Ex # | intermediate | Mode of prep | structure | ES M + 1 |
|---|---|---|---|---|
| 35 | 5.2c.35 | Ex 1 | 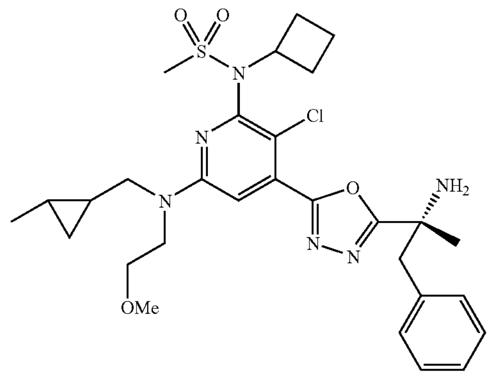 [SMILES: COCCN(CC1CC1C)c1cc(-c2nnc([C@](C)(N)Cc3ccccc3)o2)c(Cl)c(N(C2CCC2)S(C)(=O)=O)n1] | 603 |
| 36 | 5.2c.36 | Ex 1 | 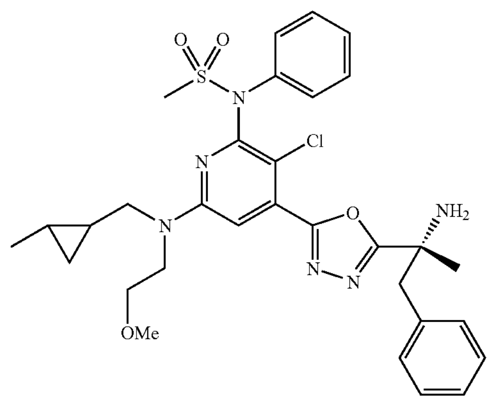 [SMILES: COCCN(CC1CC1C)c1cc(-c2nnc([C@](C)(N)Cc3ccccc3)o2)c(Cl)c(N(c2ccccc2)S(C)(=O)=O)n1] | 625 |

EXAMPLE 37

N-(4-{[(1R)-1-amino-1-methyl-2-phenylethyl]-1,3,4-oxadiazol-2-yl}-3-chloro-6-{(2-methoxyethyl)[(trans-2-methylcyclopropyl)methyl]amino}pyridin-2-yl)-N-methyl-1 pyridin-2-ylmethanesulfonamide

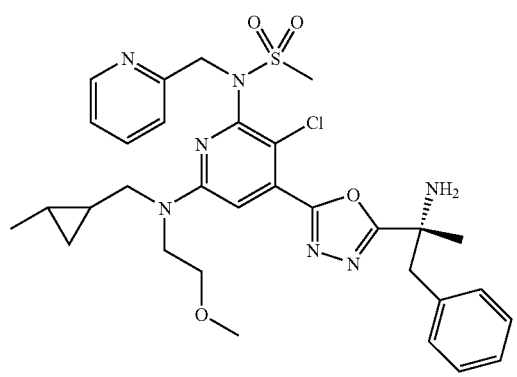 [SMILES: COCCN(CC1CC1C)c1cc(-c2nnc([C@](C)(N)Cc3ccccc3)o2)c(Cl)c(N(Cc2ccccn2)S(C)(=O)=O)n1]

Step A: Mitsunobu

To a solution of tert-butyl (1R)-1-(5-{3-chloro-6-((2-methoxyethyl){[trans-2-methylcyclopropyl]methyl} amino)-2-[(methylsulfonyl)amino]pyridin-4-yl}-1,3,4-oxadiazol-2-yl)-1-methyl-2-phenylethylcarbamate (intermediate 8.4.2, 0.028 g, 0.043 mmol) in toluene (1 ml) at 0 oC was added 2-(hydroxymethyl)pyridine (0.004 ml, 0.043 mmol) and triphenylphosphine (0.011 g, 0.043 mmol) followed by diisopropyl azodicarboxylate (0.008 ml, 0.043 mmol). The ice bath was removed and the solution stirred at room temperature overnight. The next day the solution was concentrated in vacuo, taken up in DMF and filtered. The product was purified by reverse phase HPLC affording 0.015 g of tert-butyl (1R)-1-(5-{3-chloro-6-((2-methoxyethyl){[trans-2-methylcyclopropyl]methyl}amino)-2[(methylsulfonyl)(pyridin-2-ylmethyl)amino]pyridin-4-yl}-1,3,4-oxadiazol-2-yl)-1-methyl-2-phenylethylcarbamate LCMS [M+H] 740.2.

Step B: Boc Removal

To a solution of tert-butyl (1R)-1-(5-{3-chloro-6-((2-methoxyethyl) {[trans-2-methylcyclopropyl]methyl} amino)- 2-[(methylsulfonyl)(pyridin-2-ylmethyl)amino]pyridin-4-yl}-1,3,4-oxadiazol-2-yl)-1-methyl-2-phenylethylcarbamate in CH$_2$Cl$_2$ (1 ml) was added TFA (0.5 ml) and stirred for 30 minutes at rt. Evaporation of the solvent afforded 0.008 g of N-[4-{5-[(1R)-1-amino-1-methyl-2-phenylethyl]-1,3,4-oxadiazol-2-yl}-3-chloro-6-((2-methoxyethyl) {[trans-2-methylcyclopropyl]methyl}amino)pyridin-2-yl]-N-(pyridin-2-ylmethyl)methanesulfonamide. LCMS [M+H]640.2 Exact mass calculated for C$_{31}$H$_{38}$ClN$_7$O$_4$S: 640.2468; measured 640.2484

TABLE 3
| | | | 3-Cl Derivatives | |
|---|---|---|---|---|
| Ex # | intermediate | Mode of prep | structure | ES M + 1 |
| 38 | 8.4.2 | Ex 37, Mitsunobu with 3-hydroxymethylpyridine | 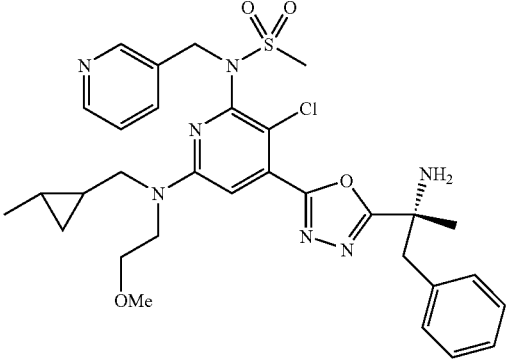 [SMILES: COCCN(CC1CC1C)c1cc(-c2nnc([C@](C)(N)Cc3ccccc3)o2)c(Cl)c(N(Cc2cccnc2)S(C)(=O)=O)n1] | 640 |
| 39 | 8.4.2 | Ex 37, Mitsunobu with [(2S)-1-methylpyrrolidin-2-yl]methanol | 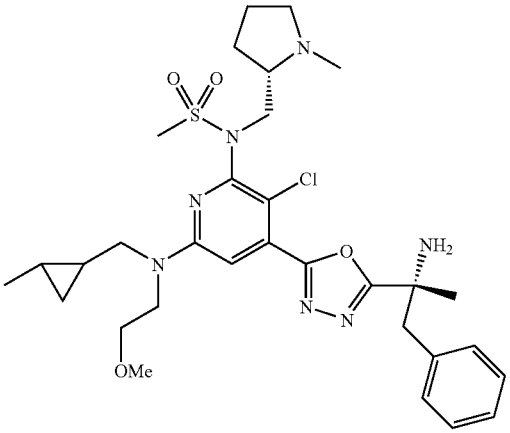 [SMILES: COCCN(CC1CC1C)c1cc(-c2nnc([C@](C)(N)Cc3ccccc3)o2)c(Cl)c(N(C[C@@H]2CCCN2C)S(C)(=O)=O)n1] | 646 |
| 40 | 8.4.2 | Ex 37, Mitsunobu with (3,5-dimethylisoxazol-4-yl)methanol | 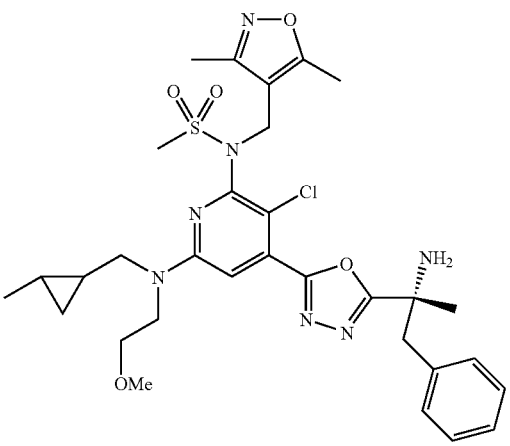 [SMILES: COCCN(CC1CC1C)c1cc(-c2nnc([C@](C)(N)Cc3ccccc3)o2)c(Cl)c(N(Cc2c(C)noc2C)S(C)(=O)=O)n1] | 658 |

TABLE 3-continued
3-Cl Derivatives
| Ex # | intermediate | Mode of prep | structure | ES M + 1 |
|---|---|---|---|---|
| 41 | 8.4.2 | Ex 37, Mitsunobu with (5-methylisoxazol-3-yl)methanol | 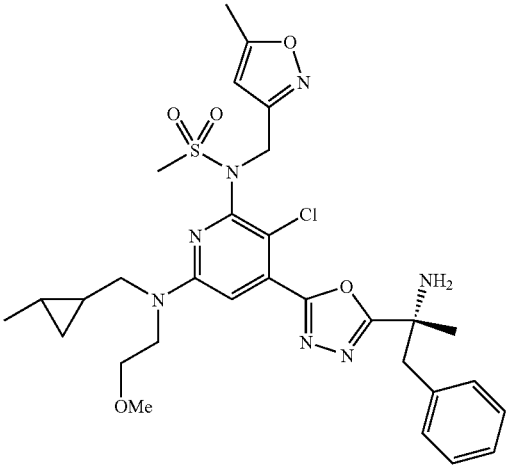 [SMILES: COCCN(CC1CC1C)c1cc(-c2nnc([C@](C)(N)Cc3ccccc3)o2)c(Cl)c(N(Cc2cc(C)on2)S(C)(=O)=O)n1] | 644 |
| 42 | 8.4.2 | Ex 37, Mitsunobu with 2-morpholin-4-ylethanol | 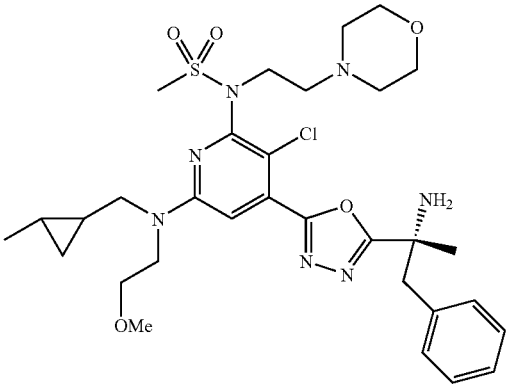 [SMILES: COCCN(CC1CC1C)c1cc(-c2nnc([C@](C)(N)Cc3ccccc3)o2)c(Cl)c(N(CCN2CCOCC2)S(C)(=O)=O)n1] | 662 |
| 43 | 8.4.2 | Ex 37, alkylation with bromoacetonitrile instead of step A | 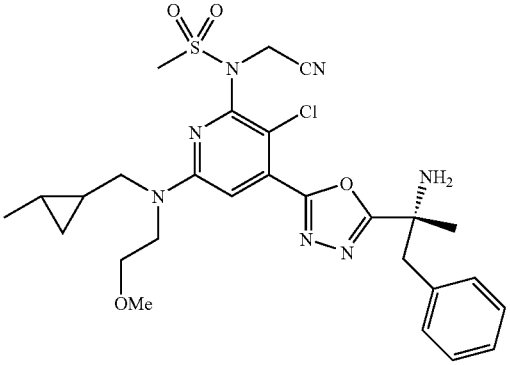 [SMILES: COCCN(CC1CC1C)c1cc(-c2nnc([C@](C)(N)Cc3ccccc3)o2)c(Cl)c(N(CC#N)S(C)(=O)=O)n1] | 588 |

TABLE 3-continued
3-Cl Derivatives
| Ex # | intermediate | Mode of prep | structure | ES M + 1 |
|---|---|---|---|---|
| 44 | Ex 43, prior to Boc removal | TMS-N₃ on nitrile, Boc removal | 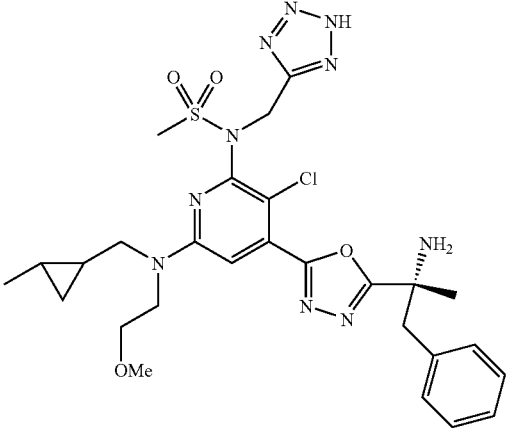 [SMILES: COCCN(CC1CC1C)c1cc(-c2nnc([C@](C)(N)Cc3ccccc3)o2)c(Cl)c(N(Cc2nn[nH]n2)S(C)(=O)=O)n1] | 631 |
| 45 | Ex 44, prior to Boc removal | Alkylation of tetrazole with MeI, Boc removal | 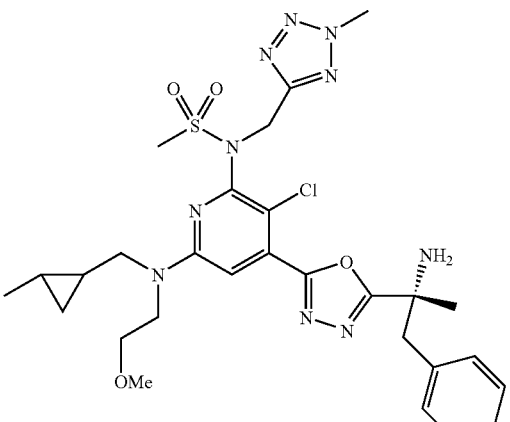 | 645 |
| 46 | Ex 44, prior to Boc removal | Alkylation of tetrazole with MeI, Boc removal | 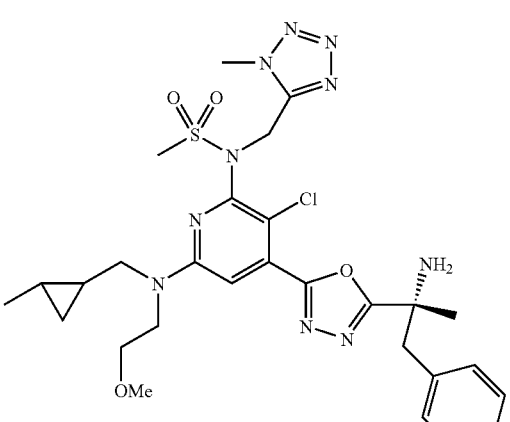 | 645 |

TABLE 3-continued

3-Cl Derivatives

| Ex # | intermediate | Mode of prep | structure | ES M + 1 |
|---|---|---|---|---|
| 47 | 8.4.2 | Ex 37, alkylation with ethyl bromoacetate instead of step A, ester reduction, Boc removal | 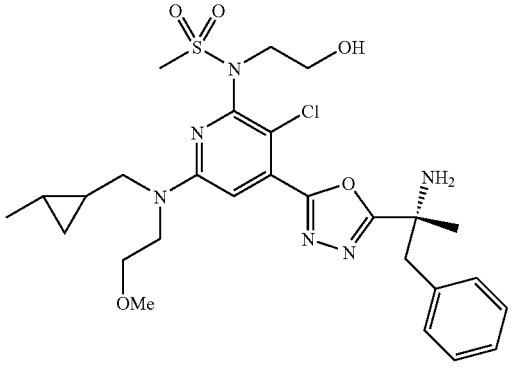 [SMILES: COCCN(CC1CC1C)c1cc(-c2nnc([C@](C)(N)Cc3ccccc3)o2)c(Cl)c(N(CCO)S(C)(=O)=O)n1] | 593 |
| 48 | 8.4.2 | Ex 37, alkylation with propargyl bromide instead of step A, TMS-$N_3$ on acetylene, Boc removal | 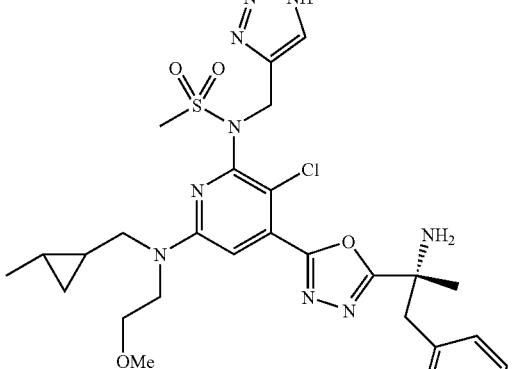 | 630 |

N-(4-{5-[1-amino-2-(3,5-dibromophenyl)-1-methylethyl]-1,3,4-oxadiazol-2-yl}-3-chloro-6-{(2-methoxyethyl)[(trans-2-methylcyclopropyl)methyl]amino}pyridin-2-yl)-N-methylmethanesulfonamide (Scheme 10)

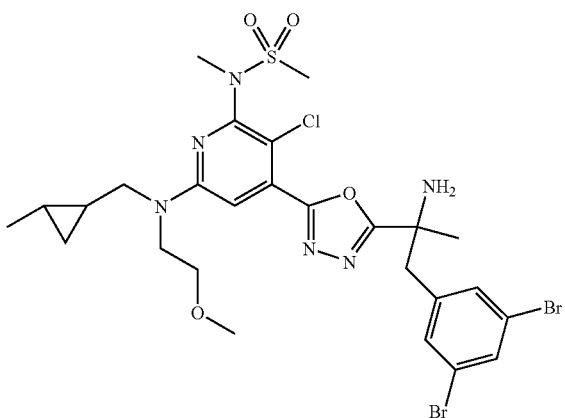 [SMILES: COCCN(CC1CC1C)c1cc(-c2nnc(C(C)(N)Cc3cc(Br)cc(Br)c3)o2)c(Cl)c(N(C)S(C)(=O)=O)n1]

To a solution of N-[4-(5-{1-[(diphenylmethylene)amino]ethyl}-1,3,4-oxadiazol-2-yl)-6-((2-methoxyethyl) {[trans-(1S,2S)-2-methylcyclopropyl]methyl}amino)pyridin-2-yl]-N-methylmethanesulfonamide (0.106 g, 0.162 mmol) in 2 mL DMF at 0° C. was added 1M NaHMDS in THF (0.211 mL, 0.211 mmol). After 5 min, 3,5-dibromobenzyl bromide (0.072 g, 0.219 mmol) in 1 mL DMF was added via cannula to the deep blue solution, which turned yellow upon completion of cannulation. After 30 min, 1 mL 1N HCl was added, and the reaction was allowed to proceed for 15 h to complete Schiff base hydrolysis. The reaction was poured onto a 10 g SCX ion exchange cartridge, which was eluted with 150 mL MeOH, followed by 150 mL 2M $NH_3$ in MeOH to afford analytically pure N-[4-{5-[(1R)-1-amino-2-(3,5-dibromophenyl)-1-methylethyl]-1,3,4-oxadiazol-2-yl}-3-chloro-6-((2-methoxyethyl){[trans-(1S,2S)-2-methylcyclopropyl]methyl}amino)pyridin-2-yl]-N-methylmethanesulfonamide as a yellow foam. The diastereomers resulting from this alkylation could be separated using a ChiralPak AD chiral stationary phase. $^1$H NMR (400 MHz, $CDCl_3$) δ 7.55 (s, J=7.1 Hz, 1H), 7.17 (s, 2H), 7.04 (s, 1H), 3.71 (m, 2H), 3.52 (t, J=5.9 Hz, 2H), 3.42 (dd, J=14.8, 5.7 Hz, 1H), 3.33-3.29 (m, 4H), 3.24 (s, 3H), 3.19 (s, 3H), 1.80 (s, 3H), 1.01 (d, J=5.9 Hz, 3H), 0.72-0.65 (m, 2H), 0.40 (m, 1H), 0.28 (m, 1H). LCMS [M+H]$^+$=721 (complex pattern). Exact mass calculated for $C_{26}H_{34}Br_2ClN_6O_4S$: 719.0412; measured: 719.0446.

Additional 3-Cl substituted pyridyl derivatives with an oxadiazole group and alternative Q-$R_1$, groups were prepared as described below in Table 3, using appropriate alkylating agents.

TABLE 4

3-Cl Derivatives

| Ex # | intermediate | Mode of prep | structure | ES M + 1 |
|------|--------------|--------------|-----------|----------|
| 50 | 10.2.1 | Ex 49 | 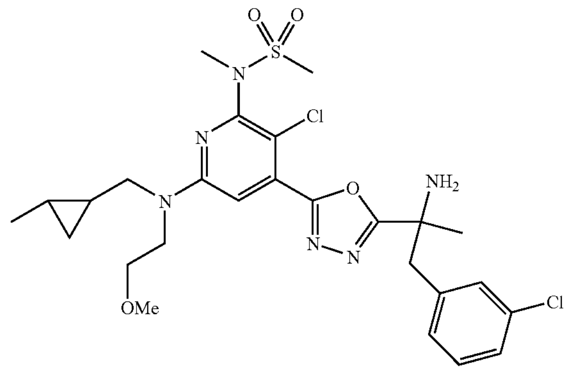 [SMILES: COCCN(CC1CC1C)c1cc(-c2nnc(C(C)(N)Cc3cccc(Cl)c3)o2)c(Cl)c(N(C)S(C)(=O)=O)n1] | 597 |
| 51 | 10.2.1 | Ex 49 | 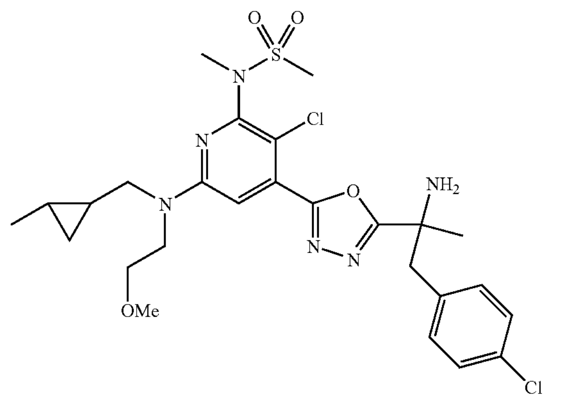 [SMILES: COCCN(CC1CC1C)c1cc(-c2nnc(C(C)(N)Cc3ccc(Cl)cc3)o2)c(Cl)c(N(C)S(C)(=O)=O)n1] | 597 |
| 52 | 10.2.1 | Ex 49 | 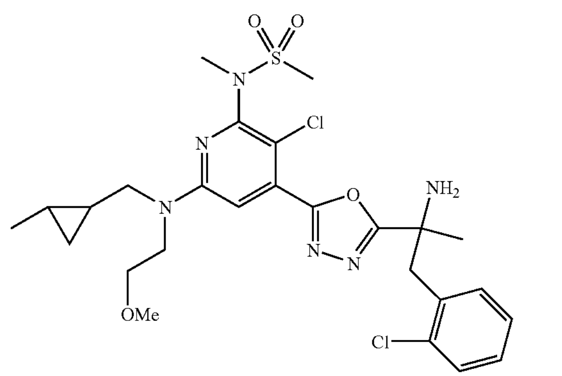 [SMILES: COCCN(CC1CC1C)c1cc(-c2nnc(C(C)(N)Cc3ccccc3Cl)o2)c(Cl)c(N(C)S(C)(=O)=O)n1] | 597 |
| 53 | 10.2.1 | Ex 49 | 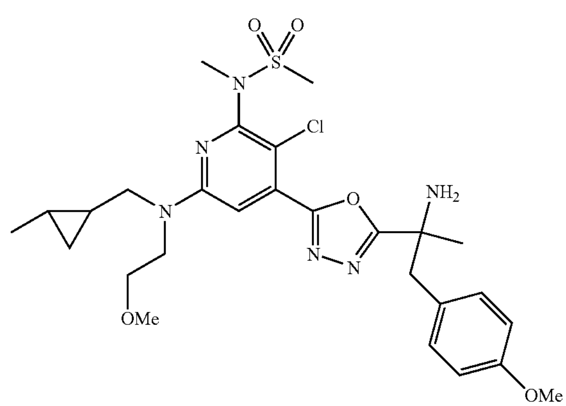 [SMILES: COCCN(CC1CC1C)c1cc(-c2nnc(C(C)(N)Cc3ccc(OC)cc3)o2)c(Cl)c(N(C)S(C)(=O)=O)n1] | 593 |

TABLE 4-continued

| | | | 3-Cl Derivatives | |
|---|---|---|---|---|
| Ex # | intermediate | Mode of prep | structure | ES M + 1 |
| 54 | 10.2.1 | Ex 49 | | 593 |
| 55 | 10.2.1 | Ex 49 | | 593 |
| 56 | 10.2.1 | Ex 49 | | 607 |
| 57 | 10.2.1 | Ex 49 | | 581 |

TABLE 4-continued

3-Cl Derivatives

| Ex # | intermediate | Mode of prep | structure | ES M + 1 |
|---|---|---|---|---|
| 58 | 10.2.1 | Ex 49 | 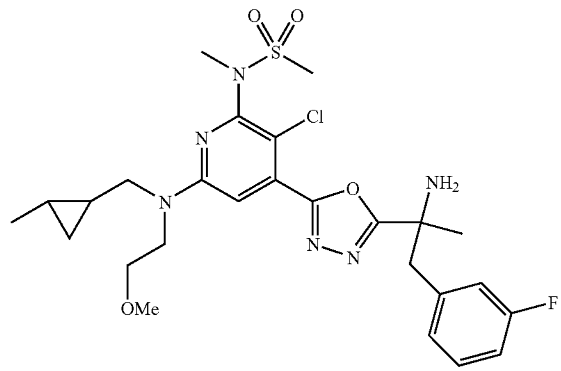 [SMILES: COCCN(CC1CC1C)c1cc(-c2nnc(C(C)(N)Cc3cccc(F)c3)o2)c(Cl)c(N(C)S(C)(=O)=O)n1] | 581 |
| 59 | 10.2.1 | Ex 49 | 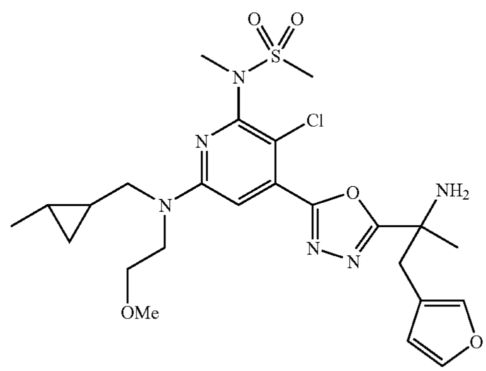 [SMILES: COCCN(CC1CC1C)c1cc(-c2nnc(C(C)(N)Cc3ccoc3)o2)c(Cl)c(N(C)S(C)(=O)=O)n1] | 553 |
| 60 | 10.2.1 | Ex 49 | 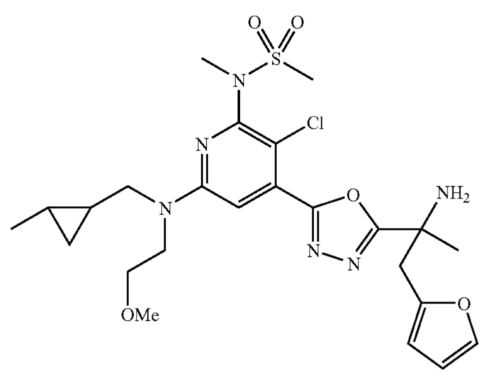 | 553 |
| 61 | 10.2.1 | Ex 49 | 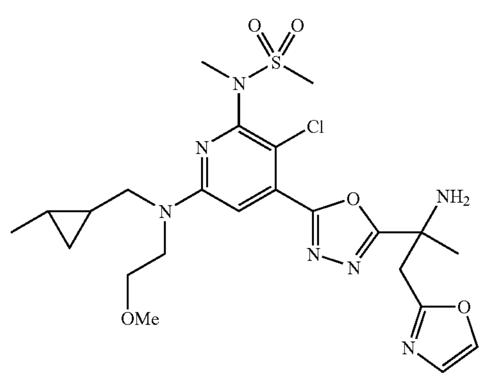 [SMILES: COCCN(CC1CC1C)c1cc(-c2nnc(C(C)(N)Cc3ncco3)o2)c(Cl)c(N(C)S(C)(=O)=O)n1] | 554 |

TABLE 4-continued

| | | | 3-Cl Derivatives | |
|---|---|---|---|---|
| Ex # | intermediate | Mode of prep | structure | ES M + 1 |
| 62 | 10.2.1 | Ex x49 | | 594 |
| 63 | 10.2.1 | Ex 49 | | 594 |
| 64 | 10.2.1 | Ex 49 | | 738 |

TABLE 4-continued

3-Cl Derivatives

| Ex # | intermediate | Mode of prep | structure | ES M + 1 |
|---|---|---|---|---|
| 65 | 10.2.1 | Ex 49 | 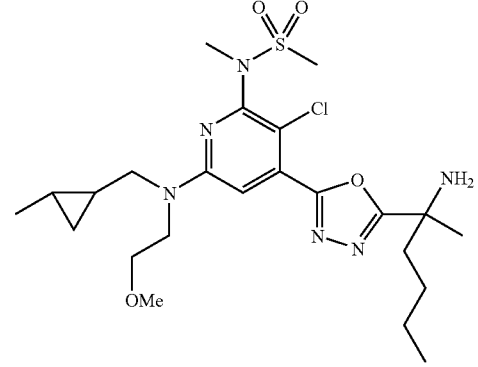 [SMILES: CCCCC(C)(N)c1nnc(-c2cc(N(CCOC)CC3CC3C)nc(N(C)S(C)(=O)=O)c2Cl)o1] | 529 |

N²-{4-{5-[(1R)-1-amino-1-methyl-2-phenylethyl]-1,3,4-oxadiazol-2-yl}-5-chloro-6-[methyl(methylsulfonyl)amino]pyridin-2-yl}-N,N-dimethyl-N²-[(trans-2-methylcyclopropyl)methyl]glycinamide

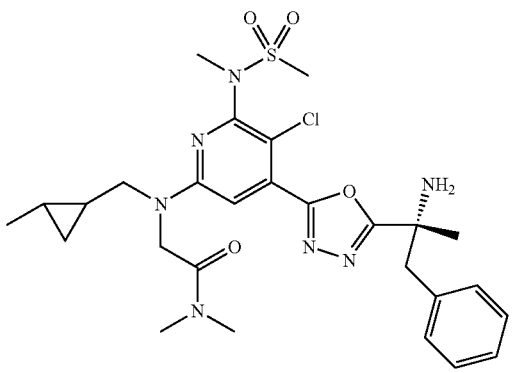 [SMILES: CC1CC1CN(CC(=O)N(C)C)c1cc(-c2nnc([C@](C)(N)Cc3ccccc3)o2)c(Cl)c(N(C)S(C)(=O)=O)n1]

Step A: Coupling

To a 13×100 mm screw cap test tube containing Intermediate 8.4.1 (25 mg, 0.04 mmol), dimethyl amine (5.1 mg, 0.11 mmol), HOAt (2.6 mg, 0.02 mmol) in DMF (0.2 mL) was added EDC-HCl (10.2 mg, 0.05 mmol). After stirring for 3 h the reaction was diluted with aq. KHSO₄ and extracted with EtOAc (2×10 mL). The organic layers were washed with brine, dried over Na₂SO₄ and concentrated to dryness to give the crude Boc-protected amide: LC/MS [M+H]=689.1 (chlorine pattern)

Step B: Boc Removal

The above amide from step A was dissolved in 0.3 mL CH₂Cl₂, cooled on a ice-bath and treated with TFA (16 µL, 0.2 mmol). Upon disappearance of starting material the reaction was concentrated under a stream of nitrogen and purified by RP-HPLC. Product containing fractions were freeze-dried to give title compound as a white solid: ¹H NMR (400 MHz, CDCl₃) δ 7.32 (m, 3H), 7.10 (s, 1H), 7.08 (m, 2H), 4.54 (s, 2H), 3.55 (dd, J=(br s, 1H), 3.71 (m, 2H), 3.54 (m, 2H), 3.45 (s, 3H), 3.33-3.28 (m, 2H), 3.19 (s, 3H), 3.13 (s, 3H), 3.14 (s, 3H), 2.92 (s, 3H), 1.87 (s, 3H), 1.05 (d, J=5.9 Hz, 3H), 0.80 (m, 2H), 0.48 (m, 1H), 0.32 (m, 1H); LC/MS [M+H]=590.0

TABLE 5

Amide Derivatives

| Ex # | intermediate | Mode of prep | structure | ES M + 1 |
|---|---|---|---|---|
| 67 | 8.4.1 | Ex 66 | 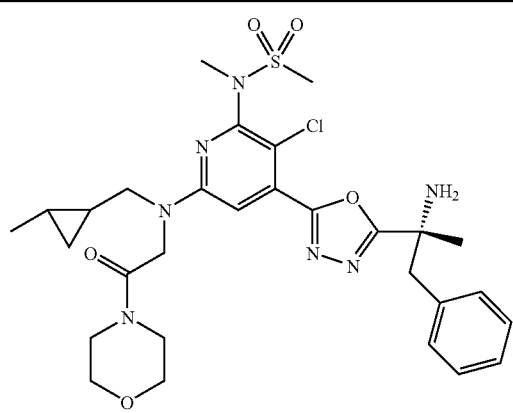 | 632 |

TABLE 5-continued

Amide Derivatives

| Ex # | intermediate | Mode of prep | structure | ES M + 1 |
|---|---|---|---|---|
| 68 | 8.4.1 | Ex 66 | 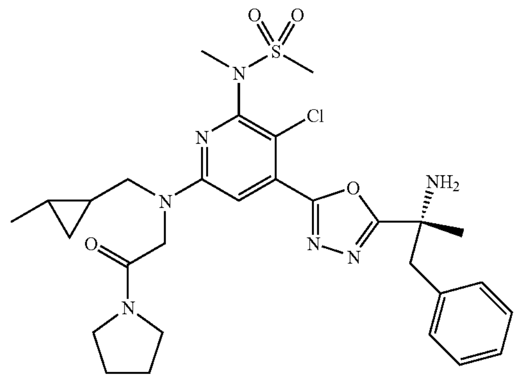 [SMILES: CC1CC1CN(CC(=O)N1CCCC1)c1cc(-c2nnc([C@](C)(N)Cc3ccccc3)o2)c(Cl)c(N(C)S(C)(=O)=O)n1] | 616 |
| 69 | 8.4.1 | Ex 66 | 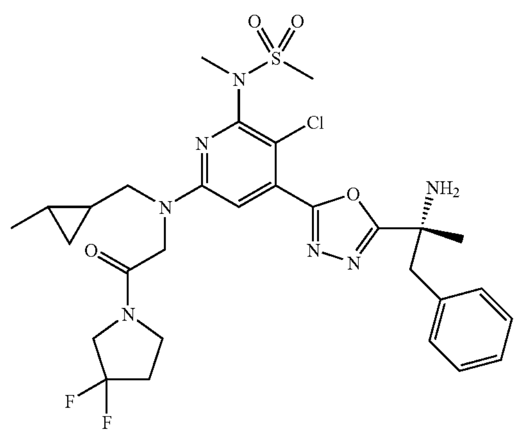 [SMILES: CC1CC1CN(CC(=O)N1CCC(F)(F)C1)c1cc(-c2nnc([C@](C)(N)Cc3ccccc3)o2)c(Cl)c(N(C)S(C)(=O)=O)n1] | 652 |
| 70 | 8.4.1 | Ex 66 | 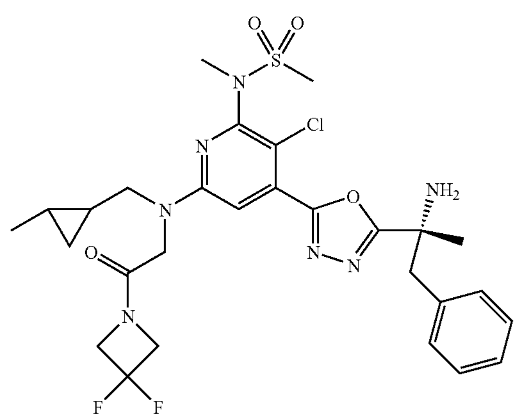 [SMILES: CC1CC1CN(CC(=O)N1CC(F)(F)C1)c1cc(-c2nnc([C@](C)(N)Cc3ccccc3)o2)c(Cl)c(N(C)S(C)(=O)=O)n1] | 638 |

EXAMPLE 71

N-(4-{5-[(1R)-1-amino-1-methyl-2-phenylethyl]-1,3,4-oxadiazol-2-yl}-3-chloro-6-{(2-cyclopropyl-2-oxoethyl)[(trans-2-methylcyclopropyl)methyl]amino}pyridin-2-yl)-N-methylmethanesulfonamide

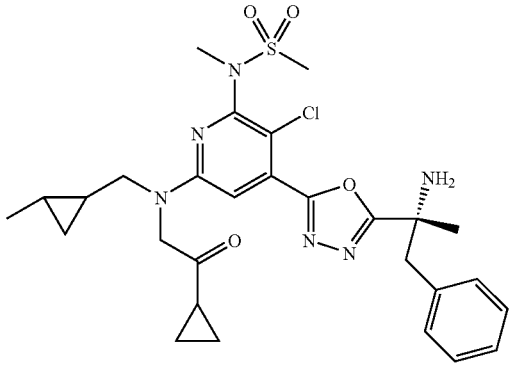 [SMILES: CC1CC1CN(CC(=O)C1CC1)c1cc(-c2nnc([C@](C)(N)Cc3ccccc3)o2)c(Cl)c(N(C)S(C)(=O)=O)n1]

Step A: Weinreb Amide Formation.

Using conditions similar to that described in Example 66, coupling of intermediate 8.4.1 with N,O-hydroxylamine dimethyl hydroxylamine provided the Weinreb amide: LC/MS [M+H]=706.0.

Step B: Grignard Addition.

In a flask containing Weinreb substrate from step A (40 mg, 0.06 mmol) in toluene (0.5 mL) at rt was added 5 equiv cyclopropyl Grignard (0.29 mmol, 1.0 M ether) in one portion. After 20 min. 2 mL aqueous NH$_4$Cl was added, followed by H$_2$O and EtOAc. The organic layer was isolated and washed with brine. The organic layers was dried over Na$_2$SO$_4$ and concentrated under reduced pressure. The crude was purified by RP-HPLC to give protected ketone: LC/MS [M=H]=687.0.

Step C: Boc Removal.

Intermediate from step B (10 mg, 0.01 mmol) was dissolved in 1.0 mL CH$_2$Cl$_2$, cooled on a ice-bath and treated with TFA (10 μL). Upon disappearance of starting material the reaction was concentrated under a stream of nitrogen and purified by RP-HPLC. Product containing fractions were freeze-dried to give title compound as a white solid: $^1$H NMR (400 MHz, CD$_3$OD) δ 7.31 (m, 3H), 7.06 (m, 3H), 4.65 (s, 2H), 3.52 (m, 2H), 3.42 (br s, 2H), 3.17 (s, 3H), 3.13 (s, 3H), 2.16 (m, 1H), 1.85 (s, 3H), 1.02 (d, J=6.0 Hz, 3H), 0.98 (m, 4H), 0.70 (m, 2H), 0.45 (m, 1H), 0.30 (m, 1H); LC/MS [M+H]=587.0.

EXAMPLE 72

N-(4-{5-[(1R)-1-amino-1-methyl-2-phenylethyl]-1,3,4-oxadiazol-2-yl}-3-chloro-6-{[(trans-2-methylcyclopropyl)methyl][2-(5-methyl-1,3,4-oxadiazol-2-yl)-2-oxoethyl]amino}pyridin-2-yl)-N-methylmethanesulfonamide

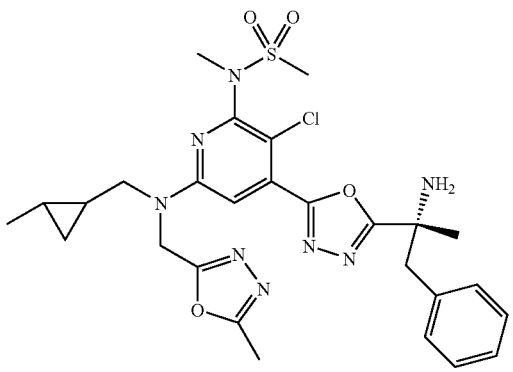 [SMILES: Cc1nnc(CN(CC2CC2C)c2cc(-c3nnc([C@](C)(N)Cc4ccccc4)o3)c(Cl)c(N(C)S(C)(=O)=O)n2)o1]

Step A: Coupling of 8.4.1 and Acetic Hydrazide.

Using conditions similar to that described in Example 66 coupling of intermediate 8.4.1 with acetic hydrazide provided the bis acylated hydrazide: LC/MS [M+H]=719.0.

Step B: Cyclodehydration.

To a 0° C. CH$_2$Cl$_2$ solution containing substrate from step A (60 mg, 0.08 mmol), polystyrene bound triphenylphosphine (100 mg, 0.13 mmol, 1.3 mmol/g, 200 mesh), and imidazole (8 mg, 0.12 mmol) was added CBr$_4$ (39 mg, 0.12 mmol) in one portion. The reaction was stirred for 48 h. At this time the mixture was filtered, concentrated and purified by RP-HPLC. Product containing fractions were pooled and isolated following an aqueous sodium bicarbonate/EtOAc workup. Final organic layers were washed with brine, dried over Na$_2$SO$_4$ and concentrated to give cyclized intermediate: LC/MS [M+H]=701.0

Step C: Boc Removal.

Intermediate from step B (56 mg, 0.08 mmol) was dissolved in 6.0 mL CH$_2$Cl$_2$, cooled on a ice-bath and treated with TFA (100 μL). Upon disappearance of starting material the reaction was concentrated under a stream of nitrogen and purified by RP-HPLC. Product containing fractions were freeze-dried to give title compound as a white solid: LC/MS [M+H]=600.9 (chlorine pattern).

EXAMPLE 73

N-(4-{5-[(1R)-1-amino-1-methyl-2-phenylethyl]-1,3,4-oxadiazol-2-yl}-3-chloro-6-{[(2-methylcyclopropyl)methyl][2-(1,3,4-oxadiazol-2-yl)-2-oxoethyl]amino}pyridin-2-yl)-N-methylmethanesulfonamide

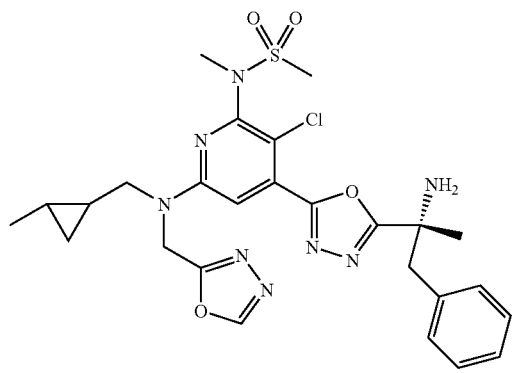 [SMILES: CC1CC1CN(Cc1nnco1)c1cc(-c2nnc([C@](C)(N)Cc3ccccc3)o2)c(Cl)c(N(C)S(C)(=O)=O)n1]

Prepared from intermediate 8.4.1 and formylhydrazide as described in the preparation of N-(4-{5-[(1R)-1-amino-1-methyl-2-phenylethyl]-1,3,4-oxadiazol-2-yl}-3-chloro-6-{[(trans-2-methylcyclopropyl)methyl][2-(5-methyl-1,3,4-oxadiazol-2-yl)-2-oxoethyl]amino}pyridin-2-yl)-N-methyl-methanesulfonamide (example 72). MS M+1=587.

EXAMPLE 74

N-[4-{5-[(1R)-1-amino-1-methyl-2-phenylethyl]-1,3-oxazol-2-yl}-3-chloro-6-({[trans-2-methylcyclopropyl]methyl}amino)pyridin-2-yl]-N-methylmethanesulfonamide

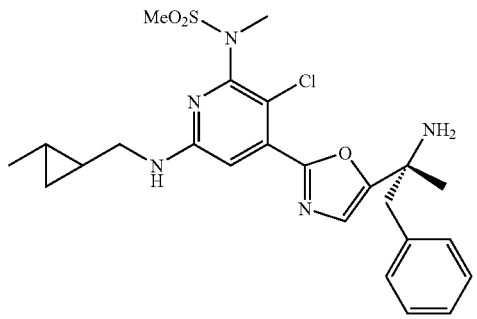 [SMILES: CC1CC1CNc1cc(-c2ncc([C@](C)(N)Cc3ccccc3)o2)c(Cl)c(N(C)S(C)(=O)=O)n1]

Step A: Debenzylation

To a solution of tert-butyl [(1R)-1-(2-{2-(benzyl{[trans-(1S,2S)-2-methyl cyclopropyl]methyl}amino)-6-[methyl(methylsulfonyl)amino]pyridin-4-yl}-1,3-oxazol-5-yl)-1-methyl-2-phenylethyl]carbamate (intermediate 6.2.1, 0.050 g, 0.076 mmol) in 5 mL EtOH was added trifluoroacetic acid (0.006 mL, 0.076 mmol) and 20% Pd(OH)$_2$ on carbon (0.011 g). A balloon of H$_2$ was attached, and the flask was evacuated and opened to H$_2$ (3×). After 15 h, the reaction was evacuated and opened to Ar (3×), filtered through a pad of celite and concentrated to afford tert-butyl [(1R)-1-methyl-1-(2-{2-({[trans-(1S,2S)-2-methylcyclopropyl]methyl}amino)-6-[methyl(methylsulfonyl)amino]pyridin-4-yl}-1,3-oxazol-5-yl)-2-phenylethyl]carbamate. $^1$H NMR (400 MHz, CDCl$_3$) δ 7.31-7.26 (m, 4H), 7.12 (s, 1H), 7.04-7.03 (m, 2H), 6.98 (s, 1H), 3.50 (m, 1H), 3.43-3.34 (m, 4H), 3.23-3.13 (m, 4H), 3.11 (d, J=13.2 Hz, 1H), 1.60 (s, 3H), 1.41 (s, 9H), 1.09 (d, J=5.9 Hz, 3H), 0.85 (m, 1H), 0.72 (m, 1H), 0.48 (m, 1H), 0.39 (m, 1H). LCMS (M+H)=570.

Step B: Boc Deprotection

To a solution of tert-butyl [(1R)-1-methyl-1-(2-{2-({[trans-(1S,2S)-2-methylcyclopropyl]methyl}amino)-6-[methyl(methylsulfonyl)amino]pyridin-4-yl}-1,3-oxazol-5-yl)-2-phenylethyl]carbamate (0.040 g, 0.070 mmol) in 0.5 mL CH$_2$Cl$_2$ was added 0.5 mL trifluoroacetic acid. After 1 h, the reaction was lyophilized to obtain N-[4-{5-[(1R)-1-amino-1-methyl-2-phenylethyl]-1,3-oxazol-2-yl}-6-({[(1S,2S)-2-methylcyclopropyl]methyl}amino)pyridin-2-yl]-N-methylmethanesulfonamide as a yellow solid. $^1$H NMR (400 MHz, d$_4$-MeOH) δ 7.29-7.26 (m, 3H), 7.22 (s, 1H), 7.06 (d, J=1.1 Hz, 1H), 7.03-7.01 (m, 2H), 6.95 (d, J=1.1 Hz, 1H), 3.47 (d, J=13.4 Hz, 1H), 3.37 (s, 3H), 3.28-3.23 (m, 3H), 3.19 (s, 3H), 1.72 (s, 3H), 1.06 (d, J=5.9 Hz, 3H), 0.85 (m, 1H), 0.71 (m, 1H), 0.43 (m, 1H), 0.27 (m, 1H). LCMS (M+H)=470.

Step C: Chlorination

To a solution of N-[4-{5-[(1R)-1-amino-1-methyl-2-phenylethyl]-1,3-oxazol-2-yl}-6-({[(1S,2S)-2-methylcyclopropyl]methyl}amino)pyridin-2-yl]-N-methylmethanesulfonamide (0.009 g, 0.015 mmol) in 0.3 mL CH$_2$Cl$_2$ was added 0.09 mL of a 0.15M stock solution of NCS in CH$_2$Cl$_2$. After 15 h, a further 0.10 mL CH$_2$Cl$_2$ and 0.1 mL 0.15 M stock solution of NCS in CH$_2$Cl$_2$ were added. After 24 h, the reaction was concentrated, redissolved in DMF and purified by preparative HPLC to afford N-[4-{5-[(1R)-1-amino-1-methyl-2-phenylethyl]-1,3-oxazol-2-yl}-3-chloro-6-({[(1S,2S)-2-methylcyclopropyl]methyl}amino)pyridin-2-yl]-N-methylmethanesulfonamide as a yellow solid. $^1$H NMR (400 MHz, d$_4$-MeOH) δ 7.30-7.29 (m, 3H), 7.24 (s, 1H), 7.04-7.02 (m, 3H), 3.47 (d, J=13.3 Hz, 1H), 3.28 (s, 3H), 3.26-3.20 (m, 5H), 1.71 (s, 3H), 1.06 (d, J=5.9 Hz, 3H), 0.85 (m, 1H), 0.71 (m, 1H), 0.43 (m, 1H), 0.27 (m, 1H). LCMS (M+H)=505 (chlorine pattern).

EXAMPLE 75

N-(4-{5-[(1R)-1-amino-1-methyl-2-phenylethyl]-1,3-oxazol-2-yl}-3-chloro-6-{(2-methoxyethyl)[(2-methylcyclopropyl)methyl]amino}pyridin-2-yl)-N-methylmethanesulfonamide

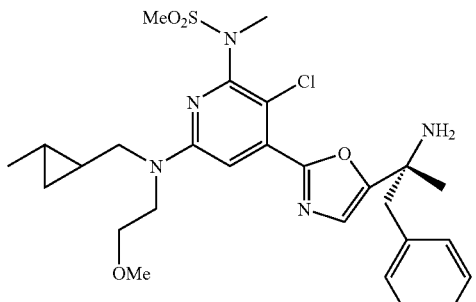

Prepared from intermediate 6.2.2 by the following sequence: Boc removal and NCS chlorination, as described above. MS M+1=562.

EXAMPLE 76

N-(4-{5-[(1R)-1-amino-1-methyl-2-phenylethyl]-1,314-oxadiazol-2-yl}-3-fluoro6-{(2-methoxyethyl)[(trans-2-methylcyclopropyl)methyl]amino}pyridin-2-yl)-N-methylmethanesulfonamide (Scheme 9)

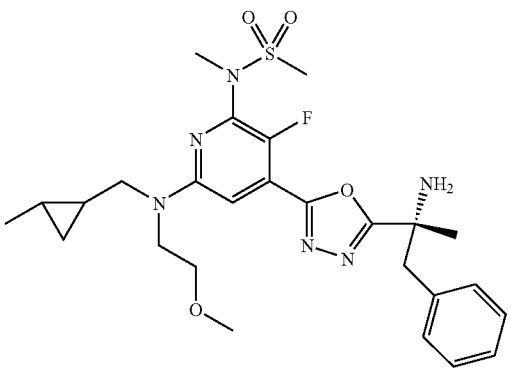 [SMILES: COCCN(CC1CC1C)c1cc(-c2nnc([C@](C)(N)Cc3ccccc3)o2)c(F)c(N(C)S(C)(=O)=O)n1]

Prepared from intermediate 9.1.1 and Boc-D-alpha-methyl-phenylalanine using a similar procedure as described in the preparation of intermediate 5.2c.1. MS M+1=547.

EXAMPLE 77

N-(4-{5-[(1R)-1-amino-1-methyl-2-phenylethyl]-1,3,4-oxadiazol-2-yl}-3-fluoro-6-{[(trans-2-methylcyclopropyl)methyl]amino}pyridin-2-yl)-N-methyl-methanesulfonamide (Scheme 9)

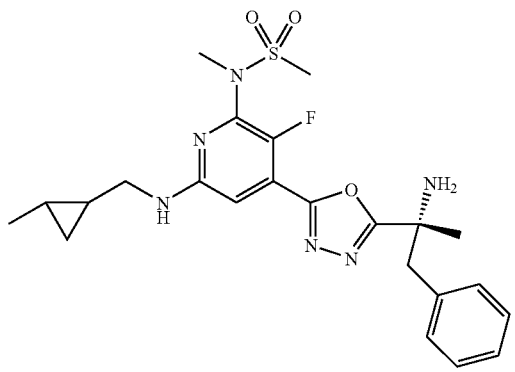 [SMILES: CC1CC1CNc1cc(-c2nnc([C@](C)(N)Cc3ccccc3)o2)c(F)c(N(C)S(C)(=O)=O)n1]

Prepared from intermediate 9.1.2 and Boc-D-alpha-methyl-phenylalanine using a similar procedure as described in the preparation of intermediate 5.2c.1, including a hydrogenation mediated debenzylation prior to Boc removal. MS M+1=489.

EXAMPLE 78

N-(4-{5-[(1R)-1-amino-1-methyl-2-phenylethyl]-1,3,4-oxadiazol-2-yl}-3-cyano-6-{[(trans-2-methylcyclopropyl)methyl]amino}pyridin-2-yl)-N-methyl-methanesulfonamide (Scheme 9)

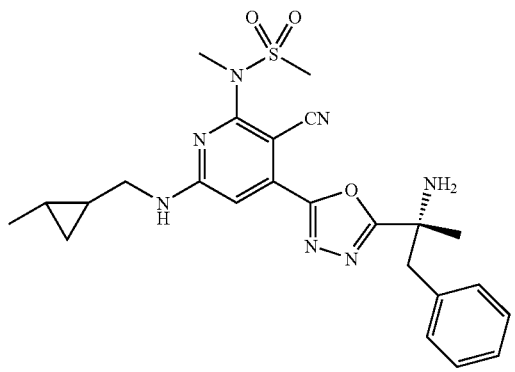 [SMILES: CC1CC1CNc1cc(-c2nnc([C@](C)(N)Cc3ccccc3)o2)c(C#N)c(N(C)S(C)(=O)=O)n1]

To tert-butyl [(1R)-1-(5-{3-bromo-6-{[(trans-2-methylcyclopropyl)methyl]amino}-2-[methyl(methylsulfonyl)amino]pyridin-4-yl}-1,3,4-oxadiazol-2-yl)-1-methyl-2-phenylethyl]carbamate (intermediate 9.3.1, 18 mg, 0.028 mmol) was added $Zn(CN)_2$ (7 mg, 0.055 mg), Zn dust (spatula tip, ~1 mg, ~0.014 mmol) and $Pd(t-Bu_3)_2$ (3 mg, 0.006 mmol). Degassed dimethylacetamide (0.3 mL) was added, and the reaction was degassed further with Ar, then microwaved at 130° C. for 90 min. The reaction was filtered and purified by reverse-phase preparative HPLC to afford a mixture of tert-butyl [(1R)-1-(5-{3-cyano-6-{[(trans-2-methylcyclopropyl)methyl]amino}-2-[methyl(methylsulfonyl)amino]pyridin-4-yl}-1,3,4-oxadiazol-2-yl)-1-methyl-2-phenylethyl] carbamate and final compound N-(4-{5-[(1R)-1-amino-1-methyl-2-phenylethyl]-1,3,4-oxadiazol-2-yl}-3-cyano-6-{[(trans-2-methylcyclopropyl)methyl]amino}pyridin-2-yl)-N-methylmethanesulfonamide. The former was elaborated to the latter derivative using a 1:1 solution of $TFA/CH_2Cl_2$. $^1$H NMR ($CDCl_3$, 400 MHz) δ 7.34-7.32 (m, 3H), 7.15 (br s), 7.10-7.07 (m, 3H), 3.45 (s, 2H), 3.34 (s, 3H), 3.33 (m, 2H), 3.27 (s, 3H), 1.87 (s, 3H), 1.06 (d, J=5.9 Hz, 3H), 0.83 (m, 1H), 0.71 (m, 1H), 0.46 (m, 1H), 0.31 (m, 1H); LCMS (2M+H)=991; Exact mass calculated for $C_{24}H_{30}N_7O_3S$: 496.2126; measured: 496.2149.

The following abbreviations are used throughout the text:
Me: methyl
Bu: butyl
i-Bu: isobutyl
t-Bu: tert butyl
Et: ethyl
Pr: propyl
i-Pr: isopropyl
Ar: aryl
Ph: phenyl
Py: pryridine
Ac: acetyl
NaHMDS: sodium hexamethydisilazide
EDC: ethyl-3-(3-dimethylaminopropyl)-carbodiimide
HOAt: 1-hydroxy-7-azabenzotriazole
DMF: N,N'-dimethyl formamide
THF: tetrahydrofuran
DMSO: dimethylsulfoxide
EDTA: ethylene diamine tetraacetic acid
Boc: tert-butyloxy carbonyl
BOP: Benzotriazol-1-yloxy-tris(dimethylamino)phosphonium hexafluorophosphate
CHAPS: 3-[(3-cholamidopropyl)dimethylammonio]-2-hydroxy-1-propanesulfonate
TFA: trifluoroacetic acid
NCS: N-chloro succinimide
DCE: dichloroethane
DIPEA: diisopropylethylamine
DCM: dichloromethane
DMA: N,N-dimethylacetamide
aq: aqueous
rt: room temperature
HPLC: high performance liquid chromatography While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

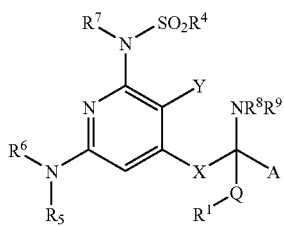

X is

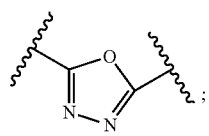 [SMILES: *c1nnc(*)o1]

Y is selected from the group consisting of:
(1) halogen,
(2) cyano,
(3) —$C_{2-6}$ alkyl, and
(4) —$C_{6-10}$ aryl;

A is selected from the group consisting of
(1) hydrogen,
(2) —$C_{1-10}$ alkyl, and
(3) —$C_{2-10}$ alkenyl,
wherein said alkyl or alkenyl is unsubstituted or substituted with one or more moieties selected from the group consisting of:
(a) halo,
(b) —$C_{3-12}$ cycloalkyl,
(c) —OH,
(d) —CN,
(e) —O—$C_{1-10}$ alkyl, and
(f) phenyl, wherein said phenyl is unsubstituted or substituted with one or more moieties selected from the group consisting of:
(i) halo,
(ii) —OH,
(iii) —CN,
(iv) —O—$C_{1-10}$ alkyl,
(v) —$C_{1-10}$ alkyl, and
(vi) —$C_{3-12}$ cycloalkyl;

Q is —$C_{0-3}$ alkyl, wherein said alkyl is unsubstituted or substituted with one or more moieties selected from the group consisting of:
(1) halo,
(2) —$C_{3-12}$ cycloalkyl,
(3) —OH,
(4) —CN,
(5) —O—$C_{1-10}$ alkyl, and
(6) —$C_{1-10}$ alkyl;

$R^1$ is selected from the group consisting of
(1) aryl selected from the group consisting of phenyl and napthyl,
(2) —$C_{1-10}$ alkyl, and
(3) —$C_{3-8}$ cycloalkyl, wherein said cycloalkyl is optionally fused to a $C_{6-10}$ aryl group,
wherein said aryl, said alkyl, and said cycloalkyl are unsubstituted or substituted with one or more moieties selected from the group consisting of:
(a) halo,
(b) —$C_{1-10}$ alkyl, wherein said alkyl is unsubstituted or substituted with halogen,
(c) —OH,
(d) —CN,
(e) —O—$C_{1-10}$ alkyl,
(f) —$C_{3-12}$ cycloalkyl, and
(g) —$NR^{10}R^{11}$, wherein $R^{10}$ and $R^{11}$ are each independently selected from the group consisting of
(i) hydrogen,
(ii) —$C_{1-10}$ alkyl, and
(iii) —$C_{0-6}$ alkylene-$C_{6-10}$ aryl;

$R^8$ and $R^9$ are selected from the group consisting of
(1) hydrogen,
(2) $C_{1-10}$ alkyl, and
(3) $C_{0-6}$ alkylene-$C_{6-10}$ aryl;

$R^4$ is selected from the group consisting of
(1) —$C_{1-10}$ alkyl, and
(2) —$NR^{12}R^{13}$, wherein $R^{12}$ and $R^{13}$ are selected from the group consisting of
(a) hydrogen,
(b) $C_{1-10}$ alkyl, and
(c) $C_{0-6}$ alkylene-$C_{6-10}$ aryl,
or $R^{12}$ and $R^{13}$ represent 4, 5 or 6 ring atoms selected from the group consisting of $CR^aR^b$, S, $NR^c$ and O, which form a non-aromatic ring with the nitrogen to which they are attached,
wherein said alkyl, and alkylene is unsubstituted or substituted with one or more moieties selected from the group consisting of:
(a) halo,
(b) —OH,
(c) —CN,
(d) —O—$C_{1-10}$ alkyl,
(e) —$C_{1-10}$ alkyl,
(f) —$C_{3-12}$ cycloalkyl,
(g) aryl selected from the group consisting of phenyl and napthyl,
(h) —C(=O)—$C_{1-10}$ alkyl, and
(i) aryl selected from the group consisting of phenyl and naphthyl, wherein said aryl is unsubstituted or substituted with one or more moieties selected from the group consisting
(i) halo,
(ii) —OH,
(iii) —CN,
(iv) —O—$C_{1-10}$ alkyl,
(v) —$C_{3-12}$ cycloalkyl, and
(vi) —$C_{1-10}$ alkyl;

$R^7$ is selected from the group consisting of
(1) hydrogen,
(2) —$C_{1-10}$ alkyl,
(3) —$C_{3-7}$ cycloalkyl, and
(4) —$C_{6-10}$ aryl,
wherein said alkyl, said cycloalkyl, and said aryl is unsubstituted or substituted with one or more moieties selected from the group consisting of::
(a) halo,
(b) —OH,
(c) —CN,
(d) —O—$C_{1-10}$ alkyl,
(e) —$C_{3-12}$ cycloalkyl,
(f) a non-aromatic cyclic group consisting of 4, 5 or 6 ring atoms selected from the group consisting of $CR^aR^b$, S, $NR^c$ and O, (g) aryl selected from the group consisting of phenyl and napthyl, and (h) —$C_{5-12}$ heteroaryl, wherein said cycloalkyl, said aryl and said heteroaryl is unsubstituted or substituted with one or more moieties selected from the group consisting of:
(i) halo,
(ii) —OH,
(iii) —CN,
(iv) —O—$C_{1-10}$ alkyl,
(v) —$C_{3-12}$ cycloalkyl, and
(vi) aryl selected from the group consisting of phenyl and napthyl;

or $R^4$ and $R^7$ may be linked to form a —$CH_2CH_2CH_2$- group;

$R^5$ and $R^6$ are independently selected from the group consisting of
(1) hydrogen,
(2) —$C_{1-10}$ alkyl,
(3) —$C_{2-10}$ alkenyl,
(4) —$C_{2-10}$ alkynyl, and
(5) —$C_{1-10}$ alkylene-$C_{3-12}$ cycloalkyl;

wherein said alkyl, alkylene, said cycloalkyl, said alkenyl and said alkynyl is unsubstituted or substituted with one or more moieties selected from the group consisting of:
(a) halo,
(b) —OH,
(c) —CN,
(d) —$C_{1-10}$ alkyl,
(e) —$C_{3-12}$ cycloalkyl,
(f) —O—$C_{1-10}$ alkyl, wherein said alkyl is unsubstituted or substituted with —O—$C_{1-10}$ alkyl-(—O—$C_{1-10}$ alkyl)$_m$,
(g) phenyl,
(j) —$NR^{14}R^{15}$, wherein $R^{14}$ and $R^{15}$ are selected from the group consisting of
  (A) hydrogen,
  (B) —$C_{1-10}$ alkyl, and
  (C) —$C_{0-6}$ alkyl-$C_{6-10}$ aryl,
(k) —C(=O)—$OR^{16}$, wherein $R^{16}$ is selected from the group consisting of
  (A) hydrogen,
  (B) —$C_{1-10}$ alkyl, and
  (C) —$C_{0-6}$ alkylene—$C_{6-10}$ aryl, and
(l) —C(=O)—$NR^{17}R^{18}$, wherein $R^{17}$ and $R^{18}$ are selected from the group consisting of
  (A) hydrogen,
  (B) —$C_{1-10}$ alkyl, and
  (C) —$C_{0-6}$ alkylene—$C_{6-10}$ aryl,
or $R^{17}$ and $R^{18}$ represent 4, 5 or 6 ring atoms selected from the group consisting of $CR^aR^b$, S, $NR^c$ and O, which form a non-aromatic ring with the nitrogen to which they are attached, and
(m) —C(=O)—$R^{19}$, wherein $R^{19}$ is selected from the group consisting of
  (A) —$C_{1-10}$ alkyl,
  (B) —$C_{3-7}$ cycloalkyl, and
  (C) —$C_{0-6}$ alkylene-$C_{6-10}$ aryl, or $R^5$ and $R^6$ are joined together with the nitrogen atom to which they are attached to form a 4-6 membered ring, which is unsubstituted or substituted with one or more moieties selected from the group consisting of:
(a) —$C_{1-10}$ alkyl,
(b) —$C_{3-12}$ cycloalkyl,
(c) —$(CH_2)_n$-phenyl,
(d) —$C_{2-10}$ alkenyl, and
(e) —$C_{2-10}$ alkynyl, wherein said alkyl, alkenyl and alkynyl is unsubstituted or substituted with one or more moieties selected from the group consisting of:
(i) halo,
(ii) —OH,
(iii) —CN,
(iv) —O—$C_{1-10}$ alkyl, and
(v) —$C_{3-12}$ cycloalkyl, and said cycloalkyl and phenyl is unsubstituted or substituted with one or more moieties selected from the group consisting of:
(i) halo,
(ii) —$C_{1-10}$ alkyl,
(iii) —OH,
(iv) —CN,
(v) —$C_{3-12}$ cycloalkyl, and
(vi) —O—$C_{1-10}$ alkyl;

$R^a$, $R^b$ and $R^c$ are each independently selected from the group consisting of
(1) hydrogen,
(2) halogen,
(3) —$C_{1-6}$ alkyl, and
(4) —C(=O)—$C_{1-6}$ alkyl;

m is 0, 1 or 2;

n is 0, 1, 2, 3 or 4;

or an individual entantiomer or diastereomer thereof, or a pharmaceutically acceptable salt of said compound, said individual enantiomer, or diastereomer.

2. A compound of claim 1 wherein Y is halogen.

3. A compound of claim 1 wherein $R^1$ is phenyl, Q is $CH_2$, $R^8$ and $R^9$ are hydrogen, and A is $C_{1-6}$ alkyl.

4. A compound of claim 1 wherein $R^4$ and $R^7$ are $C_{1-10}$ alkyl.

5. A compound of claim 4 wherein $R^4$ is methyl or isopropyl and $R^7$ is methyl.

6. A compound of claim 1 which is a compound of formula (II)

where A, X, Y, Q, $R^1$, $R^4$, $R^5$, $R^7$, $R^8$ and $R^9$ are as defined in claim 1, or an individual entantionmer or diastereomer thereof, or a pharmaceutically acceptable salt of said compound, said individual enantiomer, or diastereomer.

7. A compound of claim 6, wherein $R^1$ is phenyl, Q is $CH_2$, $R^8$ and $R^9$ are hydrogen, and A is —$C_{1-10}$ alkyl.

8. A compound of claim 6, wherein $R^5$ is hydrogen or $C_{1-10}$ alkyl, wherein said $C_{1-10}$ alkyl is unsubstituted or substituted with one or more:
(a) —O—$C_{1-10}$ alkyl, wherein said alkyl is unsubstituted or substituted with —O—$C_{1-10}$ alkyl-(—O—$C_{1-10}$ alkyl)$_m$, or
(b) —C(=O)—$R^{19}$, wherein $R^{19}$ is selected from the group consisting of (i) —$C_{1-10}$ alkyl, (ii) —$C_{3-7}$ cycloalkyl, or (iii) —$C_{0-6}$ alkylene-$C_{6-10}$ aryl.

9. A compound of claim 1 which is a compound of formula (III)

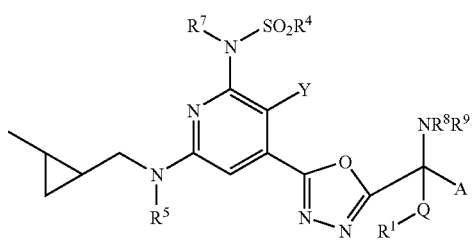

wherein A, X, Y, Q, $R^1$, $R^4$, $R^5$, $R^7$, $R^8$ and $R^9$ are as defined in claim 1, or an individual entantiomer or diastereomer thereof, or a pharmaceutically acceptable salt of said compound, said individual enantiomer, or diastereomer.

10. A compound of claim 9, wherein $R^1$ is phenyl, Q is $CH_2$, $R^8$ and $R^9$ are hydrogen, and A is —$C_{1-10}$ alkyl.

11. A compound of claim 9, wherein $R^5$ is hydrogen or $C_{1-10}$ alkyl wherein said $C_{1-10}$ alkyl is unsubstituted or substituted with one or more:

(a) —O—$C_{1-10}$ alkyl, wherein said alkyl is unsubstituted or substituted with —O—$C_{1-10}$ alkyl-(—O—$C_{1-10}$ alkyl)$_m$, or (c) —C(=O)—$R^{19}$, wherein $R^{19}$ is selected from the group consisting of (i) —$C_{1-10}$ alkyl, (ii) —$C_{3-7}$ cycloalkyl, or (iii) —$C_{0-6}$ alkylene-$C_{6-10}$ aryl.

12. A compound of claim 11, which is selected from the group consisting of

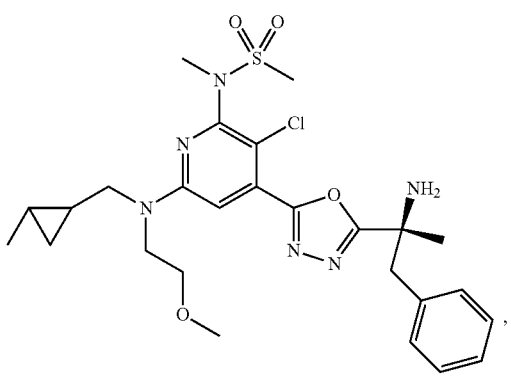

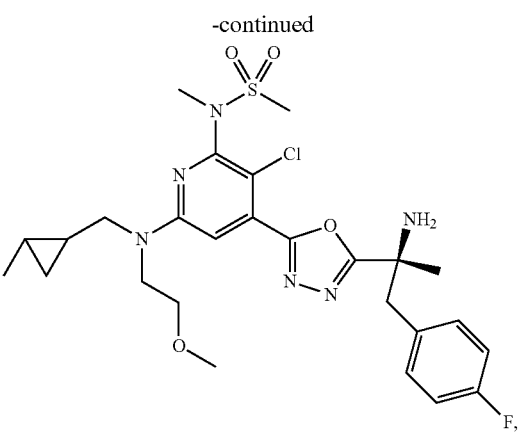

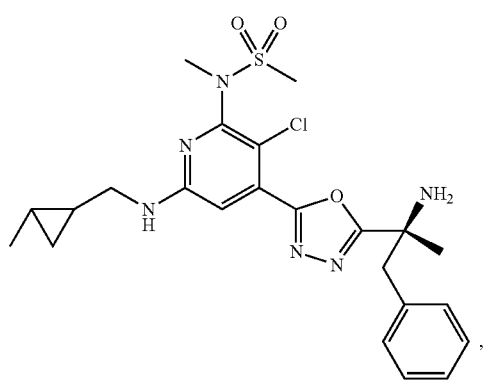

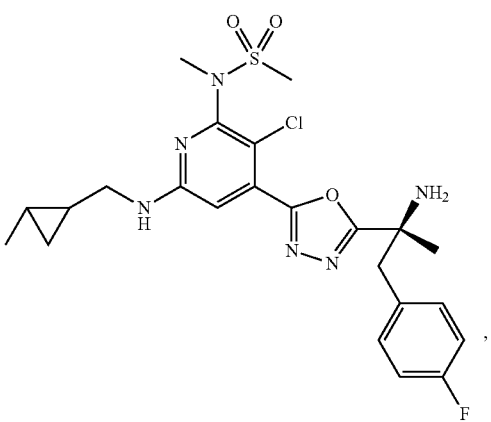

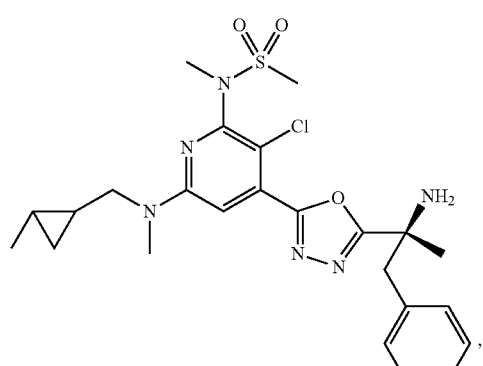

131
-continued
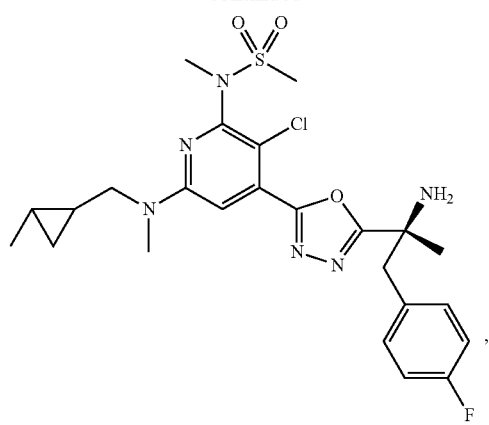
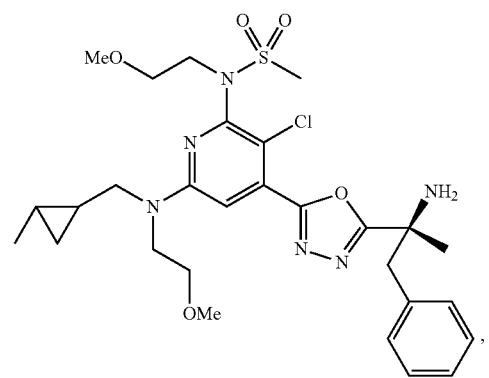
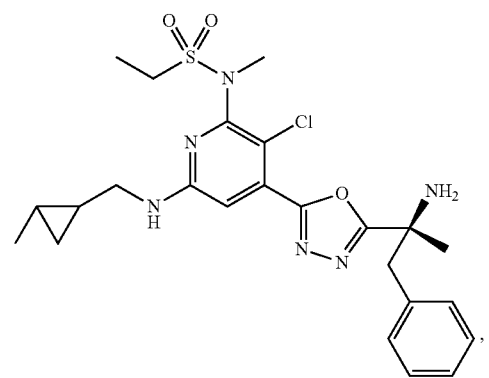
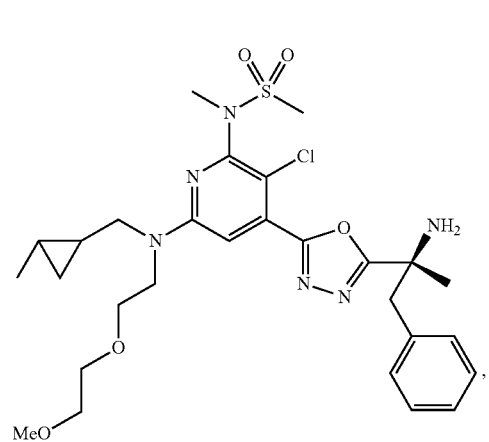
132
-continued
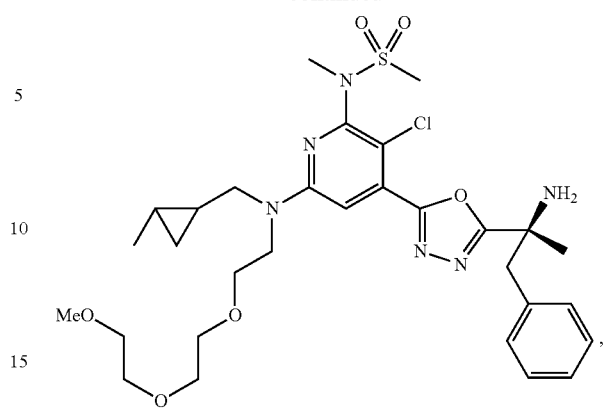
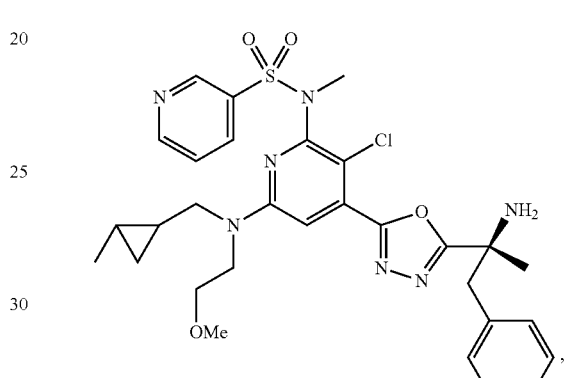
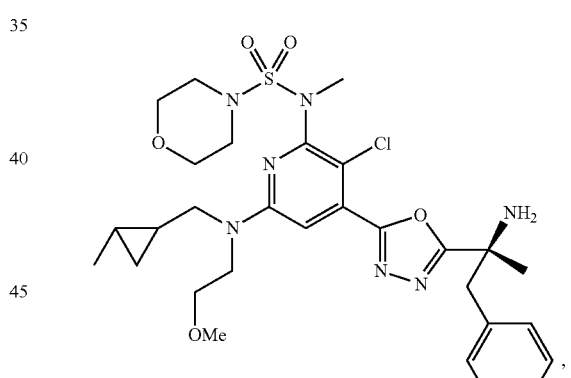
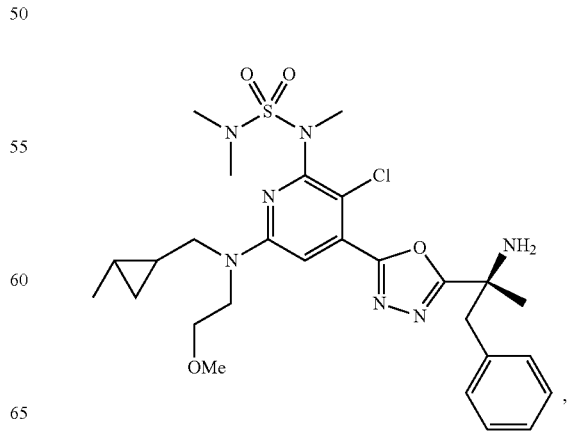

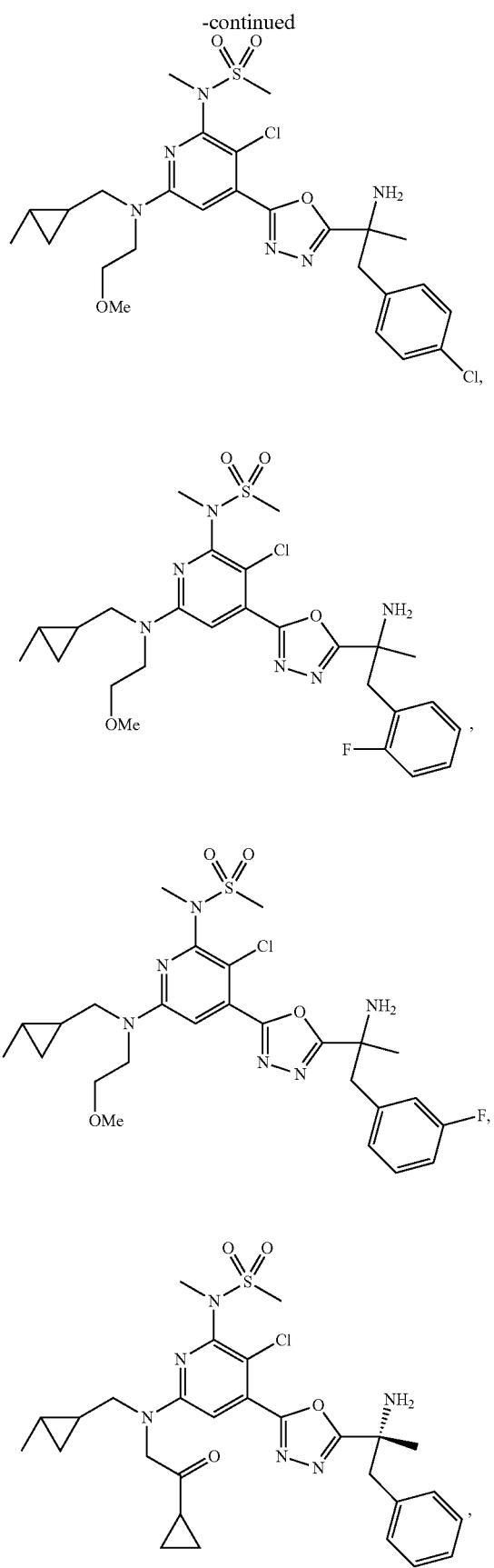

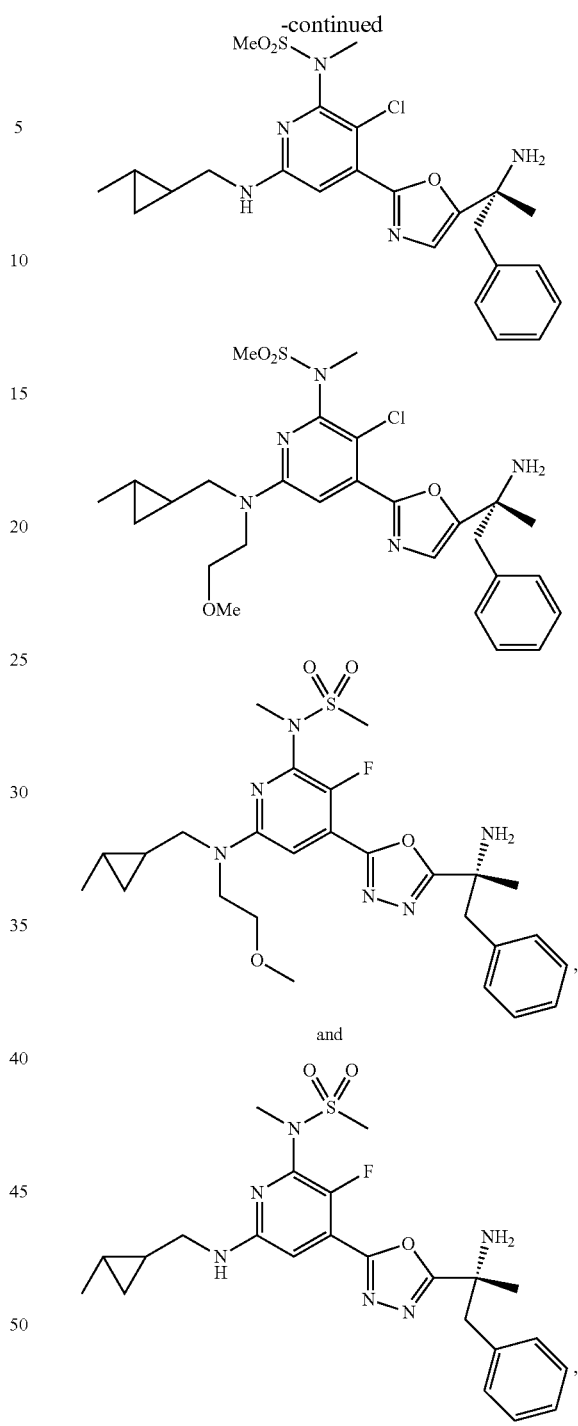

or a pharmaceutically acceptable salt thereof.

13. A pharmaceutical composition comprising a therapeutically effective amount of a compound of claim 1 or a pharmaceutically acceptable salt thereof and a pharmaceutically acceptable carrier.

14. A method of treating Alzheimer's disease in a patient in need thereof comprising administering to the patient a therapeutically effective amount of a compound of claim 1 or a pharmaceutically acceptable salt thereof.

* * * * *